US009808493B2

(12) United States Patent
Stanton et al.

(10) Patent No.: US 9,808,493 B2
(45) Date of Patent: Nov. 7, 2017

(54) EXOPOLYSACCHARIDE-PRODUCING BACTERIA, AND USES THEREOF FOR PROTECTING HEART HEALTH

(71) Applicants: University College Cork—National University of Ireland, Cork, Cork (IE); Agriculture and Food Development Authority (TEAGASC), County Carlow (IE)

(72) Inventors: Catherine Stanton, County Cork (IE); Paul Ross, County Cork (IE); Gerald F. Fitzgerald, Cork (IE); Noel Caplice, County Cork (IE); Fergus Shanahan, Cork (IE)

(73) Assignees: University College Cork—National University of Ireland, Cork, Cork (IE); Agriculture and Food Development Authority (TEAGASC), Co Carlow (IE)

( * ) Notice: Subject to any disclaimer, the term of this patent is extended or adjusted under 35 U.S.C. 154(b) by 76 days.

(21) Appl. No.: 14/425,236

(22) PCT Filed: Sep. 2, 2013

(86) PCT No.: PCT/EP2013/068119
§ 371 (c)(1),
(2) Date: Mar. 2, 2015

(87) PCT Pub. No.: WO2014/033307
PCT Pub. Date: Mar. 6, 2014

(65) Prior Publication Data

US 2015/0329923 A1 Nov. 19, 2015

(30) Foreign Application Priority Data

Aug. 31, 2012 (EP) .................................... 12182693

(51) Int. Cl.
*A23C 9/123* (2006.01)
*C08B 37/00* (2006.01)
(Continued)

(52) U.S. Cl.
CPC .......... *A61K 35/747* (2013.01); *A23C 9/1234* (2013.01); *A23L 33/135* (2016.08); (Continued)

(58) Field of Classification Search
None
See application file for complete search history.

(56) References Cited

FOREIGN PATENT DOCUMENTS

| | | |
|---|---|---|
| CN | 101712939 | 9/2011 |
| WO | WO-03/053158 | 7/2003 |

(Continued)

OTHER PUBLICATIONS

Ruas-Madiedo et al. "Invited REview Methods for the Screening, Isolation, and Characterization of Exopolysaccharides Produced by Lactic Acid Bacteria." Journal of Dairy Science, American Dairy Science Association, US. vol. 88, No. 3, Mar. 1, 2005.*
Corsetti, et al., "Lactobacilli in sourdough fermentation", Food Research International, Elsevier Applied Science, Barking, GB, vol. 40, No. 5, Apr. 2007.
"LABocol: Cholesterol-Lowering Probiotic Yogurt", UCC Technology Summary, Oct. 2012.
(Continued)

*Primary Examiner* — Blaine Lankford
*Assistant Examiner* — Lauren K Van Buren
(74) *Attorney, Agent, or Firm* — Cesari and McKenna, LLP

(57) ABSTRACT

An isolated *Lactobacillus mucosae* (DPC6426) strain deposited with the National Collection of Industrial and Marine Bacteria Limited (NCIMB) on 27 Jul. 2012 under NCIMB Deposit Accession No. 42015.

6 Claims, 36 Drawing Sheets

A

B

(51) Int. Cl.

| | |
|---|---|
| ***C12N 1/20*** | (2006.01) |
| ***A61K 35/747*** | (2015.01) |
| ***C12P 19/04*** | (2006.01) |
| ***C12R 1/225*** | (2006.01) |
| ***A23L 33/135*** | (2016.01) |

(52) U.S. Cl.

CPC .............. *C08B 37/006* (2013.01); *C12N 1/20* (2013.01); *C12P 19/04* (2013.01); *C12R 1/225* (2013.01); *A23C 2220/206* (2013.01); *A23Y 2220/00* (2013.01)

(56) References Cited

FOREIGN PATENT DOCUMENTS

| | | | |
|---|---|---|---|
| WO | WO2011066659 | * | 6/2011 |
| WO | WO-2012/072245 | | 6/2012 |

OTHER PUBLICATIONS

Ruas-Madiedo, et al., "Invited Review: Methods for the Screening, Isolation, and Characterization of Exopolysaccharides Produced by Lactic Acid Bacteria", Journal of Dairy Science, American Dairy Science Association, US, vol. 88, No. 3, Mar. 2005.
Ruas-Madiedo, et al., "Screening of exopolysaccharide-producing Lactobacillus and Bifidobacterium strains isolated from the human intestinal microbiota", Applied and Environmental Microbiology, American Society for Microbiology, US, vol. 73, No. 13, Jul. 2007.

* cited by examiner

A

B

A

B

A

B

A.

B.

Viability of *Lb. mucosae* DPC 6426 in fermented milk

A

EPS concentration in fermented milk

B

C

* p ≤ 0.05, paired t-test

* p ≤ 0.001, paired t-test

EXOPOLYSACCHARIDE-PRODUCING BACTERIA, AND USES THEREOF FOR PROTECTING HEART HEALTH

CROSS REFERENCE TO RELATED APPLICATIONS

This application is the National Stage of International Application No. PCT/EP2013/068119, filed on Sep. 2, 2013, which claims the benefit of European Application No. 12182693.7, filed on Aug. 31, 2012. The contents of both applications are hereby incorporated by reference in their entirety.

FIELD OF THE INVENTION

This invention relates to a strain of *Lactobacillus mucosae* bacteria capable of producing an exopolysaccharide (EPS). The invention also relates to a pharmaceutical composition for the treatment of an individual suffering from cardiovascular disease, for use as a probiotic, and in the manufacture of dairy products such as, for example, yoghurt.

BACKGROUND TO THE INVENTION

Cardiovascular diseases (CVD) are a group of disorders of the heart and blood vessels including atherosclerosis and hyperlipidemia. CVD is the leading cause of death and morbidity in the European Union, and the prevalence of CVD among Irish population is on the increase. The progressive increase in the incidence of CVD is a major growing concern among many regulators and professionals involved in maintaining and promoting public health. CVD prevention remains unsatisfactory across Europe, largely due to poor control of CVD risk factors and the growing incidence of obesity.

Globally, a third of ischemic heart disease (IHD) is attributable to high cholesterol, and overall, raised cholesterol is estimated to cause 2.6 million deaths (4.5% of total) and 29.7 million disability adjusted life years (DALYS), or 2.0% of total DALYS. A 10% reduction in serum cholesterol in men aged 40 has been reported to result in a 50% reduction in heart disease within 5 years; the same serum cholesterol reduction for men aged 70 years can result in an average 20% reduction in heart disease occurrence in the next 5 years. In 2008, the global prevalence of raised total cholesterol among adults (≥5.0 mmol/l) was 39% (37% for males and 40% for females). Globally, mean total cholesterol changed little between 1980 and 2008, falling by less than 0.1 mmol/L per decade in men and women. The prevalence of elevated total cholesterol was highest in the WHO Region of Europe (54% for both sexes), followed by the WHO Region of the Americas (48% for both sexes). The WHO African Region and the WHO South East Asian Region showed the lowest percentages (22.6% for AFR and 29.0% for SEAR).

Lactic acid bacteria (LAB) are a genetically diverse group of bacteria that by definition, ferment sugars predominantly to lactic acid. LAB strains are naturally present in environments rich in organic matter, such as food and dairy products and in the mammalian digestive tract. LAB strains are also widely added as starter cultures in the dairy industry and have a long history of safe use, with most being generally recognised as safe (GRAS) or having the Quality Presumption of Safety (QPS) status, according to Federal Department of Agriculture (FDA) and European Food Safety Authority (EFSA), respectively. Some commercial LAB strains and many other microorganisms have been reported to produce exopolysaccharides (EPS). The biological function of EPS is known to be diverse, and includes a contribution to cell protection and survival, protection against environmental stresses, cell adherence, and it plays a role in pathogenesis and symbiosis. EPS can also be advantageous during dairy and non-dairy food fermentation and are used in the food industry as biothickening ingredients. The presence of EPS improves texture, decreases the risk of syneresis and improves techno-functional properties of dairy products. Some EPS-producing LAB strains are reported to spoil beverages, such as wine and cider with an undesired ropiness, down-grading the quality of the products.

In recent years, health benefits have been described for bacterial EPS. For example, EPS produced by commensal gut microorganisms have been demonstrated to play a role in the immune system through communication with the mammalian host. EPS was shown to modulate the gut microbial population, while other EPS-producing LAB strains were demonstrated to exert potential health benefits such as anti-tumoral, antiulcer, and immunostimulatory properties. Furthermore, dietary EPS have been reported to reduce blood pressure and exhibit cholesterol-lowering activities, and ingestion of EPS have been reported to exhibit immunogenic effects, gastrointestinal health and anti-carcinogenic effects.

Cholesterol-lowering properties of EPS and EPS-producing microorganisms have been studied in vivo and in vitro. EPS isolated from *Lactococcus lactis* subsp. *cremoris* SBT 0495 was reported to enhance the metabolism of serum cholesterol in rats. Animals fed kefiran, an EPS produced by *Lb. kefiranofaciens*, reduced total cholesterol in serum and reduced low-density lipoprotein (LDL)-cholesterol concentrations in the liver of animals fed kefiran. Another study demonstrated a reduction in total cholesterol in the liver of cholesterol-fed hamsters when fed milk kefir. Intake of kefiran, the EPS produced by microorganisms present in kefir grains, also greatly reduced the size of atherosclerotic lesions in cholesterol-fed rabbits. It has been suggested that EPS produced by LAB interact with cholesterol in a manner like dietary fibre.

Currently, there is a lack of information and understanding showing the cholesterol-lowering abilities of in situ produced EPS. It is therefore an object of the present invention to overcome at least one of the above-mentioned problems.

SUMMARY OF THE INVENTION

Broadly, the present invention is based on the discovery of an isolated EPS-producing *Lb. mucosae* DPC 6426 strain which can withstand and survive technological and gastrointestinal stresses when compared to the non-EPS-producing *Lb. mucosae* DPC 6420 strain; can typically act as a probiotic; can suitably improve lipid metabolism in the apoE-deficient mouse, an animal model of lipid-driven atherosclerosis fed a high fat, hypercholesterolemic diet, compared with a placebo control (15% (w/v) trehalose); and when used as an adjunct culture, can ideally influence the quality characteristics and sensory and textural properties of low fat set-type yoghurt compared with control yoghurt manufactured without adjunct culture.

According to the present invention, there is provided, as set out in the appended claims, an isolated *Lactobacillus mucosae* DPC 6426 strain as deposited under the terms of the Budapest Treaty on the International Recognition of the Deposit of Microorganisms for the Purpose of Patent Procedure with the National Collection of Industrial and Marine Bacteria Ltd. (NCIMB; Ferguson Building, Craibstone Estate, Blackburn, Aberdeen AB21 9YA UK) under the Accession No. NCIMB 42015 on 23 Jul. 2012 (deposited in the name of Teagasc, Moorepark Food Research Centre, Fermoy, Co. Cork, Ireland), and variants thereof, wherein the variants are characterised in that they are isolated, they belong to the species *Lactobacillus mucosae*, and they express an EPS, typically the same EPS as expressed by *Lactobacillus mucosae* DPC 6426 (characterised below) or an EPS characterised in that it is comprised of monosaccharide residues xylose, fucose, mannose, glucose, galactose, N-acetylglucosamine, and N-acetylmannosamine in the following ratios: 1.1-1.4:0.4-0.6:9.0-10.0:4.7-4.9: 3.2.3.4:1.4-1.6:0.1-0.3, for example approximately 1.3:0.5: 10.0:4.8:3.3:1.5:0.2. Preferably, the variant is further characterised in that it has cardioprotective properties on a subject when administered to the subject, typically by dietary administration. The isolated *Lactobacillus mucosae* DPC 6426 strain as deposited with the National Collection of Industrial and Marine Bacteria under the Accession No. NCIMB 42015 on 23 Jul. 2012 (deposited in the name of Teagasc, Moorepark Food Research Centre, Fermoy, Co. Cork, Ireland) will hereafter be referred to as "isolated strain of the invention", and the variants thereof are hereafter to as "variants".

A significant technological hurdle for probiotic cultures is their successful survival in large numbers during gastric transit so that they are available in the large intestine in high numbers ($10^6$ viable microorganisms per gram or per milliliter) to be beneficial for the host. It was demonstrated that in situ produced EPS by *Lb. mucosae* DPC 6426 significantly increased survival of the strain under salt, bile, simulated gastric juice, acid and elevated heat conditions. Technological and biological robustness of *Lb. mucosae* DPC 6426 implicated its potential use as a probiotic culture. Naturally produced EPS of the strain may offer a selective advantage in performance, stability and persistence over non-EPS-producing strains. Bifidogenic growth enhancement of isolated EPS indicated its use as a prebiotic polymer.

Following dietary treatment with EPS-producing *Lactobacillus mucosae* DPC 6426 in an animal model of lipid-driven atherosclerosis fed a high fat hypercholesterolemic diet, a cardio-protective beneficial effect of the dietary intervention is demonstrated. In particular, significantly reduced ($p \leq 0.001$) serum concentrations of sVCAM-1, significantly reduced ($p \leq 0.001$) total serum cholesterol and serum triglyceride levels ($p \leq 0.05$) were found as a result of dietary intervention with EPS-producing *Lactobacillus mucosae* DPC 6426. A significantly higher ($p \leq 0.05$) ratio of high density lipoprotein (HDL)-cholesterol to total cholesterol was found in the liver; while significantly increased ($p \leq 0.001$) faecal cholesterol excretion were associated with daily administration of EPS-producing *Lb. mucosae* DPC 6426.

The in situ production of EPS resulted in yoghurt with improved textural/rheological qualities, without negatively influencing the performance of the yoghurt starter culture CH-1 during manufacture. Furthermore, the EPS-containing yoghurt was of a higher quality throughout storage compared with the non-EPS control yoghurt. Syneresis, an important factor in consumer acceptance of yoghurt was significantly lower in the EPS-containing yoghurt compared with non-EPS control yoghurt throughout storage for 28 days at 4° C. The improved viscosity of the EPS-containing yoghurt suggests that the EPS produced by *Lb. mucosae* DPC 6426 was an effective viscosifier enhancing yoghurt texture. The viability of *Lb. mucosae* DPC 6426 was stable in yoghurt throughout storage, indicating that yoghurt is a useful food vehicle for efficient delivery of *Lb. mucosae* DPC 6426 and EPS to the human gastric intestinal tract.

The invention also relates to an exopolysaccharide (EPS) obtainable from the isolated strain, or variants thereof, of the invention. Methods of obtaining EPS from the isolated strains and variants thereof are described in more detail below. Typically, the EPS is characterised in that it is comprised (or consists essentially) of monosaccharide residues xylose, fucose, mannose, glucose, galactose, N-acetylglucosamine, and N-acetylmannosamine, preferably in the approximate following ratios: 1.3:0.5:10.0:4.8:3.3:1.5:0.2. Suitably, the EPS has a generalised structure as shown in FIG. 4. Preferably, the major sugar residues present are Man:Glc:Gal in an approximate ratio of 10:4:3. Ratios are provided as % wt ratio's.

The invention also relates to an isolated exopolysaccharide (EPS) characterised in that it is comprised (or consists essentially) of monosaccharide residues xylose, fucose, mannose, glucose, galactose, N-acetylglucosamine, and N-acetylmannosamine, preferably in the approximate following ratios: 1.3:0.5:10.0:4.8:3.3:1.5:0.2. Suitably, the EPS has a generalised structure as shown in FIG. 4. Preferably, the major sugar residues present are Man:Glc:Gal in an approximate ratio of 10:4:3. Ratios are provided as % wt ratios.

The invention also provides an exopolysaccharide of the invention is a substantially pure form (for example, at least 90%, 91%, 92%, 93%, 94%, 95%, 96%, 97%, 98% or 99% purity).

The invention also relates to a formulation comprising an isolated strain of the invention, an exopolysaccharide of the invention, or a variant strain of the invention.

Suitably, the formulation is a pharmaceutical formulation and additionally comprises a pharmaceutically acceptable carrier. Alternatively, the formulation may be a comestible product, for example a food product. Ideally, the food product is a fermented food, for example a fermented dairy product such as a yoghurt. In another embodiment, the formulation may be a starter culture that optionally comprises additional strains of bacteria.

The invention also relates to an isolated strain of the invention, or a variant strain of the invention, or an EPS of the invention, for use in the treatment or prevention of cardiovascular disease, for example atherosclerosis, in a mammal, for example a human. Suitably, the EPS of the invention has a greater cholesterol lowering effect in-vivo than known *Lactobacillus*-derived EPS molecules (as determined using the cholesterol lowering measurement techniques described below).

The invention also relates to an isolated strain of the invention, or a variant strain of the invention, for use as a probiotic culture.

The invention also relates to an isolated strain of the invention, or a variant strain of the invention, for use in the manufacture of fermented dairy product, for example yoghurt, in which the isolated strain or the variant thereof is optionally used a starter culture.

The invention also relates to an EPS of the invention for use in the manufacture of a fermented dairy product, for example yoghurt, The invention also relates to an isolated strain of the invention, or a variant strain of the invention, or an EPS of the invention, for use as a cardio-protective agent. The invention also relates to an isolated strain of the invention, or a variant strain of the invention, or an EPS of the invention, for use in: reducing serum concentrations of sVCAM-1; reducing total serum cholesterol and/or serum triglyceride levels; increasing the ratio of high density lipoprotein (HDL)-cholesterol to total cholesterol in the liver; and/or increasing faecal cholesterol excretion.

The invention also relates to an EPS producing strain of *Lb. mucosae.*

Definitions

In the specification, the term "isolated" should be considered to mean material removed from its original environment in which it naturally occurs, for example, in this instance a bacterial strain of the mammalian gut. The removed material is typically cultivated, purified and cultured separately from the environment in which it was located. Thus, the purified isolated bacterial strain in this instance ideally does not contain any significant amounts of other bacterial strains. The isolated strain or variant of the invention may be provided in a viable or non-viable form, and in a culturable or non-culturable form. The invention also relates to an isolated strain of the invention, or variant thereof, of an exopolysaccharide of the invention, in any format, for example a freeze-dried form, a suspension, a powder, or a broth.

The term "variant" should be understood to mean a strain of bacteria that can be distinguished from the isolated strain of the invention, either in terms of a genetic or phenotypic trait, and which is characterised by being isolated from its natural environment, belonging to the species *Lactobacillus mucosae*, and expressing an exopolysaccharide that is substantially the same as the EPS of the invention. The term "variant" is intended to encompass isolated strains of the invention that have been genetically modified, for example to strains that are engineered to express an exogenous gene, or strains that are engineered to silence an endogenous gene. The term is also intended to encompass variant strains obtained by serial passage of the isolated strain of the invention.

"Treating" (or "treat") as used herein includes its generally accepted meaning which encompasses prohibiting, preventing, restraining, and slowing, stopping or reversing progression, severity, of a cause or resultant symptom of cardiovascular diseases. The term includes causal or symptomatic treatment. As such, the methods of this invention encompass both therapeutic and prophylactic administration.

In this specification, the term "prevention" should be taken to mean inhibition or prevention of the cardiovascular diseases.

In the specification, the term "cardiovascular disease" should be understood to mean a class of diseases that involve the heart and/or blood vessels (i.e. the veins and arteries), and in particular to those diseases associated with atherosclerosis, angina, aneurysm, cerebrovascular accident, cerebrovascular disease, congestive heart failure, coronary artery disease, myocardial infarction, and peripheral vascular disease.

The term "cardio-protective properties" should be understood that the isolated strain of the invention or variant provides a measure of protection to the heart or vasculature of a subject (who has been administered the isolated strain or variant) from damage caused by vascular disease, including but not restricted to atherosclerosis, peripheral vascular disease, pulmonary vascular disease, occlusive vascular disease, restenosis, and coronary heart disease. In particular, the term should be understood to mean causing one or more of: significantly reduced ($p \leq 0.001$) serum concentrations of sVCAM-1; significantly reduced ($p \leq 0.001$) total serum cholesterol and/or serum triglyceride levels ($p \leq 0.05$); significantly higher ($p \leq 0.05$) ratio of high density lipoprotein (HDL)-cholesterol to total cholesterol in the liver; and significantly increased ($p \leq 0.001$) faecal cholesterol excretion.

The term "EPS" or "exopolysaccharide" should be understood to mean high molecular weight polymers that are composed of sugar residues and expressed by bacteria. The exopolysaccharide of the invention may be obtained from the isolated strain of the invention, and is typically further characterised in that it is comprised (or consists essentially) of monosaccharide residues xylose, fucose, mannose, glucose, galactose, N-acetylglucosamine, and N-acetylmannosamine, preferably in the approximate following ratios: 1.3:0.5:10.0:4.8:3.3:1.5:0.2. The EPS of the invention has typically been found to significantly increase the survival of the producing strain under salt, bile, simulated gastric juice, acid and elevated heat conditions. Further, the EPS of the invention has suitably been found to confer improved textural/rheological qualities on food products, especially fermented dairy products, especially yoghurt products. In the case of yoghurt, the EPS of the invention was typically found to cause a decrease in syneresis, and improved viscosity. Thus, as indicated above, in one aspect, the invention relates to the use of the EPS of the invention as a food ingredient, typically an ingredient in dairy products such as yoghurts.

The term "freeze-dried form" should be understood to mean that the strain of the invention, optionally together with other ingredients including, for example, preservatives, is frozen and then the ice crystals in the frozen strain are sublimated under vacuum.

In the specification, the term "mammal" or "individual" as employed herein should be taken to mean a human; however it should also include higher mammals for which the prophylaxis, therapy or use of the invention is practicable.

In this specification, the term "administering" should be taken to include any form of delivery that is capable of delivering the bacterial strain to a site of infection, including local delivery, intravenous delivery, oral delivery, intranasal delivery, intramuscular delivery, intrathecal delivery, transdermal delivery, inhaled delivery and topical delivery. Methods for achieving these means of delivery will be well known to those skilled in the art of drug delivery. For treatment or prophylaxis of lung infections, especially chronic *P. aeruginosa* infections in patients with compromised lung function, such as CF patients, pulmonary delivery is ideal as it delivers the bacterial strain of the invention directly to the small airways of the lung where the target bacteria mucoid infections exist.

In this specification, the term "pharmaceutical composition" should be taken to mean compositions comprising a therapeutically effective amount of a bacterial strain, and a pharmaceutically acceptable carrier or diluent. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the bacterial strain is administered. Such pharmaceutical carriers can be sterile liquids, such as water and oils, including those of petroleum, animal, vegetable or synthetic origin, such as peanut oil, soybean oil, mineral oil, sesame oil and the like.

Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

"Effective amount" refers to the amount or dose of the bacterial strain, upon single or multiple dose administration to the patient, which provides the desired effect in the patient under treatment. An effective amount can be readily determined by the attending diagnostician, as one skilled in the art, by the use of known techniques and by observing results obtained under analogous circumstances. In determining the effective amount or dose of bacterial strain administered, a number of factors are considered by the attending diagnostician, including, but not limited to: the species of mammal; its size, age, and general health; the specific disease involved; the degree of or involvement or the severity of the disease; the response of the individual patient; the mode of administration; the bioavailabilty characteristics of the preparation administered; the dose regimen selected; the use of concomitant medication; and other relevant circumstances.

The term "food product" should be understood to include comestible products, such as foods and drinks. In particular, the food product is a dairy product, especially a fermented dairy product such as a yoghurt.

BRIEF DESCRIPTION OF THE DRAWINGS

The invention will be more clearly understood from the following description of an embodiment thereof, given by way of example only, with reference to the accompanying drawings, in which:—

FIGS. 7A and 7B illustrate an HSQC 2D NMR analysis of EPS from *Lactobacillus mucosae* DPC 6426. Proton NMR spectra signals showed five types of anomeric protons for the EPS isolated from *Lb. mucosae* DPC 6426 at 4.4-5.4 ppm (FIG. 7A). The major anomeric signals, B and C, showed proton and 13C shifts similar to alpha-1,2-mannosyl residues. Signal E at 4.47 ppm and 103 ppm was due to a beta-anomer, and A at 5.25 ppm and 101 ppm to an alpha-anomer. Signal D was due to the fucose anomeric signals. The fucose residues were also evident from the coupled signals at 1.3 ppm and 17 ppm in the full spectra (FIG. 7B).

DETAILED DESCRIPTION

Figure 1:
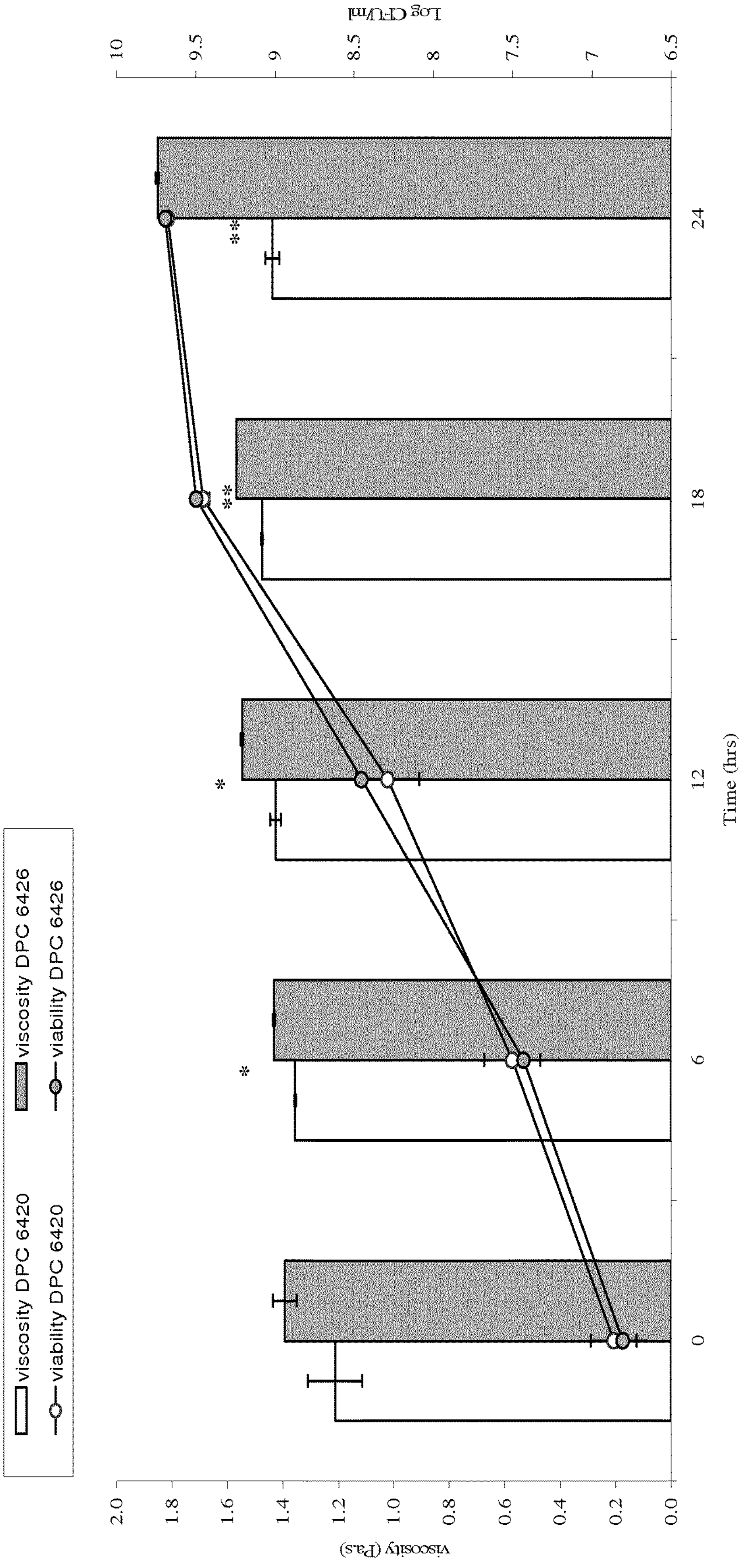
FIG. 1 is a bar chart illustrating the viscosity analysis (bars) and growth curve (circles) of *Lb. mucosae* DPC 6420 (non-EPS-producer) and *Lb. mucosae* DPC 6426 (EPS-producer) following growth anaerobically at 37° C. in MRS broth supplemented with 7% (w/v) glucose. Error bars represent standard errors of the means from 10 readings for each time point (viscosity) and standard errors of the means from triplicate experiments (growth curves). An asterisk denotes a significant difference in viscosity between *Lb. mucosae* DPC 6420 (non-EPS-producer) and *Lb. mucosae* DPC 6426 (EPS-producer). (* $p \leq 0.05$, ** $p \leq 0.01$). A significant increase ($p \leq 0.05$) in viscosity of the fermentation medium was found for isolate DPC 6426 after 6 h of fermentation and throughout the experiment (up to 24 h of incubation: $p \leq 0.01$) compared with non-EPS-producing *Lb. mucosae* DPC 6420. The viscosity of the fermentation medium gradually increased during fermentation for 24 h and the maximum viscosity of fermentation medium for isolate DPC 6426 was found after 24 h of fermentation.
Figure 2:
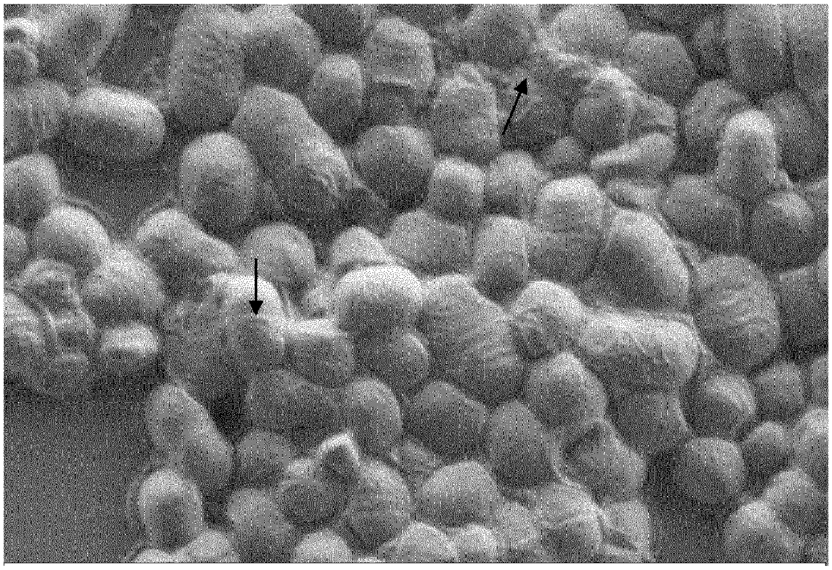
FIG. 2 illustrates a scanning electron microscopy images (1 μm) of EPS-producing *Lb. mucosae* DPC 6426 (A) and non-EPS-producing *Lb. mucosae* DPC 6420 (B) after growth on MRS agar supplemented with 7% (w/v) glucose. Arrows indicate putative EPS production. On SEM micrographs, putative EPS aggregates appeared as web like structures between single cells of *Lb. mucosae* DPC 6426 (FIG. 2 A). In contrast, no such structures were found for the non-EPS-producing strain *Lb. mucosae* DPC 6420 (FIG. 2 B). In this respect, cells appeared without any linkage structures between single cells and overall looked smoother.
Figure 2:
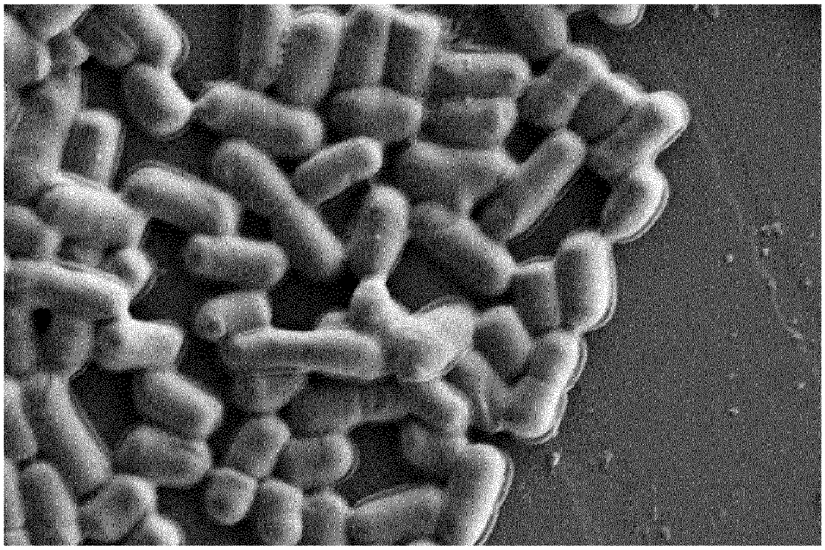
Figure 3:
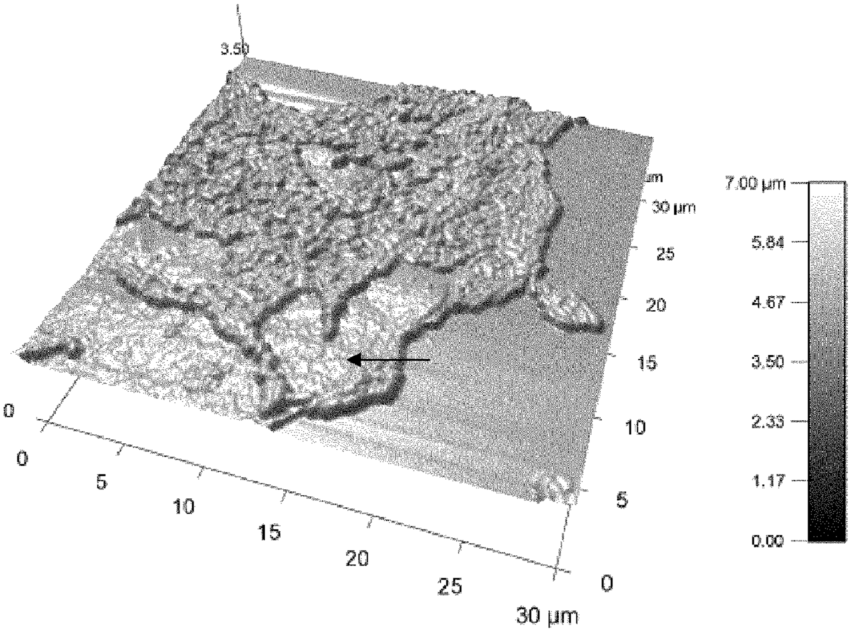
FIG. 3 illustrates atomic force microscopy images of EPS-producing Lb. *mucosae* DPC 6426 (A; 30 μm) and non-EPS-producing *Lb. mucosae* DPC 6420 (C; 10 μm) after growth on MRS agar supplemented with 7% (w/v) glucose. Arrows indicate putative EPS production. On AFM micrographs, the putative EPS aggregates appeared as phase separated uneven masses within the cell aggregates of *Lb. mucosae* DPC 6426 (FIG. 3 A). Again, in contrast, no such aggregates were found on the micrograph for the non-EPS-producing strain *Lb. mucosae* DPC 6420 (FIG. 3B). All AFM images are presented in third dimension.
Figure 3:
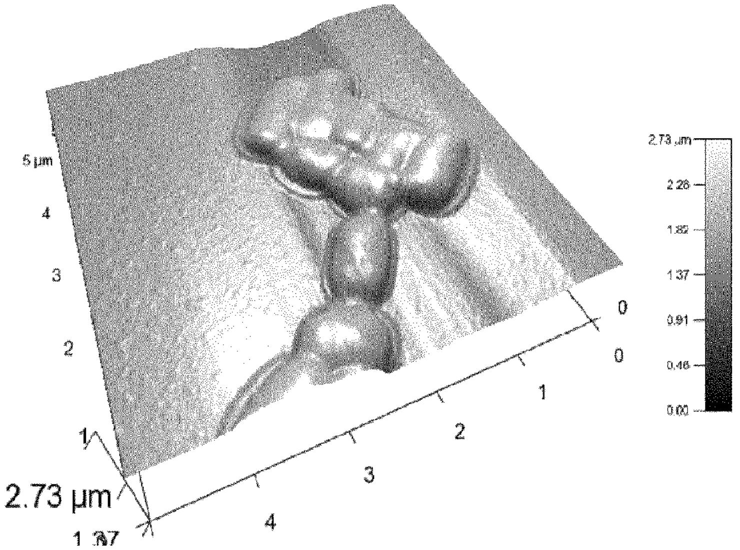
Figure 4:
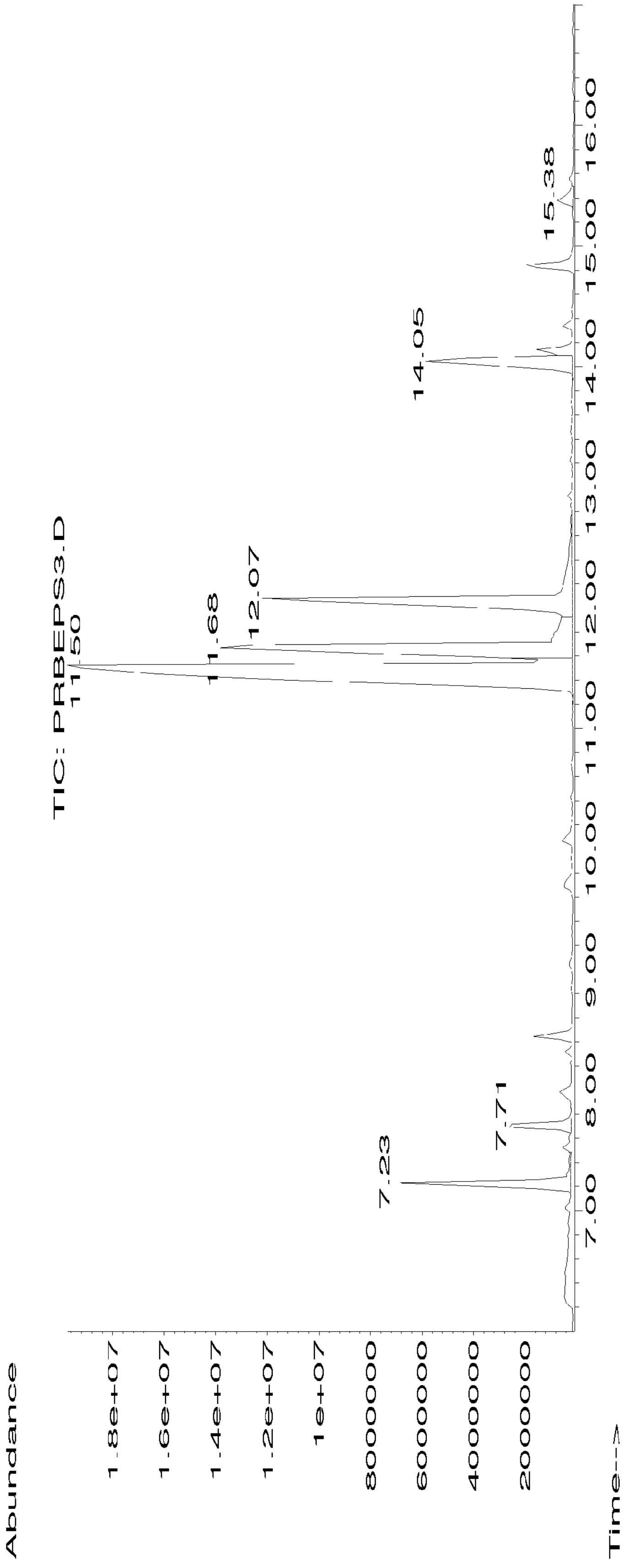
FIG. 4 illustrates a GC MS chromatogram of EPS isolated from *Lb. mucosae* DPC 6426 after sample was refluxed in 2N TFA and converted into pre-acetylated aldononitrile acetates. Compositional analysis of isolated from *Lb. mucosae* DPC 6426 indicated that it is comprised of seven monosaccharide residues: xylose, fucose, mannose, glucose, galactose, N-acetylglucosamine, and N-acetylmannosamine. The seven monosaccharides are presented in the following ratios: 1.3:0.5:10.0:4.8:3.3:1.5:0.2. These results also suggest a considerable structural complexity. Major sugar residues present are Man:Glc:Gal in an approximate ratio of 10:4:3, with mannose comprising about 50% of total sugars. The Xyl:Fuc ratio is 3:2.
Figure 5:
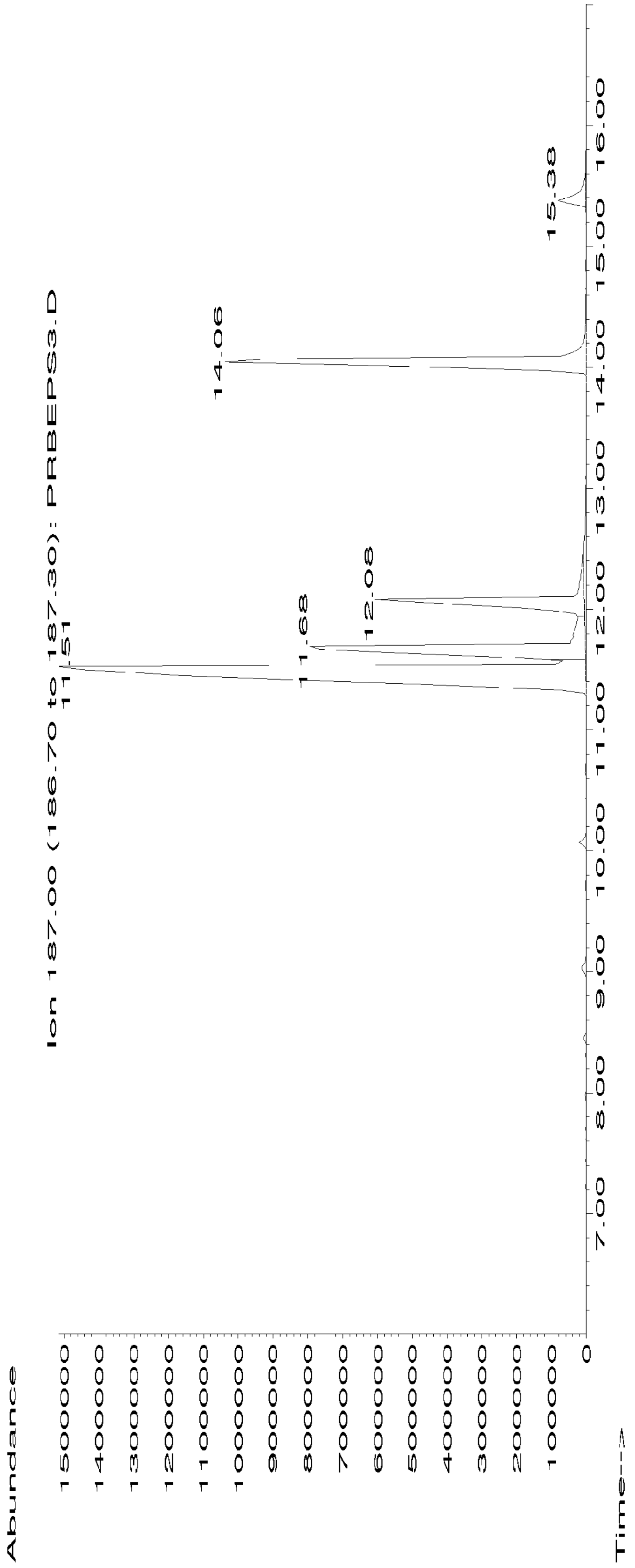
FIG. 5 illustrates an ion extraction m/z 187 chromatogram of EPS isolated from *Lb. mucosae* DPC 6426 after sample was refluxed in 2N TFA and converted into pre-acetylated aldononitrile acetates.

The invention broadly relates to a bacterial strain, *Lactobacillus mucosae* DPC 6420, that has been found to express an exopolysaccharide and have cardio-protective properties on a subject when the subject is administered the strain. The bacterial strain was deposited at the National Collection of Industrial and Marine Bacteria Limited (NCIMB) on 27 Jul. 2012 under NCIMB Deposit Accession No. 42015 by Teagasc, Moorepark Food Research Centre, Fermoy, Co. Cork, Ireland. The invention also relates to the isolated strain of the invention in a viable and non-viable form. The term "viable" should be understood to mean that the bacteria are alive. Viable bacteria may be culturable or non-culturable. The term "non-viable" should be understood to mean that the bacteria are not alive. The invention also relates to an isolated strain of the invention, or a variant thereof, in a freeze-dried form, in the form of a suspension, in the form of a powder, and in the form of a broth obtained through fermentation of the strain. The invention also relates to an isolated exopolysaccharide that is characterised by one or more of the following features: it is obtainable from the isolated strain of the invention or a variant thereof; it is comprised (or consists essentially) of monosaccharide residues xylose, fucose, mannose, glucose, galactose, N-acetylglucosamine, and N-acetylmannosamine, preferably in the approximate following ratios: 1.3:0.5:10.0:4.8:3.3:1.5:0.2; it significantly increases the survival of the producing strain under salt, bile, simulated gastric juice, acid; it confers improved textural/rheological qualities on food products, especially fermented dairy products, especially yoghurt products; and in the case of yoghurt, the EPS of the invention was found to cause a decrease in syneresis, and improved viscosity. The invention also relates to a formulation comprising an isolated strain of the invention in combination with one or more bacterial strains, for example a starter bacteria strain or a probiotic strain. The invention also relates to an exopolysaccharide (EPS) that is characterised in that it is expressed by bacteria, preferably a bacteria that commonly resides in the mammalian gut, and more preferably a bacteria that commonly resides in the human gut, more preferably a *Lactobacillus* bacteria such as *Lactobacillus mucosae* and wherein the EPS confers cardio-protective properties on a subject when the subject is administered the EPS or a bacteria that expresses the EPS. Typically, the EPS, or bacteria that expresses the EPS, is administered via a dietary route.

Material and Methods

Reference Strain and Culture Conditions

*Pediococcus damnosus* 2.6 was used as a reference strain for EPS production. The strain was routinely propagated in deMan Rogosa Sharpe (MRS) medium (Difco Laboratories, Detroit, Mich., USA) at 30° C. under anaerobic conditions. Where necessary, media was solidified with 1.5% (w/v) agar. Stock cultures of the strain were stored at −80° C. in growth medium with 50% (v/v) glycerol before use. *Lactobacillus mucosae* DPC 6420, a non-EPS-producing strain, originally isolated from bovine faeces at Teagasc, Moorepark Food Research Centre (MFRC), Fermoy, Ireland was selected as a negative control for analysis. The strain was routinely cultured in MRS medium (Difco Laboratories, Detroit, Mich., USA) and anaerobic incubated at 37° C.

Screening and Phenotypic Analysis of EPS Producinglactic Acid Bacteria

In a primary screen lactobacilli were screened on *Lactobacillus* Selective agar (LBS) (Difco Laboratories, Detroit, Mich., USA) containing 10% (w/v) glucose (Sigma-Aldrich, Wicklow, Ireland) following anaerobic incubation at 37° C. for 72 h. 5,900 colonies were screened for EPS-producing phenotypes using the loop touch test (Ruas-Madiedo & de los Reyes-Gavilan, 2005). Following the initial screening procedure, 8 putative *Lactobacillus* colonies from infant stool samples and mammalian intestine as part of the DPC collection exhibited a ropy phenotype and streaked on appropriate solid medium containing 10% (w/v) glucose (Sigma-Aldrich, Wicklow, Ireland) and anaerobic incubated at 37° C. for 3 d. Subsequently in a secondary screen, phenotypic analyses were undertaken after replica-plating ropy colonies onto appropriate agar supplemented with 5% (w/v) glucose (Sigma-Aldrich, Wicklow, Ireland) and incubated anaerobically for 72 h at 37° C. Colonies that exhibited a ropy phenotype were tested in liquid broths using the loop touch test. Selected ropy colonies were then grown overnight in the appropriate medium and stocked in 50% (v/v) glycerol at −20° C.

Classification and Identification of EPS Producing Strains

Selected colonies were used for partially sequencing 16s ribosomal RNA (rRNA) genes. Total genomic DNA was isolated and subsequently analysed by PCR reactions. Oligonucleotide primers were synthesised by Sigma-Genosys Biotechnologies, and Taq DNA polymerase (Biotaq; Bioline, London, UK) was used for PCR reactions. The amplification of the 16S rRNA gene was carried out using CO1 (SEQ ID NO. 1: 5' AGTTTGATCCTGGCTCAG3') and CO2 (SEQ ID NO. 2: 5' TACCTTGTTACGACTT3') primers, which enabled the amplification of ~1500 bp fragment. PCR products were purified using QIAquick PCR purification kit (Qiagen, GmbH, Germany) and sequencing was performed by Cogenics™ (Takeley, UK). DNA sequence analysis and similarity searches were performed using the BLAST network service at the National Centre for Biotechnology Information (http://www.ncib.nlm.nih.gov/).

Colony morphology of the selected colonies was performed after incubation on MRS (Difco Laboratories, Detroit, Mich., USA) agar at 37° C. for 48 h. Cell morphology was examined microscopally (Olympus BX 51; magnification, ×1000) after incubation in MRS (Difco Laboratories, Detroit, Mich., USA) broth at 37° C. for 24 h. Gram reaction and catalase-activity using 2% (v/v) $H_2O_2$ on single colonies after 2 d and 5 d incubation at 30° C. and 45° C. were investigated. The pH of growth medium was monitored as an indicator of growth. Gas production (hetero-fermentation) from glucose was determined after anaerobic incubation at 37° C. for 2, 5 and 7 d.

Sugar Fermentation

Sugar fermentation patterns were determined using API 50CH stripes and API 50CHL medium (BioMérieux, Marcy l'Etoile, France). Tested strains were grown anaerobically in appropriate medium at 37° C. for 24 h before inoculation and the API stripes were read after 24 h and 48 h incubation at 37° C. anerobically.

Phenotypic Analysis

The viscosity in broths of selected strains was analysed during growth in appropriate medium at 37° C. for 24 h. Overnight cultures were inoculated at 2% (v/v) in MRS (Difco Laboratories, Detroit, Mich., USA) medium broth containing 7% (w/v) glucose (Sigma-Aldrich, Wicklow, Ireland) and viscosity readings were taken every 6 h for a 24 h-period using an AR-G2 rheometer (TA instruments, Crawley, UK).

Scanning Electron Microscopy (SEM) and Atomic Force Microscopy (AFM)

For scanning electron and atomic force microscopy (SEM and AFM) respectively, selected strains and non-EPS-producing *Lb. mucosae* DPC 6420 were grown on MRS (Difco Laboratories, Detroit, Mich., USA) agar supplemented with 7% (w/v) glucose (Sigma-Aldrich, Wicklow, Ireland) at 37° C. anaerobically for 72 h and subsequently processed for microscopy analysis. For SEM analysis, one colony was picked and gently smeared on mica which was attached to a stab using double sided sticky disc. Analyses were performed on Zeiss Supra 40VP field emission SEM with high vacuum at 2 kV and working distance between 5.4 mm and 6.6 mm. For AFM analysis, one colony was picked and placed on freshly cleaved mica. To emerge the colony, 100 μl sterile deionised water was added on the mica and left to dry for 24 h. AFM settings were used as described by Oboroceanu et al. (2010).

Characterisation of Microbial EPS

Strains were inoculated in MRS (Difco Laboratories, Detroit, Mich., USA) broth with 5% (w/v) glucose (Sigma-Aldrich, Wicklow, Ireland). Following anaerobic incubation at 37° C. for 48 h, the pH of the samples was adjusted to pH 6.2 with 4M NaOH followed by overnight hydrolysis using 0.2 mg/ml proteinase K (Sigma-Aldrich, Wicklow, Ireland) at 37° C. To terminate the reaction, the mixture was heated at 90° C. for 10 min and centrifuged at 4,000×g for 30 min (Sorvall®LegendRT, Thermo Scientific, Loughborough, UK). The supernatant was collected and precipitated with 4 volumes of chilled ethanol and agitated (100 rpm) overnight at 4° C. To recover the precipitate, the mixture was centrifuged at 4,500×g for 30 min. The pellet was dissolved in 10 ml of sterile deionised water and dialyzed (molecular mass cut-off of 12,000 Da) against deionised water for 3 d at 4° C. (with two daily washing steps). The mixture was lyophilized (VirTis AdVantage™ Freeze Dryer, SP Industries, NY, USA) and the generated powder was kept at −20° C. for further analysis.

The colorimetric phenol-sulphuric method was performed to estimate the EPS content with glucose as standard. EPS concentrations were expressed as glucose equivalent. The concentrations of EPS were determined by subtracting the total amount of glucose detected in unfermented culture medium (which was used as a blank) from total amount of glucose detected in the inoculated fermentation medium.

EPS structure characterizations were performed by sugar compositional analysis using gas chromatography mass spectroscopy (GC-MS) analysis. Prior analysis, EPS samples were refluxed in 2N trifluoroacetic acid (TFA) and converted into pre-acetylated aldononitrile acetates (PAANs). For linkage analysis, nuclear magnetic resonance (NMR) spectroscopy was performed.

Bacterial Strains, Growth Conditions and Media

EPS-producing *Lactobacillus mucosae* DPC 6426 (as deposited with the National Collection of Industrial and Marine Bacteria under the Accession No. NCIMB 42015 on 23 Jul. 2012 (deposited in the name of Teagasc, Moorepark Food Research Centre, Fermoy, Co. Cork, Ireland)), non-EPS-producing *Lactobacillus mucosae* DPC 6420, *Bifidobacterium lactis* Bb-12, and *Bifidobacterium breve* NCIMB 8807 were used.

Lactobacilli were routinely cultured in MRS medium (Difco Laboratories, Detroit, Mich., USA) and incubated anaerobically at 37° C. Bifidobacteria were routinely cultured in MRS medium (Difco Laboratories, Detroit, Mich., USA) with the addition of 0.5% (w/v) cysteine (Sigma-Aldrich, Wicklow, Ireland) and incubated anaerobically at 37° C.

Stress Tolerance Assays

All stress assays were performed at 37° C. during incubation unless otherwise stated. Aliquots were taken at selected time points and viable cell counts were enumerated by serial dilution in maximum recovery diluent (MRD; Oxoid, c/o Fannin Healthcare, Dublin, Ireland) and enumerated on MRS (Difco Laboratories, Detroit, Mich., USA) agar plates followed by anaerobic incubation at 37° C. for 48 h. Salt stress assays, bile stress assays, acid stress assays and heat stress assays were all performed on EPS-producing *Lactobacillus mucosae* DPC 6426 and non-EPS-producing *Lactobacillus mucosae* DPC 6420. For salt stress assays, samples were taken every 30 min for 120 min. For bile stress assays, samples were taken every 15 min for 90 min. For acid stress assays, samples were taken every 15 min for 60 min and for simulated gastric juice (pH 2) samples were taken every 5 min for 10 min. For heat stress assays, samples were taken every 15 min for 60 min. One milliliter of overnight cultures of EPS-producing *Lactobacillus mucosae* DPC 6426 and non-EPS-producing *Lactobacillus mucosae* DPC 6420 were centrifuged (13,000×g for 5 min) and the pellets were resuspended in 1 ml MRS (Difco Laboratories, Detroit, Mich., USA) containing 5M NaCl and incubated at 37° C. for 120 min for salt stress assays. The pellets were resuspended in 1 ml of simulated gastric juice (pH 2) and incubated at 37° C. for 10 min or in 1 ml MRS (Difco Laboratories, Detroit, Mich., USA) which had been adjusted to pH 2 with 1M HCl and incubated at 37° C. for 60 min for the acid stress assays. For the bile stress assays, 3% (v/v) of overnight cultures were inoculated into 10 ml of MRS (Difco Laboratories, Detroit, Mich., USA) containing 0.7% (w/v) porcine bile (Sigma-Aldrich, Wicklow, Ireland) and incubated at 37° C. for 90 min. For the heat stress assays, 1 ml of overnight cultures were centrifuged (13,000×g for 5 min) and the pellets were resuspended in 1 ml of preheated (55° C.) MRS (Difco Laboratories, Detroit, Mich., USA) broths and incubated at 55° C. for 60 min.

Bifidogenic Effect of EPS Isolated from *Lb. mucosae* DPC 6426

The prebiotic bioassay was performed as previously outlined (Brewster 2003; Wagner, et al., 2003) using purified EPS from *Lb. mucosae* DPC 6426. The EPS was isolated of *Lb. mucosae* DPC 6426 after anaerobic incubation at 37° C. for 3 days in MRS (Difco Laboratories, Detroit, Mich., USA) supplemented with 5% (w/v) glucose (Sigma-Aldrich, Wicklow, Ireland) as described by Martensson, et al. (2002) with modification as follows. Briefly, after fermentation, samples were adjusted to pH 6.2 using 1M NaOH. Proteins were hydrolysed with 6 units/ml proteinase K (Sigma- Aldrich, Wicklow, Ireland) and incubated at 37° C. overnight. The enzymatic reaction was terminated by heat treating the sample at 90° C. for 10 min. The samples were then cooled to room temperature and centrifuged at 4000×g for 30 min (Sorvall®LegendRT, Thermo Scientific, Loughborough, UK). The supernatant was collected and precipitated with 4 volumes of ice-cold ethanol followed by storage overnight at 4° C. The precipitate was collected by centrifugation at 4000×g for 30 min at 4° C. (Sorvall®LegendRT, Thermo Scientific, Loughborough, UK), dissolved in sterile deionised water and dialyzed (molecular mass cutoff of 12,000 Da) against deionised water for 3 days at 4° C. Samples were lyophilized (VirTis AdVantage™ Freeze Dryer, SP Industries, NY, USA) and stored at −20° C. until the bifidogenic bioassays were performed. Lyophilized EPS was added to Trypticase-Peptone-Yeast extract (TPY) medium at a concentration of 0.2% (w/v) as the sole carbohydrate source. *B. lactis* Bb-12 and *B. breve* NCIMB 8807 were anaerobically grown at 37° C. in MRS broth with the addition of 0.5% (w/v) cysteine until the OD reached 0.5 for the bifidogenic prebiotic bioassays. Bioassays were performed in 96-well plates in a total volume of 200 μl of TPY medium inoculated with 1% (v/v) of each *B. lactis* Bb-12 and *B. breve* NCIMB 8807 (~$10^6$ CFU/ml) in individual wells. Plates were covered with microfilm to create an anaerobic environment and placed in a plate reader for 48 h (Synergy™ HT Multi-Mode Microplate Reader, BioTek Instruments). Microbial growth kinetics was recorded as the OD at 600 nm every 4 h for a total of 48 h on a Synergy-HT multidetector driven by Gen5 reader control and data analysis software (BioTek Instruments, Bedfordshire, UK). Conditions were as follows: Wavelength 600 nm, shaking speed low, shaking duration 5 s, temperature 37° C. and OD reading every 4 h for a total of 48 h. The level of shaking was sufficient to prevent settling of bacteria on the bottom of the well. As a positive control, 1% (v/v) of each *B. lactis* Bb-12 and *B. breve* NCIMB 8807 (~$10^6$ CFU/ml) were inoculated in 200 μl MRS (Difco Laboratories, Detroit, Mich., USA) medium with the addition of 0.5% (w/v) cysteine (Sigma-Aldrich, Wicklow, Ireland) and incubated anaerobically at 37° C. in a plate reader for 48 h (Synergy™ HT Multi-Mode Microplate Reader, BioTek Instruments). Microbial growth kinetics was recorded as the OD at 600 nm every 4 h for a total of 48 h on a Synergy-HT multidetector driven by Gen5 reader control and data analysis software (BioTek Instruments, Bedfordshire, UK). As a negative control, 1% (v/v) of each *B. lactis* Bb-12 and *B. breve* NCIMB 8807 (~$10^6$ CFU/ml) were inoculated in 200 μl TPY medium without the addition of a sole carbohydrate source and incubated anaerobically at 37° C. in a plate reader for 48 h (Synergy™ HT Multi-Mode Microplate Reader, BioTek Instruments). Microbial growth kinetics was recorded as the OD at 600 nm every 4 h for a total of 48 h on a Synergy-HT multidetector driven by Gen5 reader control and data analysis software (BioTek BioTek Instruments, Bedfordshire, UK).

Preparation and Administration of *Lb. mucosae* DPC 6426

Rifampicin-resistant variants of *Lb. mucosae* DPC 6426 were activated and propagated three times in *Lactobacillus* de Man, Rogasa and Sharp medium (MRS; Difco Laboratories, Detroit, Mich., USA) containing 5 μg/ml rifampicin (Sigma-Aldrich, Wicklow, Ireland) at 37° C. anaerobically. Fermentation of *Lb. mucosae* DPC 6426 was undertaken in MRS (Difco Laboratories, Detroit, Mich., USA) broth containing 5% (w/v) sucrose (Sigma-Aldrich, Wicklow, Ireland) at 37° C. anaerobically for 20 h. Following fermentation, the culture was washed twice in phosphate-buffered saline (PBS, Sigma-Aldrich, Wicklow, Ireland) and resuspended in 15% (w/v) trehalose (Sigma-Aldrich, Wicklow, Ireland). Aliquots were freeze-dried (VirTis AdVantage™ Freeze Dryer, SP Industries, NY, USA) with the use of a 24 h program (freeze temperature: −40° C.; condenser set point: −60; vacuum set point: 0.6 mm Hg). For the enumeration of viable *Lb. mucosae* DPC 6426 in freeze-dried powders, one vial of freeze-dried powder was resuspended in 1 ml of sterile deionised water and appropriate serial dilutions were prepared before plating on MRS agar supplemented with 5 μg/ml rifampicin (Sigma-Aldrich, Wicklow, Ireland) and anaerobic incubation at 37° C. for 2-3 d. For the enumeration of viable *Lb. mucosae* DPC 6426 in drinking water for 24 h, one vial of freeze-dried powder was resuspended in 1 ml of sterile deionised water and left for 24 h at room temperature before plating on MRS agar supplemented with 5 μg/ml rifampicin (Sigma-Aldrich, Wicklow, Ireland) and anaerobic incubation at 37° C. for 2-3 d. Individual animals consumed ~$1\times10^9$ live microorganisms per day. This was achieved by resuspending appropriate quantities of freeze-dried powder in the water that mice received ad libitum. The control group received placebo freeze-dried powder (15% trehalose).

Experimental Animals and Diet

All animal studies were undertaken in accordance with the Department of Health and Children of the Irish Government. A license and permission for the study were obtained from the Department of Health, Ireland. Male Apoet$^{m1Unc}$/J mice between 10 and 12 weeks old at the beginning of the experiment were obtained from JAX® (The Jackson Laboratory through Charles River Laboratories International, Kent, UK). Animals were caged either individually, in pairs, or in groups of four to six per cage. Group housing differences were distributed into two different feeding groups. All animals were fed a basal diet (D12450B, Research Diets Inc., NJ, USA through Harlan Laboratories, Blackthorn, UK) ad libitum for two weeks to stabilize all metabolic conditions, with free access to water at all times. The basal diet contained the following nutrient composition: casein, 80 mesh (18.9%), 1-cysteine (0.3%), corn starch (29.8%), maltodextrin 10 (3.3%), sucrose (33.2%), cellulose, BW200 (4.7%), soybean oil (2.4%), lard (1.9%), mineral mix S10026 (0.9%), di-calcium phosphate (1.2%), calcium carbonate (0.5%), potassium citrate, $1H_2O$ (1.6%), vitamin mix V10001 (0.9%) and choline bitartrate (0.2%).

Following the one-week acclimatisation period, animals were divided into two groups (n=9) and received a high fat (60% kcal from fat) hypercholesterolemic diet (2% w/w). The composition of the high fat, high cholesterol diet is given in Table 1. Group A was fed high fat chow diet (60% kcal from fat) which included 2% (w/w) cholesterol and administrated a daily dose of $10^9$ CFU of EPS-producing *Lb. mucosae* DPC 6426 in drinking water for 12 weeks. Group B received a high fat chow diet (60% kcal from fat) which included 2% (w/w) cholesterol and resuspended trehalose in drinking water for 12 weeks. Animals were housed in an isolator station, exposed to a 12-h light/dark cycle and maintained at a constant temperature of 25° C. Body weight and food intake were monitored weekly. After 12 weeks on experimental diets, mice were sacrificed and blood was collected by retro-orbital blood sampling and stored at 4° C. for 30 min, followed by centrifugation at 10,000×g for 5 min, and divided into aliquots and stored at −20° C. until processed. Tissues were removed, blotted dry, weighed, and frozen in liquid nitrogen. All samples were stored at −80° until use.

TABLE 1

Nutritional composition of high fat, hypercholesterolemic diet (60% kcal from fat; 2% (w/w) cholesterol) (TD.110007; Harlan Laboratories, Blackthorn, UK).

| Formula | g/Kg |
|---|---|
| Casein | 265.0 |
| L-Cystine | 4.0 |
| Maltodextrin | 160.0 |
| Sucrose | 90.0 |
| Lard | 310.0 |
| Soybean Oil | 30.0 |
| Cholesterol | 20.0 |
| Cellulose | 45.6 |
| Mineral Mix, AIN-93G-Mix | 48.0 |
| Calcium Phosphate, dibasic | 3.4 |
| Vitamin Mix, AIN-93-VX | 21.0 |
| Choline Bitratrate | 3.0 |

Microbial Analysis

Microbial analysis of freeze-dried powders containing *Lb. mucosae* DPC 6426 and survival of the strain in drinking water for 24 h was undertaken weekly for every batch produced and involved enumeration of the strain on MRS (Difco Laboratories, Detroit, Mich., USA) agar supplemented with 5 μg/ml rifampicin (Sigma-Aldrich, Wicklow, Ireland) following incubation for 72 h at 37° C. anaerobically.

Fresh faecal samples were taken from apoE-deficient mice once weekly and analysed for the presence of rifampicin-resistant EPS-producing *Lb. mucosae* DPC 6426. Microbial analysis of the faecal samples involved enumeration of the strains on MRS (Difco Laboratories, Detroit, Mich., USA) agar supplemented with 5 μg/ml rifampicin (Sigma-Aldrich, Wicklow, Ireland) following incubation for 72 h at 37° C. anaerobically.

Preparation and Analysis of Aortas

Hearts and aortas were removed and fixed in a 4% (w/v) paraformaldehyde (PFA; Sigma-Aldrich, Wicklow, Ireland) solution in phosphate buffered saline (PBS; Sigma-Aldrich, Wicklow, Ireland). After removal of visible adventitial fat, paraformaldehyde (PFA)-fixed aortas were dissected and washed in isopropanol:water (2:1) for 5 min and stained with 0.3% (v/v) Oil Red O (Sigma-Aldrich, Wicklow, Ireland) for 90 min in 24 well plates at room temperature. Initially, a 3% (w/v) solution of Oil Red O in 2-propanol was prepared by heating the reagents to 56° C. for 1 h and then cooling to room temperature. The solution was filtered through a number 1 filter paper (Whatman, through Fisher Scientific Ireland, Dublin), and a 0.3 (v/v) working solution was prepared using 2-propanol as diluent. After two washes with isopropanol:water (2:1) for 2 min, the aortas were transferred to 24-well plates and stored in PBS at 4° C. The aortas were placed onto black silicone plates and cut open starting at the lesser curvature, pinned on the silicone plate and inspected under the microscope for quantification of lipids. Lipid-containing plaque area was determined as percent of Oil Red O-stained area from the total aortic surface area using the AxioVision 4.6/NIH Image J software (Carl Zeiss Vision, Thornwood, N.Y., USA).

Measurement of Serum Soluble Vascular Cell Adhesion Molecule-1 (VCAM-1)

Commercially available murine ELISA kit (Quantikine®, R&D Systems, UK) was used for measuring serum levels of soluble VCAM-1 (sVCAM-1). This assay employs the quantitative sandwich enzyme immunoassay technique, in which a monoclonal antibody specific for mouse sVCAM-1 has been precoated onto a microplate. Standards and samples were pipetted into wells and any mouse sVCAM-1 present was bound by the immobilized antibody. Following a wash to remove any unbound antibody-enzyme reagent, a substrate solution was added to the wells. The enzyme reaction yielded a blue product that turned yellow when a stop solution was added. The intensity of the colour measured was proportional to the amount of mouse sVCAM-1 bound in the initial step. The sample values were read off a standard curve. Samples and standards were analysed in duplicate.

Serum Lipid Analysis

Total serum cholesterol was determined using EnzyChrom™ Cholesterol Assay Kit (ECCH-100, BioAssay Systems, CA, USA). The assay is based on cholesterol esterase hydrolysis of cholesterol esters to form free cholesterol and cholesterol dehydrogenase catalysed conversion of cholesterol to cholest-4-ene-3-one, in which NAD is reduced to NADH. The optical density of the formed NADH at 340 nm is directly proportional to the cholesterol concentration in the serum sample. The sample values were read off a standard curve. Samples and standards were analysed in duplicate.

Determination of HDL cholesterol in serum samples was undertaken using EnzyChrom™ HDL and LDL/VLDL Assay Kit (EHDL-100, BioAssay Systems, CA, USA). The assay is based on polyethylene glycol (PEG) precipitation method, in which HDL and LDL/VLDL are separated, and serum cholesterol concentrations were determined using cholesterol esterase/cholesterol dehydrogenase reagent. In this reaction, NADH at 340 nm is directly proportional to the serum cholesterol concentration. The sample values were read off a standard curve. Samples and standards were analysed in duplicate.

Triglycerides in serum were determined using LabAssay™ Triglyceride Kit (Wako Diagnostics, VA. USA). The assay is based on an enzymatic method using N-ethyl-N-(2-hydroxy-3-sulfopropyl)-3,5-dimethoxyaniline sodium salt as a blue pigment. Triglycerides in serum samples were hydrolysed to glycerol and free fatty acids in a reaction catalysed by lipoprotein lipase. Glycerol was converted to glycerol-3-phosphate by glycerolkinase in the presence of ATP. Glycerol-3-phosphate was oxidised by glycerol-3-phosphate oxidase in a reaction that produces hydrogen peroxide which caused N-ethyl-N-(2-hydroxy-3-sulfopropyl)-3,5-dimethoxyaniline sodium salt and 4-aminoantipyrine to undergo a quantitative oxidative condensation catalysed by peroxidise, producing a blue pigment. The amount of triglycerides in serum samples was determined by measuring the absorbance at 600 nm. The sample values were read off a standard curve. Samples and standards were analysed in duplicate.

Lipid Extraction from Faeces and Liver

Livers and faeces were stored at −80° C. prior to analysis. Liver and faecal lipids were extracted with chloroform: methanol 2:1 (v/v). The extracted fat samples were dried and dissolved in assay buffer. Liver cholesterol, liver triglyceride and faecal cholesterol concentrations were determined using the same kits as used for blood lipid analysis. Extraction of total bile acids from faeces was performed. Briefly, faecal samples were oven dried and 50 mg of faeces were mixed with 1 ml of 50% (v/v) tert-butanol in water. The mixture was incubated at 37° C. for 15 min and then centrifuged at 10,000×g for 2 min at room temperature. The supernatant was dried in a Speedvac and dried samples reconstituted in 1 ml assay buffer (phosphate buffer, EDTA) and total bile acid concentrations were determined using Colorimetric Total Bile Acids Assay Kit (Diazyme Laboratories, CA, USA). The assay is based on an enzymatic reaction, where 3-α hydroxysteroid dehydrogenase converted bile acids to 3-keto steroids and NADH in the presence of NAD. The NADH reacted with nitrotetrazolium blue to form a formazan dye in the presence of diaphorase enzyme. The dye formation was measured at 540 nm and was directly proportional to the bile acid concentration in samples. Samples were analysed in duplicate.

RNA Preparation and Real-Time Fluorescence Monitoring Reverse Transcription-(RT)-PCR Total RNA was extracted from liver samples using QIAGEN RNase mini kit (Qiagen, GmbH, Germany) according to manufacturer's protocol. Total RNA (1 μg) was reverse-transcribed into cDNA using cDNA Synthesis Kit (Bioline Ltd., London, UK) according to manufacturer's instructions. Briefly, to prime RNA, a reaction mix (10 μl) containing 1 μg of RNA, 1 μl Oligo $(dT)_{18}$, and 1 μl 10 mM dNTP was incubated at 65° C. for 10 min. Following this, the reaction mix was placed on ice for 2 min. The primed RNA was then mixed with an enzyme mix (10 μl) containing 4 μl 5×RT buffer, 1 μl RNase inhibitor, and 0.25 μl reverse transcriptase (200 U/μl) and incubated at 37° C. for 60 min. The reaction was terminated by incubation at 70° C. for 15 min and the mixture was placed on ice. To quantify mRNA expression, PCR was performed using a fluorescence temperature cycler (LightCycler System: Roche Diagnostics, Mannheim, Germany). The oligonucleotide primers for β-actin, cholesterol 7α-hydroxylase (CYP7A1) and 3-hydroxy-3-methylglutaryl-coenzyme A (HMG-CoA) reductase were designed based on published nucleotide sequences for named genes in apoE-deficient mice (Han, et al., 2006). Amplification was performed as follows. Briefly, the reaction solution (10 μl final volume: 10 μl) contained 5 μl of LightCycler DNA Master SYBR Green I dye, 0.5 μl of each primer and 1 μl of cDNA. The standard amplification program included 40 cycles of three steps each, which involved heating the product to 95° C. for 30 s, annealing at appropriate temperature for 30 s, and extension at 72° C. for 30 s. Basic relative quantification of expression was determined using the comparative $2^{-\Delta Ct}$.

Starter Microorganisms

Prior to yoghurt manufacture, *Lactobacillus mucosae* DPC 6426 was activated and propagated three times in de Man, Rogasa and Sharp medium (MRS; Difco Laboratories, Detroit, Mich., USA) medium at 37° C., anaerobically. The thermophilic yoghurt starter CH-1 (non-EPS-producing) consisted of a defined mixed single strain cultures *Streptococcus thermophilus* and *Lactobacillus delbrueckii* subsp. *bulgaricus* in a freeze-dried pellet form (Chr. Hansen, Denmark). Before use, the CH-1 cultures were activated by adding a 50 U sachet (consisting of ~$1\times10^6$ CFU/g of *S. thermophilus* and ~$1\times10^8$ CFU/g of *Lb. delbrueckii* subsp. *bulgaricus*) to 500 ml of sterile 14% (w/v) reconstituted medium-heat skim milk (RSM; Kerry Ingredients Ltd., Kerry, Ireland) and agitated for 15 min, in order to achieve a homogenous culture, according to the manufacturer's instructions Growth Behaviour of *Lb. mucosae* DPC 6426 in Yoghurt Base Supplemented with Different Sugar Sources Prior to yoghurt fermentation, *Lactobacillus mucosae* DPC 6426 was grown in yoghurt base supplemented with different sugars. The yoghurt base was prepared by dissolving 10% (w/v) skim milk powder (Kerry Ingredients Ltd., Kerry, Ireland) in deionised water and supplemented with 5% (w/v) glucose (Sigma-Aldrich, Wicklow, Ireland) or 5% (w/v) sucrose (Sigma-Aldrich, Wicklow, Ireland) or no sugar addition. The fermentation substrate was sterilized at 121° C. for 5 min and cooled to the fermentation temperature of 37° C. The yoghurt base was inoculated with *Lb. mucosae* DPC 6426 and incubated at 37° C. for 48 h, anaerobically. Viable cell counts, the pH of the fermentate and titratable acidity were measured after 24 h and 48 h of fermentation.

EPS concentrations were determined at the end of fermentation using the colorimetric phenol-sulphuric method by subtracting the total amount of glucose detected in unfermented culture medium (which was used as a blank) from total amount of glucose detected in the inoculated fermentation medium.

Yoghurt Manufacture

The fermentation substrate consisted of 14% (w/v) RSM (Kerry Ingredients Ltd., Kerry, Ireland) supplemented with 5% (w/v) sucrose (Sigma-Aldrich, Wicklow, Ireland). Prior to inoculation, the fermentation substrate was pasteurised (MicroThermics, Raleigh, N.C., USA) at 95° C. for 5 min and cooled to the fermentation temperature of 37° C. Overnight cultures (20 h) of *Lb. mucosae* DPC 6426 were centrifuged (Sorvall® RC-5B Plus, Thermo Scientific, MA, USA) at 10,000×g for 10 min at 4° C., washed with sterile Mili-Q water and resuspended with an aliquot of the fermentation substrate. In separate aliquots of RSM, representing the control and EPS-containing yoghurts, fermentation substrate was inoculated at 0.2% (v/v) with either the activated CH-1 culture (control) or the activated CH-1 culture in combination with *Lb. mucosae* DPC 6426 and agitated for 10 min to achieve adequate mixing. The samples were distributed into sterile yoghurt cartons (VWR International, Dublin, Ireland) and incubated in an anaerobic gas station (Don Whitley Anaerobic Cabinet MACS 500, Davidson and Hardy, Dublin, Ireland) at 37° C. The fermentation was performed under anaerobic conditions and terminated at pH 4.7. The set-type yoghurts were immediately stored at 4° C. for 28 days. All data are based on triplicate yoghurt trials.

Determination of Culture Viability

Viable cell counts were determined before and after yoghurt fermentation process and after 1, 7, 14, 21 and 28 days of yoghurt storage at 4° C. For selective enumeration of *S. thermophilus*, a dilution series was inoculated onto solidified M17 medium (Difco Laboratories, Detroit, Mich., USA) supplemented with a membrane-filtered sterile solution of 10% (w/v) lactose (Oxoid; 1% (w/v) final lactose concentration) at 42° C. for 48 h, aerobically. Selective enumeration of *Lb. delbrueckii* subsp. *bulgaricus* was performed on MRS (Difco Laboratories, Detroit, Mich., USA) agar with pH adjusted to 5.2 and incubated under anaerobic conditions at 37° C. for 48 h. Selective enumeration of Lb. *mucosae* DPC 6426 was performed on MRS (Difco Laboratories, Detroit, Mich., USA) agar with pH adjusted to 4.6 and anaerobic incubation at 42° C. for 48 h.

Acidifying Kinetics and Post-Acidification

The pH of the fermentation medium was monitored during yoghurt fermentation and storage using a pH meter (model MP220, Mettler-Toledo, Greifsensee, Switzerland), with calibrated electrode (Mettler-Toledo InLab® 413, Mettler-Toledo). The titratable acidity of yoghurt was assessed by adding one drop of phenolphthalein (Sigma-Aldrich, Wicklow, Ireland) to 10 g of yoghurt and titrating with 0.1M NaOH, until a light pink colour developed and persisted. Titratable acidity was expressed as percentage of lactic acid present in the yoghurt. In the present invention, the titratable acidity, expressed as the amount of lactic acid, was not significantly affected (p=0.666) by the presence of the EPS-producing *Lb. mucosae* DPC 6426 at ~$10^9$ CFU/ml in yoghurt.

Extent of Syneresis

The water-holding capacity of the yoghurt product was measured. Briefly, yoghurt samples were stirred 20 times clockwise and anticlockwise and 30 g of samples were stored at 4° C. for 2 h for stabilization, followed by centrifugation at 3,313×g for 15 min at 10° C. Separated whey was weighed and syneresis was expressed as the percentage of whey separated from the gel over the initial weight of the gel.

Texture Measurement

The rheological properties of yoghurt samples were evaluated at the end of fermentation period and during storage using an AR G2 rheometer (TA instruments, Crawley, UK) fitted with a 60-mm aluminium parallel plate measurement system. The measuring geometry had a gap size of 800 micrometers. All measurements were made at 20° C. Samples were initially stirred to achieve a homogenous mixture. Samples were pre-sheared at 200 $s^{-1}$ for 1 min to erase the processing history of the sample, allowed to equilibrate for 1 min, sheared from 0.01 to 200 $s^{-1}$ over 2 min, held at 200 $s^{-1}$ for 1 min and sheared from 200 to 0.01 $s^{-1}$ over 2 min.

Determination of EPS-Concentration

The EPS was isolated according to the method by Amatayakul, et al. (2006). Briefly, yoghurt samples (25 ml) were diluted 1:1 with Milli-Q-water and 4 ml of 20% (w/v) trichloroacetic acid (TCA) solution were added to precipitate protein. The samples were centrifuged at 3,313×g for 30 min at 4° C. to remove precipitated protein and bacterial cells. The supernatant was neutralized to pH 6.8 with 4M NaOH, boiled in a sealed container for 30 min and centrifuged (3,313×g for 30 min at 4° C.) to remove the remaining precipitated insoluble proteins. An equal volume of chilled ethanol was added to the supernatant and agitated (100 rpm) overnight at 4° C. to precipitate EPS.

The sample was centrifuged at 3,313×g for 30 min at 4° C. and the carbohydrate pellet was resuspended in 10 ml deionised water and dialysed (molecular cut-off of 12,000 Da) against deionised water at 4° C. for 2 weeks with daily changes of water. The EPS content of the suspension was estimated using the phenol-sulphuric method and was expressed as glucose equivalent of the standard curve.

Confocal Laser Scanning Microscopy (CLSM)

After four weeks of yoghurt storage, the microstructure of the yoghurt samples was examined at room temperature following staining using confocal laser scanning microscopy (CLSM). The labelling fluorescent stain, Fast Green FCF (Sigma-Aldrich, Wicklow, Ireland) was used to label protein. A 10 μl volume of an aqueous solution of Fast Green FCF (1.0 g/l) was applied to the surface of unstirred and stirred yoghurt sample. Fast green FCF labels protein when excited at 633 nm. The lectin Wheat Germ Agglutinin-Alexafluor 555 conjugate (WGA; Invitrogen) was used to visualize the bacterial exopolysaccharides. The Wheat Germ Agglutinin 555 stock solution was freshly prepared by dissolving 1 mg of the lectin Wheat Germ Agglutinin-Alexafluor 555 conjugate in a mixture of 1.5 ml phosphate buffer at pH 6.3 and 0.5 ml ethanol. The Wheat Germ Agglutinin 555 solution (10 μl) was added to the surface of the yoghurt and incubated for 1 h. The lectin Wheat Germ Agglutinin-Alexafluor 555 labels EPS when excited at 561 nm. To label the bacteria, the SYTO9 fluorescent dye was used (excitation and emission maxima, 480 and 500 nm respectively) which penetrated both viable and non-viable bacteria. A 10 μl aliquot of the SYTO9 solution was added to the surface of the yoghurt. The argon ion laser was used to generate the 488 line for excitation and visualisation of the bacteria. All samples were gently stirred after adding the dyes and incubated for 1 h at 5° C. to allow diffusion. Imaging was performed using a Leica TCS SP3 confocal laser scanning microscope (Leica Microsystems, Heildelberg GmbH, Mannheim, Germany) using a 63× objective. A minimum of 4 z-stacks were taken per sample with representative cross-sections of micrographs. The images were acquired with 512×512 pixel resolution in TIFF format.

Stability of *Lb. mucosae* DPC 6426 During Fermented Milk Product Development

A pilot study to determine the efficacy of orally administrated *Lactobacillus mucosae* DPC 6426 for reducing cholesterol and blood-lipid levels in healthy, mildly hypercholesterolaemic (≥5 mmol/L and <7.5 mmol/L) male adults was also performed. The fermentation substrate consisted of 10% (w/v) reconstituted skim milk (RSM) supplemented with 5% (w/v) sucrose. Fermentation was carried out to a final pH ~5.3. Following fermentation the product was cooled down to ~4° C. and 0.2% (v/v) commercially available vanilla extract was added to fermented milk. Culture viability was performed before and after fermentation and also after 1 week of storage at 4° C. EPS concentration of fermented milk was also determined. An independent sensory panel was appointed to validate odour, flavour, aftertaste and texture of vanilla flavoured fermented milk.

To Determine if *Lb. mucosae* DPC 6426 Reduces Total Cholesterol in Mildly Hypercholesterolaemic (≥5 mmol/L and <7.5 mmol/L) Male Adults Following recruitment of subjects and inclusion and exclusion criteria, 10 subjects participated in the pilot study for 6 weeks. Subjects were instructed to not consume any probiotics or plant sterol esters supplements for the duration of the study. Subjects ingested 100 ml of fermented milk containing ~$10^{10}$ CFU per 100 ml viable *Lb. mucosae* DPC 6426 and ~162.2 mg/L (±18.7 mg/L) EPS daily for 6 weeks. Fasting blood was collected at day 0 (baseline), week 1, 2, 3, 4, 5, 6 and 2 weeks post completion. Samples were analysed using Cholestech LDX system (APC) and independently at Cork University Hospital (CUH). Analyses included total cholesterol, HDL cholesterol, non-HDL cholesterol, triglycerides, LDL cholesterol, HDL cholesterol to total cholesterol ratio and glucose. Results were subjected to paired T-test. Level of significance was established at p≤0.05, unless otherwise stated.

Statistical Analysis

Data ($\bar{x}$±SEM) represent results from triplicate trials during the isolation and characterisation experiments. Remaining data are presented as means per group±the means of standard error (SEM). All data were analysed by unpaired t-test. All results were considered significant at p≤0.05 unless otherwise stated.

Results

One strain from the DPC culture collection (DPC 6426, from bovine faeces) exhibited a viscous phenotype when grown on solidified medium in addition with 2% (w/v) and 5% (w/v) glucose. Comparison of sequence data revealed that isolate DPC 6426 belongs to the species *Lactobacillus mucosae* (99% query identity, E-value: 0). Homology analysis using the BLAST network are given in Table 2.

TABLE 2

Homology search analysis using the BLAST network for strain DPC 6426 to identify ropy phenotypes isolated from bovine faeces.

| Isolate | Organism | Query coverage (%) | Percentage identity (%) | E-value |
|---|---|---|---|---|
| DPC 6426 | *Lactobacillus mucosae* strain FSL-04 16S ribosomal RNA gene | 100 | 99 | 0.0 |
| | *Lactobacillus mucosae* gene for 16S ribosomal RNA | 99 | 99 | 0.0 |
| | *Lactobacillus mucosae* gene for 16S ribosomal RNA | 99 | 99 | 0.0 |

Colonies of *Lb. mucosae* DPC 6426 were white, smooth and convex. The cell size was ~2 μm long and ~1 μm wide. *Lb. mucosae* DPC 6426 grew well at 37° C. under aerobic and anerobic conditions, weakly at 30° C. under aerobic and anerobic conditions and weakly at 45° C. under aerobic and anerobic conditions in MRS medium. Catalase activity was negative, while the Gram-reaction was positive. Gas was produced from glucose, indicating that *Lb. mucosae* DPC 6426 is hetero-fermentative.

The API 50 CH kit was used to determine sugar fermentation patterns for *Lb. mucosae* DPC 6426 and 49 carbohydrates were tested for sugar fermentation. The API 50 CH results are presented in Table 3.

TABLE 3

Carbohydrate fermentation profile of *Lb. mucosae* DPC 6426 using API 50CH stripes and API 50CHL medium. Results represent the means from triplicate experiments.

| Carbohydrate | *Lb. mucosae* DPC 6426 |
|---|---|
| L-arabinose | positive |
| D-ribose | positive |
| D-fructose | positive |
| D-maltose | positive |
| D-lactose | positive |
| D-xylose | positive |
| D-galactose | positive |
| D-glucose | positive |
| D-melibiose | positive |
| D-saccharose | positive |
| D-raffinose | positive |
| Methyl-βD-Xylopyranoside | positive |
| 2-keto-gluconate | negative |

Compositional analysis of EPS isolated from *Lb. mucosae* DPC 6426 indicated that it is comprised of seven monosaccharide residues: xylose, fucose, mannose, glucose, galactose, N-acetylglucosamine, and N-acetylmannosamine (Table 4).

TABLE 4

Compositional analysis of EPS isolated from *Lb. mucosae* DPC 6426 using GC-MS after samples were refluxed in 2N TFA and conversion into pre-acetylated aldononitrile acetates.

| Sugar residue | R.T. (min) | Normalized percentage of total EPS isolated from *Lb. mucosae* DPC 6426 |
|---|---|---|
| Xylose | 7.256 | 5.92 |
| Fucose | 7.717 | 2.35 |
| Mannose | 11.548 | 46.22 |
| Glucose | 11.717 | 22.22 |
| Galactose | 12.057 | 15.62 |
| N-acetylglucosamine | 14.045 | 6.79 |
| N-acetylmannosamine | 15.403 | 0.88 |

Figure 6:
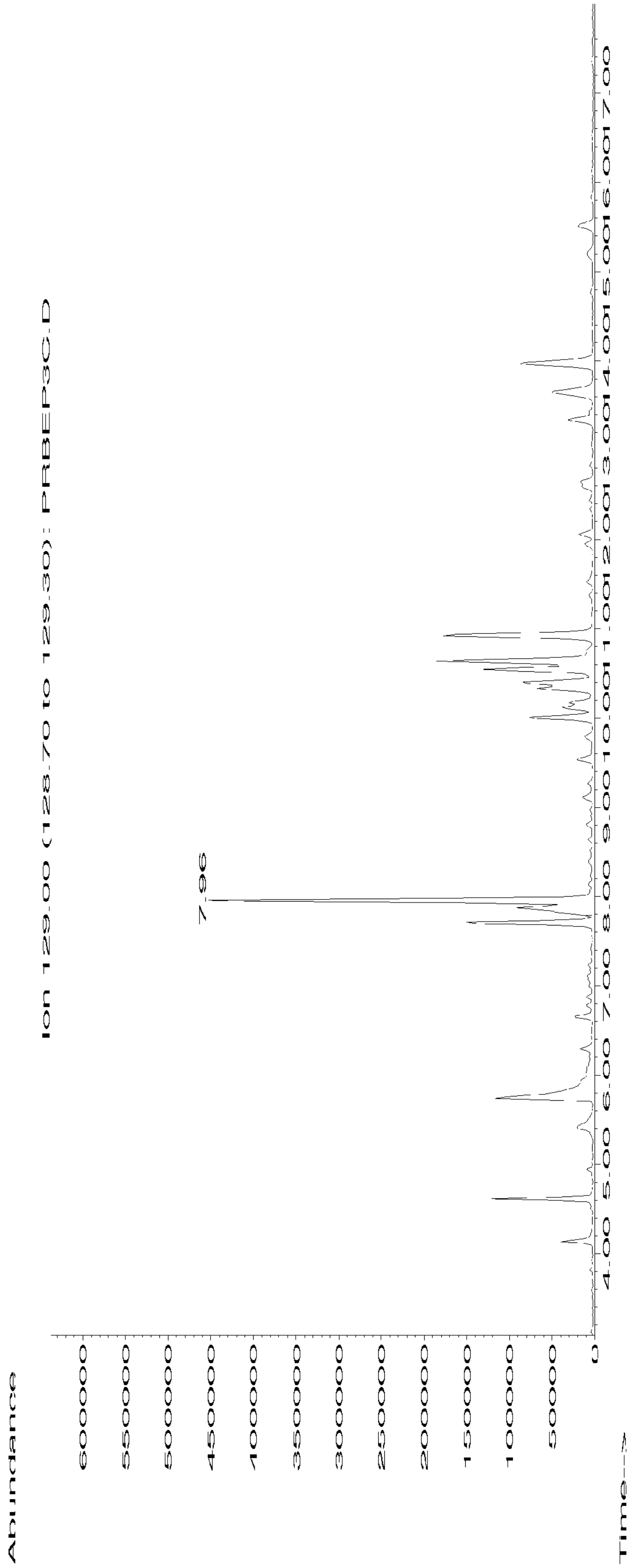
FIG. 6 illustrates an ion extracted for m/z 129 chromatograph of EPS of *Lb. mucosae* DPC 6426 after permethylation (95° C. for 1 h). The chromatographs showed 2.3.5 methyl xylose, 2.3.4.6 methyl mannose, 3.4.6 methyl mannose, 2.3.4 methyl mannose and 3.4 methyl mannose after permethylation at 95° C. for 1 h (see Table 4). Xylose was detected as 2.3.5 methyl xylose, meaning that it was a terminal residue. Terminal mannose and glucose residues were also detected on the polysaccharide backbone of 6 or 2-linked mannose with some 3-linked mannose in the ratio of 2:2:1 6-linked mannose:2-linked mannose:3-linked mannose.
Figure 7:
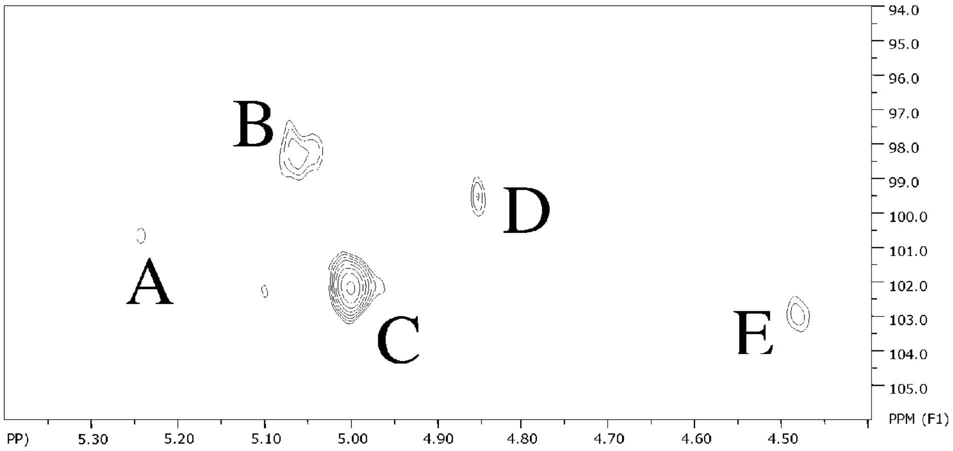
FIG. 7 showed the characteristic carbohydrate ring protons in the range 3.5-4.2 ppm (60-75 ppm), including prominent C-6 methylene $^{13}C$ signals at approximately 62 ppm. Correlations at 2.1 ppm ($^{1}H$) and 22 ppm ($^{13}C$) were likely due to 0-acetyl groups.
Figure 7:
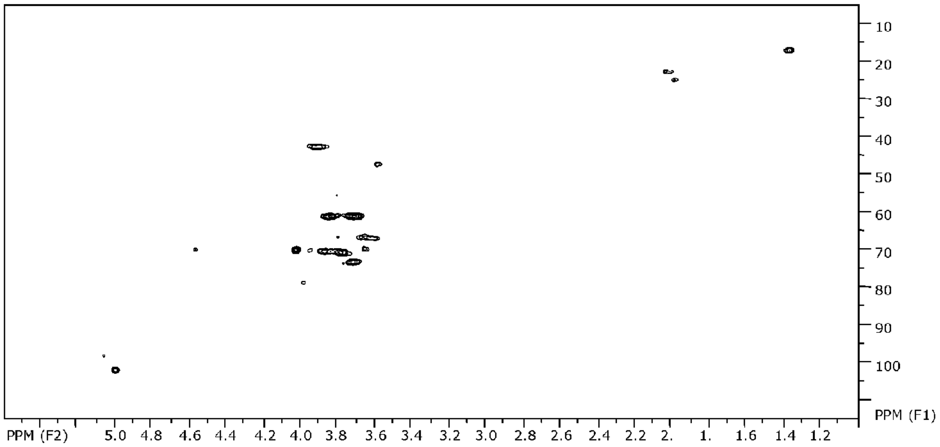
Figure 8:
FIG. 8 illustrates the generalised structure for EPS isolated from *Lb. mucosae* DPC 6426 based on GC-MS, ion extraction m/z 129 chromatograph and proton NMR spectrograph analysis.

The seven monosaccharides are presented in the following ratios: 1.3:0.5:10.0:4.8:3.3:1.5:0.2, making it a mannose-rich EPS. These results also suggest a considerable structural complexity. Major sugar residues present are Man:Glc:Gal in an approximate ratio of 10:4:3, with mannose comprising about 50% of total sugars. The Xyl:Fuc ratio is 3:2. EPS from *Lb. mucosae* DPC 6426 showed terminal xylose and the majority of glucose was terminal. Mannose was predominately 6 or 2-linked with some 3-linked in the ration of 2:2:1 6-linked:2-linked:3-linked. EPS from *Lb. mucosae* DPC 6426 had a 1,6-linked mannose backbone with 1,2-linked or 1,3-linked branches starting with mannose and ending with either 1,2-linked xylose or glucose. FIG. 8 shows the generalized structure for EPS from *Lb. mucosae* DPC 6426. For EPS isolated from Lb. *mucosae* DPC 6426 ion extraction m/z 129 chromatographs showed 2.3.5 methyl xylose, 2.3.4.6 methyl mannose, 3.4.6 methyl mannose, 2.3.4 methyl mannose and 3.4 methyl mannose after permethylation at 95° C. for 1 h (Table 5 and FIG. 6).

TABLE 5

Ion extraction m/z 129 chromatograph analyses of EPS linkages after permethylation of the EPS from Lb. mucosae DPC 6426.

| | ~percentage from area percent report | ~ratio |
|---|---|---|
| 2,6-linked mannose | 10 | 2 |
| 6-linked mannose | 15 | 3 |
| 2-linked mannose | 15 | 3 |
| Terminal mannose | 25 | 5 |
| Terminal xylose | 5 | 1 |

The total EPS concentration of the fermentation medium supplemented with 5% (w/v) glucose was analysed by colorimetric phenol-sulphuric method. A glucose standard curve was generated to estimate EPS concentrations as glucose equivalent for Lb. *mucosae* DPC 6426 (data not shown). Estimated EPS production for *Lb. mucosae* DPC 6426 was 196 mg/l when grown in MRS broth supplemented with 5% (w/v) glucose for 48 h at 37° C. anaerobically.

There was no significant difference in food intake between the groups administrated Lb. *mucosae* DPC 6426 and the placebo control (Table 6). As expected, body weights increased gradually over time for both groups. Percentage weight gain for the Lb. *mucosae* DPC 6426 group was 19.08% (±6.36) and for the control group 17.71% (±6.26) over 12 weeks on the high fat (60% kcal from fat), high cholesterol (2% w/w) diet. The average weight of *Lb. mucosae* DPC 6426 group increased from 28.24 g (±0.73) to 33.51 g (±0.95) and the weight of the control group increased from 28.37 g (±0.46) to 33.46 g (±1.33), but there was no significant difference in final body mass (Table 5).

TABLE 6

Average daily food intake during the experiment and percentage weight gain of apoE-deficient mice after 12 weeks consuming 60% (kcal) fat diet with 2% (w/w) cholesterol and administration of *Lb. mucosae* DPC 6426 and control group. $\bar{x}$ ± SEM.

| | *Lb. mucosae* DPC 6426 | Control | p value |
|---|---|---|---|
| Food intake (g/day) | 3.36 ± 0.3 | 3.16 ± 0.10 | 0.478 |
| Percentage weight gain (%) | 19.08 ± 6.36 | 17.71 ± 6.26 | 0.801 |

The masses of various adipose tissues (subcutaneous adipose tissue, epididymal adipose tissue and mesenteric adipose tissue), liver and caecum are shown in terms of weight per 100 g of body weight (Table 7). Although all animals in the control group developed fatty livers, no significant differences were found for relative liver weights between the groups at the end of the trial. Only three of 9 animals in the *Lb. mucosae* DPC 6426 fed group developed fatty livers following 12 weeks of dietary intervention.

TABLE 7

Relative liver, caecum, subcutaneous adipose tissue (S.A.T.), epididymal adipose tissue (E.A.T.) and mesenteric adipose tissue (M.A.T.) weight of apoE-deficient mice after 12 weeks consuming 60% (kcal) fat diet with 2% (w/w) cholesterol and administration of *Lb. mucosae* DPC 6426 and control group. $\bar{x}$ ± SEM.

| Organ/tissue in g per 100 g body weight | *Lb. mucosae* DPC 6426 | Control | p value |
|---|---|---|---|
| Liver | 4.38 ± 0.11 | 4.54 ± 0.07 | 0.281 |
| Caecum | 1.17 ± 0.13 | 1.11 ± 0.10 | 0.988 |
| S.A.T | 1.49 ± 0.27 | 1.81 ± 0.34 | 0.464 |
| E.A.T. | 2.40 ± 0.43 | 3.32 ± 0.43 | 0.151 |
| M.A.T. | 0.68 ± 0.11 | 0.88 ± 0.11 | 0.229 |

TABLE 8

Blood lipid concentrations in serum of apoE-deficient mice after 12 weeks consuming 60% (kcal) fat diet with 2% (w/w) cholesterol and administration of *Lb. mucosae* DPC 6426 and control group. HDL/TC: HDL-cholesterol/total cholesterol. $\bar{x}$ ± SEM.

| | *Lb. mucosae* DPC 6426 | Control | p value |
|---|---|---|---|
| HDL (mg/dL) | 82.06 ± 19.62 | 49.60 ± 10.44 | 0.180 |
| Ratio HDL/TC | 0.35 ± 0.1 | 0.14 ± 0.04 | 0.009 |

The ratio of HDL cholesterol to total cholesterol was significantly increased (p≤0.01) in the liver of the *Lb. mucosae* DPC 6426 fed group compared with the placebo control group following 12 weeks of dietary intervention (Table 9).

TABLE 9

Liver lipid profile of apoE-deficient mice after 12 weeks consuming 60% (kcal) fat diet with 2% (w/w) cholesterol and administration of the *Lb. mucosae* DPC 6426 and control group. HDL-C/TC: HDL-cholesterol/total cholesterol. $\bar{x}$ ± SEM.

| | *Lb. mucosae* DPC 6426 | Control | p value |
|---|---|---|---|
| HDL (mmol/mg liver) | 0.029 ± 0.016 | 0.027 ± 0.006 | 0.743 |
| Ratio HDL/TC | 0.81 ± 0.06 | 0.26 ± 0.12 | 0.0004 |

In an effort to elucidate the mechanism by which orally administrated *Lb. mucosae* DPC 6426 lowered the total cholesterol concentration in the serum, the expression of two key enzymes in cholesterol metabolism, HMG-CoA reductase and CYP7A1 genes, was quantified using real-time fluorescence monitoring reverse transcription-(RT)-PCR and the comparative $2^{-\Delta Ct}$ method. No significant differences in the gene expression of either HMG-CoA reductase and CYP7A1 in the *Lb. mucosae* DPC 6426 fed group compared with the placebo control group (Table 10).

TABLE 10

HMG-CoA reductase and CYP7A1 gene expression of apoE-deficient mice after 12 weeks consuming 60% (kcal) fat diet with 2% (w/w) cholesterol and administration of the *Lb. mucosae* DPC 6426 and control group. $\bar{x}$ ± SEM.

| gene | *Lb. mucosae* DPC 6426 | Control | p value |
|---|---|---|---|
| HMG-CoA reductase ($2^{-\Delta Ct}$ value) | 0.411 ± 0.206 | 0.175 ± 0.051 | 0.255 |
| CYP7A1 ($2^{-\Delta Ct}$ value) | 0.020 ± 0.015 | 0.005 ± 0.001 | 0.391 |

Figure 9:
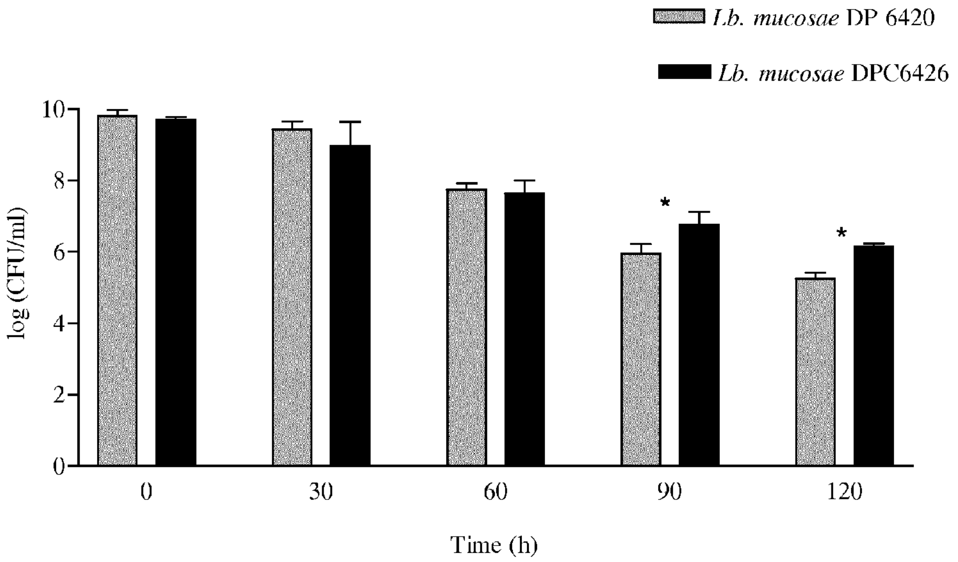
FIG. 9 illustrates the survival of the exopolysaccharide (EPS)-producing strain *Lb. mucosae* DPC 6426 and the non-exopolysaccharide (EPS)-producing strain Lb. *mucosae* DPC 6420 in 5M NaCl during 120 min of exposure. Error bars represent standard errors of the means (SEM) from triplicate experiments. An asterisk denotes a significant difference between non-EPS-producing strain *Lb. mucosae* DPC 6420 and EPS-producing strain *Lb. mucosae* DPC 6426 (* $p \leq 0.05$). Exposure of the EPS- and non-EPS-producing *Lb. mucosae* cultures to 5M NaCl in MRS medium resulted in decreased viability of both strains during 120 min of exposure at 37° C. Survival of the EPS- and non-EPS-producing strain was similar (~$10^8$ CFU/ml) during exposure for 60 min. However, after 90 min and 120 min of exposure to the high-salt concentration, a significantly 1-fold higher survival ($p \leq 0.05$) of the EPS-producing *Lb. mucosae* DPC 6426 was found compared to the non-EPS-producing *Lb. mucosae* DPC 6420.
Figure 10:
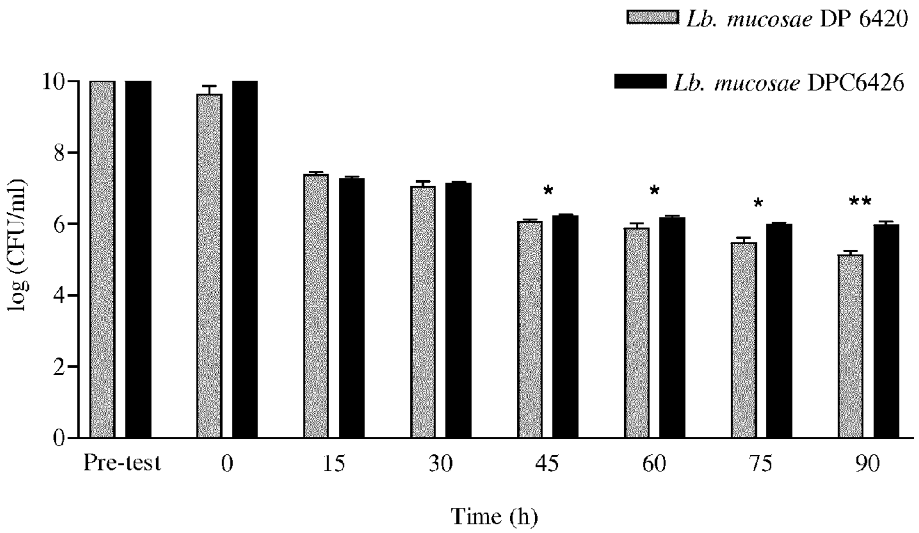
FIG. 10 is a bar chart illustrating the survival of exopolysaccharide (EPS)-producing strain *Lb. mucosae* DPC 6426 and non-exopolysaccharide (EPS)-producing strain *Lb. mucosae* DPC 6420 in 0.7% (w/v) porcine bile during 90 min of exposure. Error bars represent standard errors of the means from triplicate experiments (SEM). An asterisk denotes a significant difference between non-EPS-producing strain *Lb. mucosae* DPC 6420 and EPS-producing strain *Lb. mucosae* DPC 6426 (* $p \leq 0.05$; ** $p \leq 0.01$). Following exposure to high bile concentrations (0.7% (w/v)) over 90 min at 37° C., the survival of the EPS-producing *Lb. mucosae* DPC 6426 was significantly higher after 45 min of exposure compared to the non-EPS-producing *Lb. mucosae* DPC 6420, while both *Lb. mucosae* strains survived in high numbers during exposure to 0.7% (w/v) bile for 90 min (>$10^5$ CFU/ml).
Figure 11:
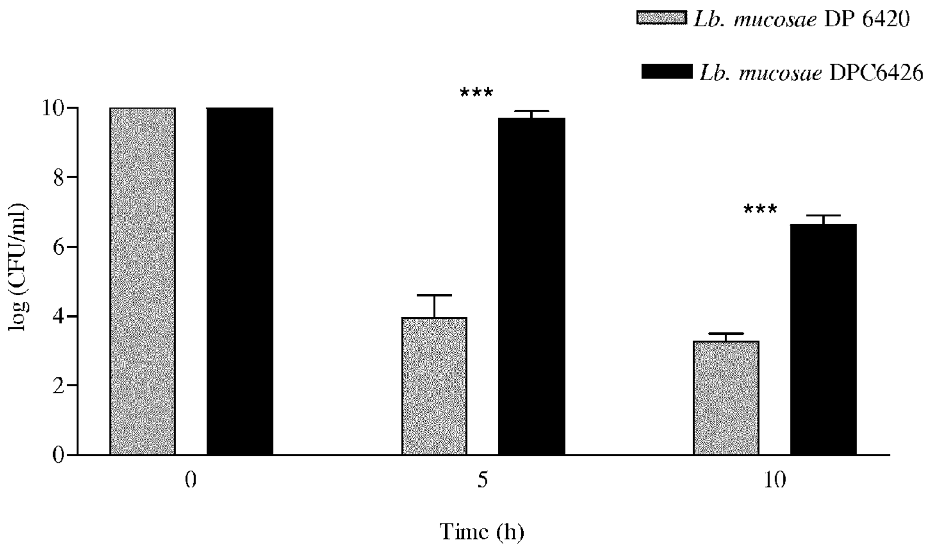
FIG. 11 is a bar chart illustrating the survival of exopolysaccharide (EPS)-producing strain *Lb. mucosae* DPC 6426 and non-exopolysaccharide (EPS)-producing strain *Lb. mucosae* DPC 6420 in simulated gastric juice (pH 2) during 10 min of exposure. Error bars represent standard errors of the means from triplicate experiments (SEM). An asterisk denotes a significant difference between non-EPS-producing strain *Lb. mucosae* DPC 6420 and EPS-producing strain *Lb. mucosae* DPC 6426 (*** $p \leq 0.0001$). *Lb. mucosae* DPC 6426 exhibited significantly higher tolerance to simulated gastric juice, pH 2. compared with *Lb. mucosae* DPC 6420 during 10 min of exposure at 37° C. A 6 log higher survival ($p \leq 0.0001$) of *Lb. mucosae* DPC 6426 was observed after 5 min exposure to simulated gastric juice, pH 2 and a 3 log higher viability ($p \leq 0.0001$) after 10 min of exposure when compared to *Lb. mucosae* DPC 6420.
Figure 12:
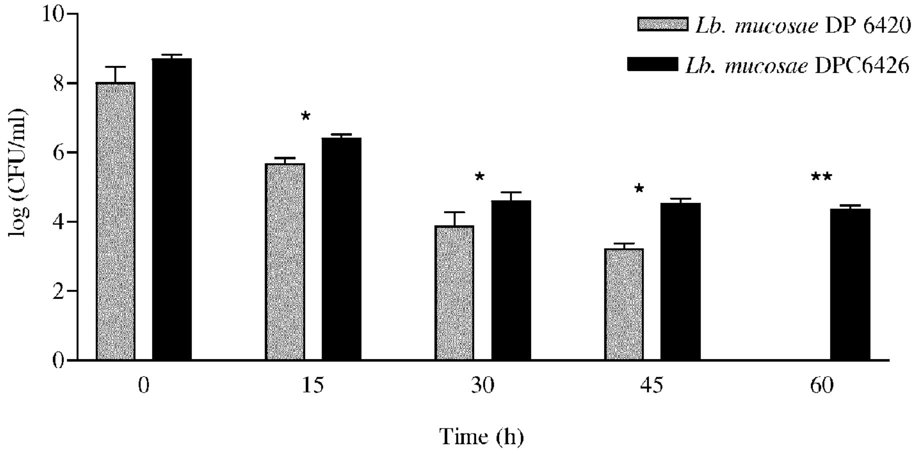
FIG. 12 is a bar chart illustrating the survival of exopolysaccharide (EPS)-producing strain *Lb. mucosae* DPC 6426 and non-exopolysaccharide (EPS)-producing strain *Lb. mucosae* DPC 6420 in acidic conditions (HCl, pH 2) during 60 min of exposure. Error bars represent standard errors of the means from triplicate experiments (SEM). An asterisk denotes a significant difference between non-EPS-producing strain *Lb. mucosae* DPC 6420 and EPS-producing strain *Lb. mucosae* DPC 6426 (* $p \leq 0.05$; ** $p \leq 0.001$). A significantly higher survival ($p \leq 0.05$) of EPS-producing *Lb. mucosae* DPC 6426 was found following exposure to 1M HCl, pH 2 after 15 min exposure at 37° C. compared to non-EPS-producing *Lb. mucosae* DPC 6420 A further decline of viability below detection level was found for the non-EPS producing *Lb. mucosae* DPC 6420 at 60 min of exposure to 1M HCl, pH 2, while EPS-producing *Lb. mucosae* DPC 6426 exhibited survival ($p \leq 0.001$) following 60 min of exposure.
Figure 13:
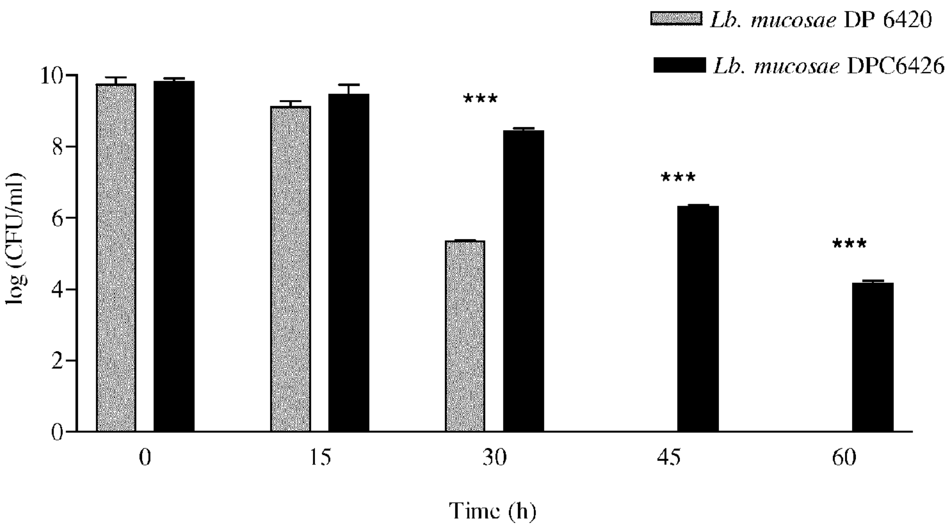
FIG. 13 is a bar chart illustrating the survival of exopolysaccharide (EPS)-producing strain *Lb. mucosae* DPC 6426 and non-exopolysaccharide (EPS)-producing strain *Lb. mucosae* DPC 6420 at 55° C. during 60 min of exposure. Error bars represent standard errors of the means from triplicate experiments (SEM). An asterisk denotes a significant difference between non-EPS-producing strain *Lb. mucosae* DPC 6420 and EPS-producing strain *Lb. mucosae* DPC 6426 (*** $p \leq 0.0001$). After 30 min exposure to a temperature of 55° C., a significantly higher survival ($p \leq 0.0001$) for EPS-producing *Lb. mucosae* DPC 6426 was observed compared with the non-EPS producing Lb. *mucosae* DPC 6420. This trend was maintained throughout the assay of 60 min. By 45 min exposure to 55° C., the viability of *Lb. mucosae* DPC 6420 was found to be undetectable, while *Lb. mucosae* DPC 6426 maintained ~$10^6$ CFU/ml ($p \leq 0.0001$) which declined to ~$10^4$ CFU/ml by 60 min of heat exposure. The in situ produced EPS by *Lb. mucosae* DPC 6426 was advantageous in terms of enhanced heat tolerance compared with the absence of EPS.
Figure 14:
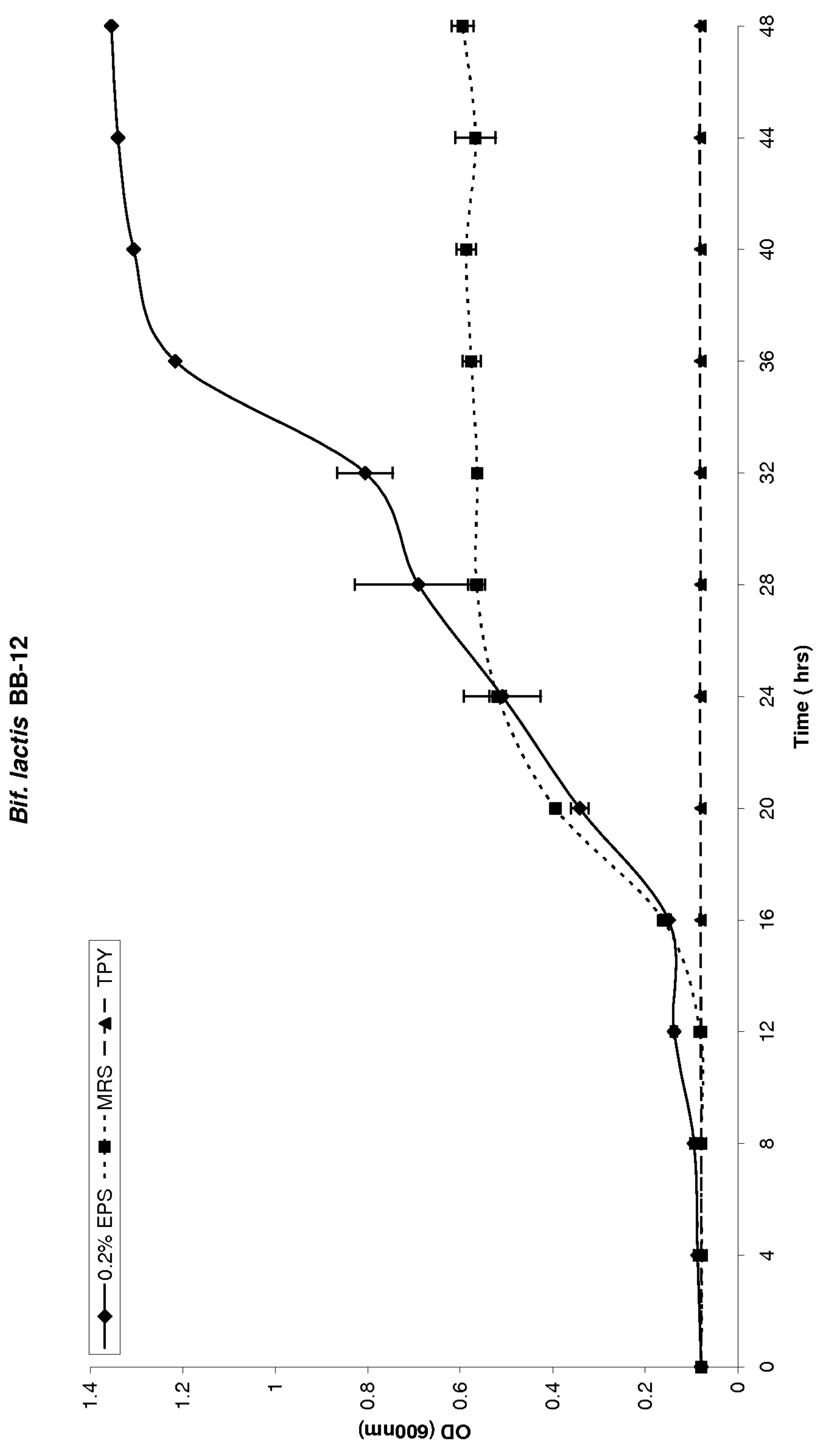
FIG. 14 illustrates the growth behaviour of *B. lactis* BB-12 in EPS supplemented medium, MRS medium for bifidobacteria and TPY medium with no added sugar source during 48 h incubation at 37° C. anaerobically. Error bars represent standard errors of the means from triplicate experiments (±SEM). The exponential growth phase of *B. lactis* BB-12 was found between 14 h and 24 h of incubation in MRS medium, while the stationary phase was reached between 24 h and 48 h of incubation in MRS medium, with a final $OD_{600}$ reading of 0.6. In the presence of EPS, *B. lactis* BB-12 showed slower growth behaviour compared to MRS medium and a longer exponential growth phase (~20 h) observed between 16 h and 36 h of incubation. No further growth was found after 36 h of incubation. Nevertheless, turbidity values of the culture measured were 1-fold higher for EPS-supplemented medium (final $OD_{600}$:1.3) compared to MRS medium (final $OD_{600}$:0.6).
Figure 15:
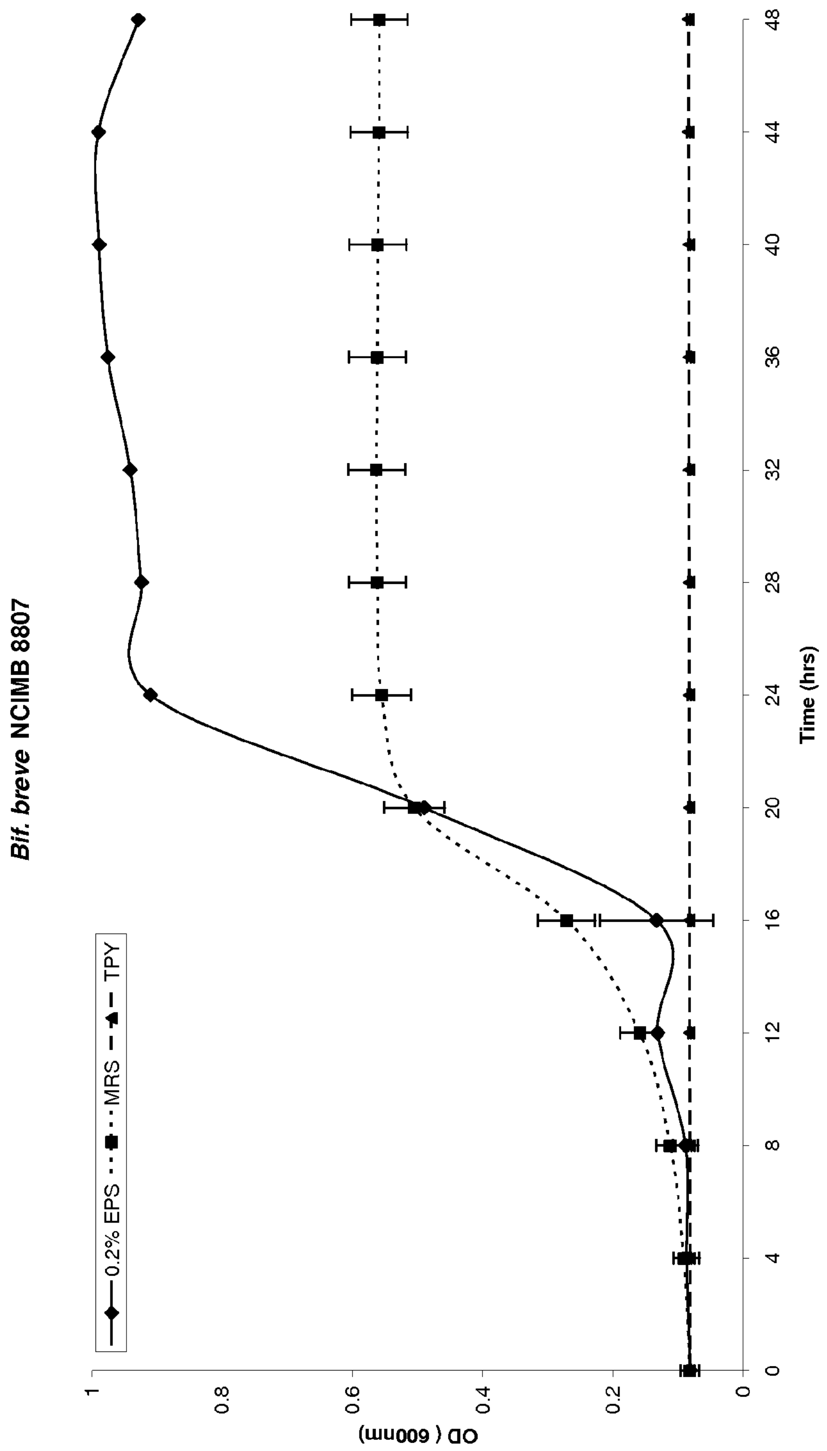
FIG. 15 illustrates the growth behaviour of *B. breve* NCIMB 8807 in EPS supplemented medium, MRS medium for bifidobacteria and TPY medium with no added sugar source during 48 h of incubation at 37° C. anaerobically. Error bars represent standard errors of the means from triplicate experiments (±SEM). The bifidogenic effect of the isolated EPS was also tested on *B. breve* NCIMB 8807. No growth was observed for TPY medium without the addition of a sugar source. Similar growth behaviour was observed for *B. breve* NCIMB 8807 throughout the first 8 h of incubation in MRS for bifidobacteria and TPY medium supplemented with 0.2% (w/v) EPS. Exponential growth phase in MRS for bifidobacteria was found between 8 h and 20 h of incubation followed by the stationary phase with an $OD_{600}$ reading of 0.6 thereafter.
Figure 16:
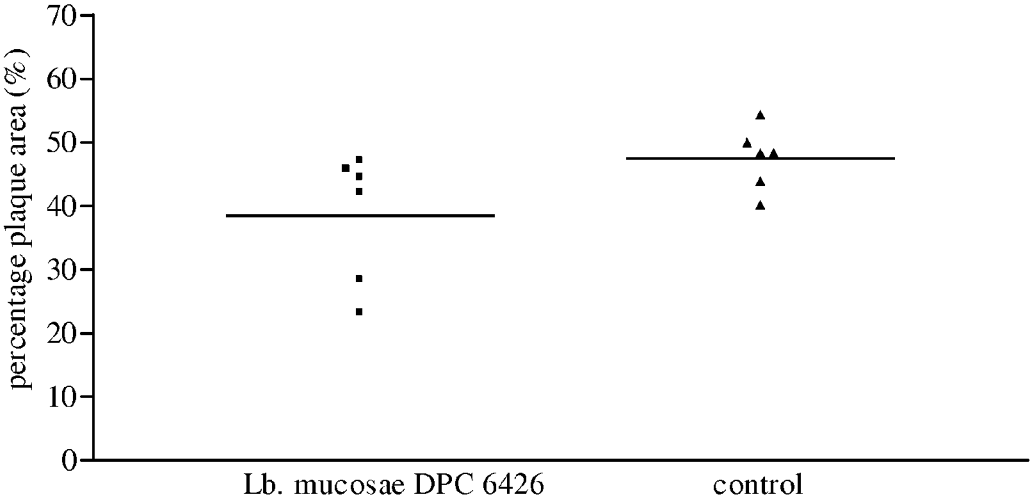
FIG. 16 illustrates the quantification of Oil Red O staining in the aorta of apoE-deficient mice after 12 weeks consuming 60% (kcal) fat diet with 2% (w/w) cholesterol and administration of *Lb. mucosae* DPC 6426 and control group. Data of individual aortas. p=0.078. Both groups of animals fed the high fat diet with 2% (w/w) cholesterol in combination with *Lb. mucosae* DPC 6426 and placebo control developed atherosclerotic lesion after 12 weeks. The effect of daily administration of EPS-producing *Lb. mucosae* DPC 6426 on established lesions was quantified in aortas of individual mice. While the percentage plaque area for the *Lb. mucosae* DPC 6426 fed group was numerically lower (38.49±4.13) than the control group (47.50±2.01), the differences were not statistically significant (p=0.078).
Figure 17:
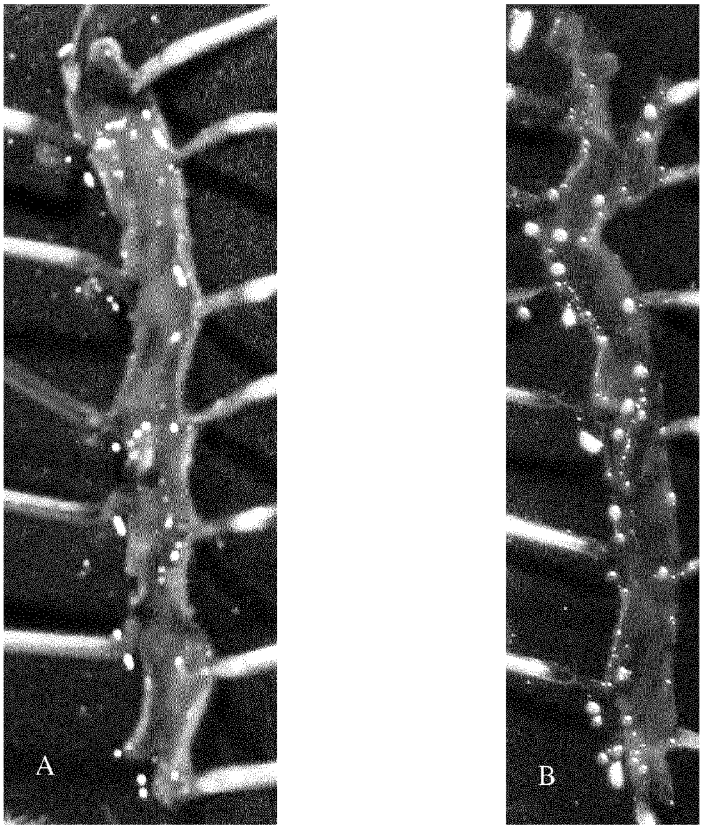
FIGS. 17A and 17B illustrate Representative Oil Red O stained images in the aorta of apoE-deficient mice after 12 weeks consuming 60% (kcal) fat diet with 2% (w/w) cholesterol and administration of *Lb. mucosae* DPC 6426 and control group. White spots are reflections of buffer and should not be considered. Red areas represent Oil Red O staining. A: Selected aorta of *Lb. mucosae* DPC 6426 and B: Selected aorta of control group. Lesion formation was located throughout the aortas for both groups.
Figure 18:
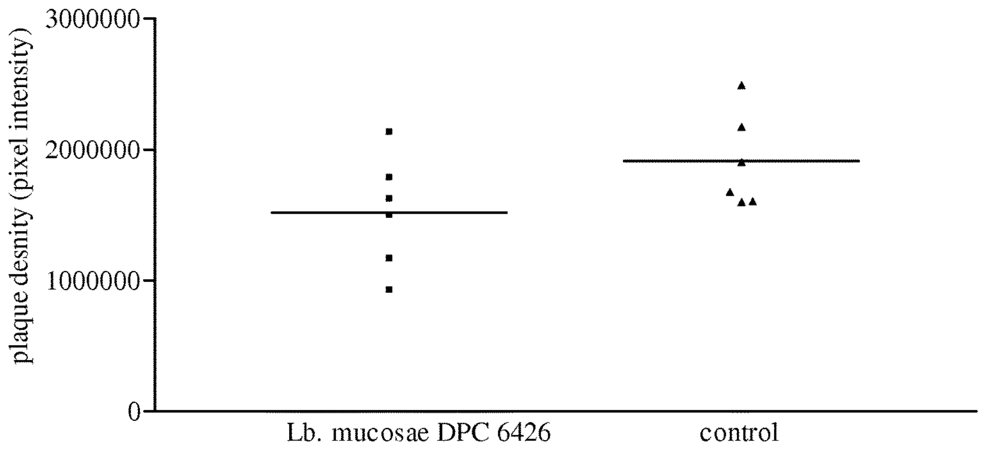
FIG. 18 is a bar chart illustrating the quantification of percentage plaque density after Oil Red O staining in the aorta of apoE-deficient mice after 12 weeks consuming 60% (kcal) fat diet with 2% (w/w) cholesterol and administration of Lb. *mucosae* DPC 6426 and control group. Data of individual aortas. p=0.123. here was a trend towards a reduction of plaque density of atherogenic areas for the *Lb. mucosae* DPC 6426 fed group compared with the control group although the differences were not significant (p=0.123).

The present invention demonstrates that EPS producing *Lb. mucosae* DPC 6426 exhibited superior technological performance than non-EPS-producing *Lb. mucosae* DPC 6420. The present invention also demonstrates the technological performance of EPS producing *Lb. mucosae* DPC 6426 compared to non-EPS-producing *Lb. mucosae* DPC 6420, by comparing the stress-tolerance of both strains against such stresses as osmotic (salt) stress (FIG. 9), acid stress (FIG. 12), bile exposure (FIG. 10) and heat stress (FIG. 13). Following exposure of both strains to all stresses, it was found that *Lb. mucosae* DPC 6426 exhibited significantly greater stress tolerance than Lb. *mucosae* DPC 6420.

Tolerance to acidic conditions in the stomach and bile in the small intestine is essential to deliver beneficial effects of probiotic cultures to the host. The acid conditions in the stomach can vary based on the food digested and range between pH 1 and pH 3. Some delivery matrices of probiotic cultures like milk, milk compounds and milk products increased the survival of probiotic cultures by their buffering capacity. It is also known that some *Lactobacillus* species of intestinal origin are considered intrinsically resistant to acidic environments.

The viability of food-grade LAB cultures mainly suffers during unfavourable food-processing conditions, for example high heat exposure during spray drying. Lactobacilli are generally sensitive to temperatures above 50° C., although thermal tolerance appears to be strain and species specific. The superior thermal tolerance of the EPS producing *Lb. mucosae* DPC 6426 strain of the present invention to elevated temperatures (55° C.) compared to the non-EPS-producing *Lb. mucosae* DPC 6420 was demonstrated (FIG. 13).

In a further embodiment of the present invention, it was investigated whether dietary administration of EPS-producing *Lb. mucosae* DPC 6426 exerted a beneficial effect in terms of prevention of atherosclerosis in the ApoE-deficient mouse model fed a hypercholesterolemic, high fat diet for 12 weeks. The ApoE-deficient mouse model has the ApoE gene inactivated and develops hypercholesterolemia and atherosclerosis, without the need to increase fat and/or cholesterol levels in the diet and mimics humans metabolically. However, the model exhibits mainly lesion in the aortic root area, but develops a more widely distributed atherosclerosis which mimics human atherosclerosis development when fed a hypercholesterolemic diet. In the present invention, animals were fed a high fat (60% kcal), high cholesterol (2% (w/w)) diet for 12 weeks (Table 6). Dietary administration of EPS-producing *Lb. mucosae* DPC 6426 (~$1\times10^9$ CFU/dose) in drinking water of experimental animals had no statistical effect on food intake and percentage body weight gain (Table 6).

Figure 19:
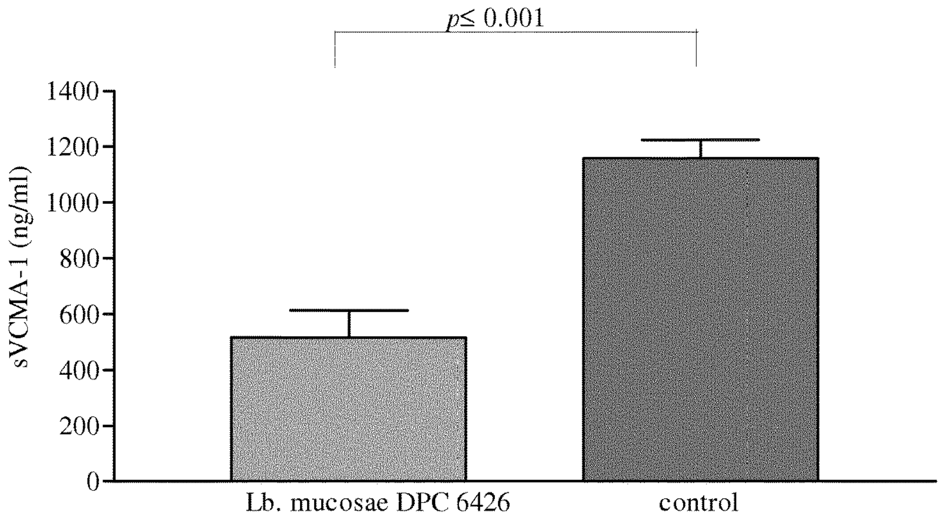
FIG. 19 is a bar chart illustrating sVCAM-1 concentrations in serum of apoE-deficient mice after 12 weeks consuming 60% (kcal) fat diet with 2% (w/w) cholesterol and administration of *Lb. mucosae* DPC 6426 and control group. Error bars represent standard errors of the means (SEM). p=0.0002. It was found that there was a significant reduced (p≤0.001) concentration of sVCAM in serum for the *Lb. mucosae* DPC 6426 fed group compared with the placebo control group.

Following dietary intervention with the high fat high cholesterol diet for 12 weeks, both animal groups exhibited atherosclerosis, a finding that is in agreement with the animal model. The pathogeneses of atherosclerosis is a complex process depending on various factors. Suppression of inflammation is a process in lesion development and therefore, the soluble vascular adhesion molecule-1 (sVCMA-1), which contributes to pathological conditions such as atherosclerosis, was determined in serum samples (FIG. 19). VCMA-1 is a type I membrane glycoprotein, which is important for the recruitment of leukocytes to sites of inflammation. As illustrated in FIG. 19, significantly lower levels of sVCAM-1 were detected in serum of *Lb. mucosae* DPC 6426 fed animals compared with the placebo control group. Lower levels of sVCAM-1 in serum may therefore reflect lower expression of VCAM-1 in the arterial walls, which contribute to atherosclerosis development. This result indicates that bacterial EPS produced by *Lb. mucosae* DPC 6426 influenced the inflammation process.

Figure 20:
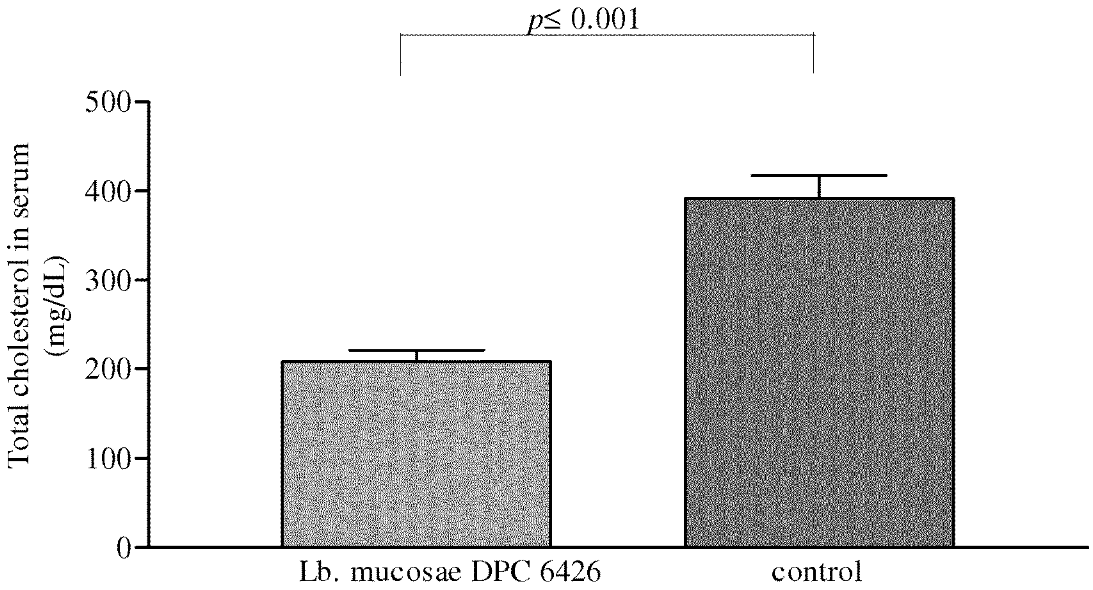
FIG. 20 is a bar chart illustrating total cholesterol concentrations in serum of apoE-deficient mice after 12 weeks consuming 60% (kcal) fat diet with 2% (w/w) cholesterol and administration of *Lb. mucosae* DPC 6426 and control group. Error bars represent standard errors of the means (SEM). p=0.0002. Total cholesterol in serum was significantly reduced (p≤0.001) by ~53% for the *Lb. mucosae* DPC 6426 fed group compared with control group.
Figure 21:
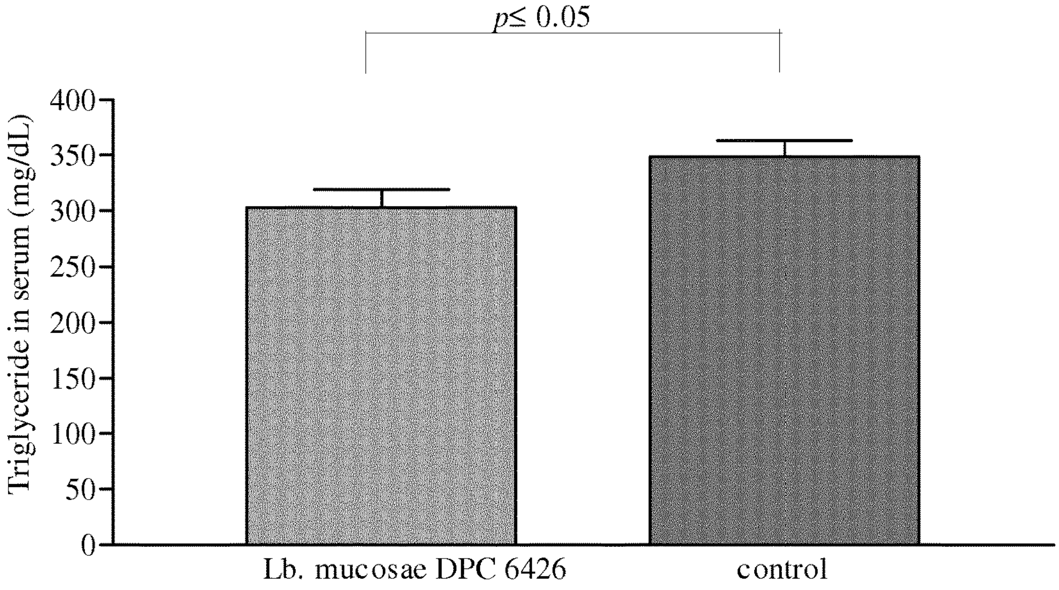
FIG. 21 is a bar chart illustrating triglyceride concentrations in serum of apoE-deficient mice after 12 weeks consuming 60% (kcal) fat diet with 2% (w/w) cholesterol and administration of *Lb. mucosae* DPC 6426 and control group. Error bars represent standard errors of the means (SEM). p=0.037. Triglyceride concentrations in serum were significantly reduced (p≤0.05) in the *Lb. mucosae* DPC 6426 fed group compared with the placebo control group.

Dietary supplementation of the EPS producing *Lb. mucosae* DPC 6426 was shown to significantly decrease total cholesterol concentration in serum of the apoE-deficient mice (FIG. 20). Administration of EPS-producing *Lb. mucosae* DPC 6426 resulted in significantly reduced total cholesterol in serum (by ~53%) compared with the placebo control group.

Figure 22:
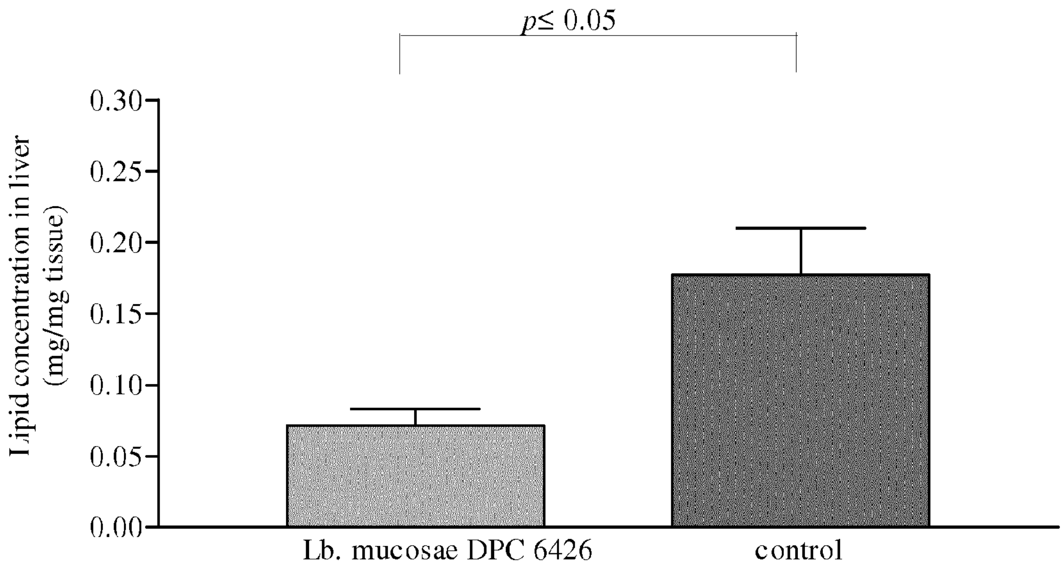
FIG. 22 is a bar chart illustrating lipid concentrations in livers of apoE-deficient mice after 12 weeks consuming 60% (kcal) fat diet with 2% (w/w) cholesterol and administration of the *Lb. mucosae* DPC 6426 and control group. Error bars represent standard errors of the means (SEM). p=0.004. Total liver lipid concentrations were significantly decreased (p≤0.05) in the *Lb. mucosae* DPC 6426 fed group compared with placebo control group following 12 weeks of dietary intervention.
Figure 23:
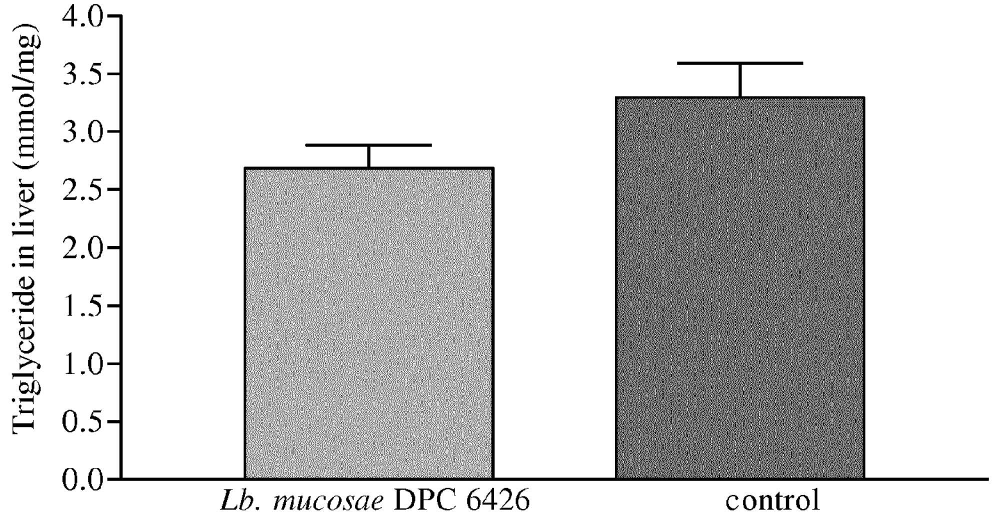
FIG. 23 is a bar chart illustrating triglyceride concentrations in livers of apoE-deficient mice after 12 weeks consuming 60% (kcal) fat diet with 2% (w/w) cholesterol and administration of the *Lb. mucosae* DPC 6426 and control group. Error bars represent standard errors of the means (SEM). p=0.090. However, statistically no differences were found for triglyceride concentrations in liver between the *Lb. mucosae* DPC 6426 fed group and the placebo control group following 12 weeks of dietary intervention.
Figure 24:
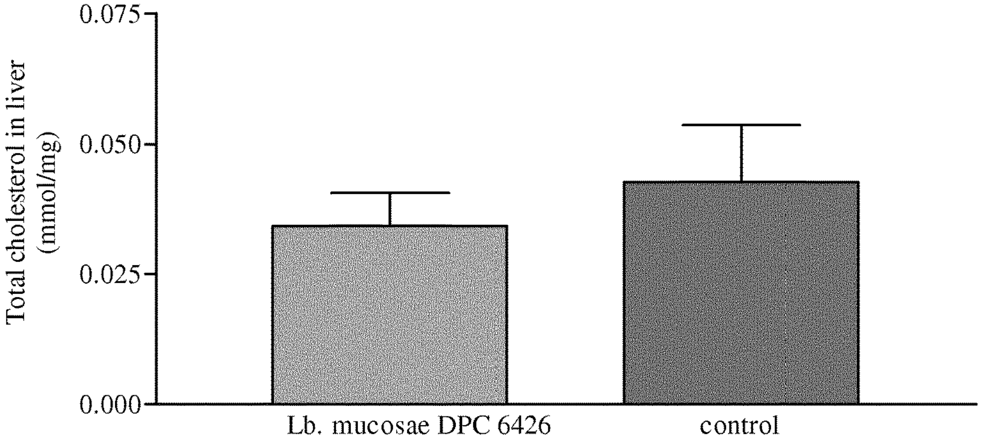
FIG. 24 is a bar chart illustrating total cholesterol levels in livers of apoE-deficient mice after 12 weeks consuming 60% (kcal) fat diet with 2% (w/w) cholesterol and administration of the *Lb. mucosae* DPC 6426 and control group. Error bars represent standard errors of the means (SEM). p=0.488. However, statistically no differences were found for total cholesterol concentrations in the liver between the Lb. *mucosae* DPC 6426 fed group and the placebo control group following 12 weeks of dietary intervention.
Figure 25:
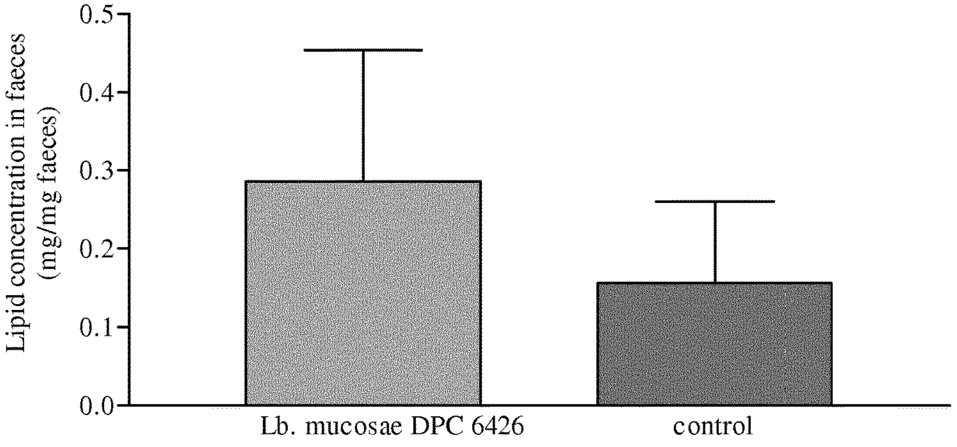
FIG. 25 is a bar chart illustrating faecal lipids of apoE-deficient mice after 12 weeks consuming 60% (kcal) fat diet with 2% (w/w) cholesterol and administration of the *Lb. mucosae* DPC 6426 and control group. Error bars represent standard errors of the means (SEM). p=0.603. No differences in faecal lipid concentrations between the *Lb. mucosae* DPC 6426 fed group and the placebo control group was found.

Oral administration of EPS-producing *Lb. mucosae* DPC 6426 lead to significantly increased HDL-cholesterol to total cholesterol in liver compared to the placebo control group (FIG. 22). Increased HDL to total cholesterol levels are reported to reduce the risk of atherosclerosis. In addition, serum triglyceride concentrations were significantly reduced following oral administration of EPS-producing *Lb. mucosae* DPC 6426 group, compared to the placebo control group (FIG. 23).

Figure 26:
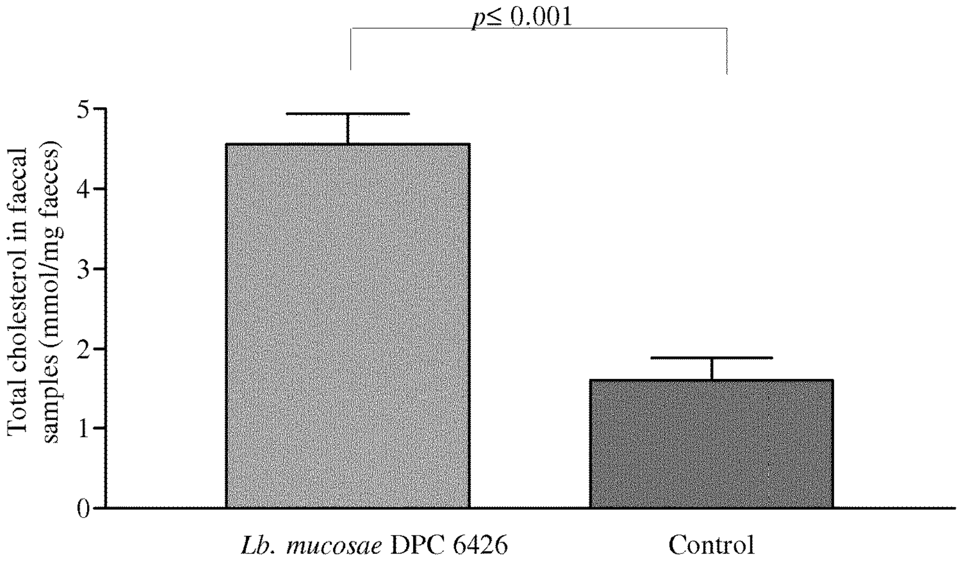
FIG. 26 is a bar chart illustrating total faecal cholesterol concentration of apoE-deficient mice after 12 weeks consuming 60% (kcal) fat diet with 2% (w/w) cholesterol and administration of the *Lb. mucosae* DPC 6426 and control group. Error bars represent standard errors of the means (SEM). p=0.0001. Significantly increased (p≤0.001) cholesterol excretion was found for the *Lb. mucosae* DPC 6426 fed group compared with the placebo control group.
Figure 27:
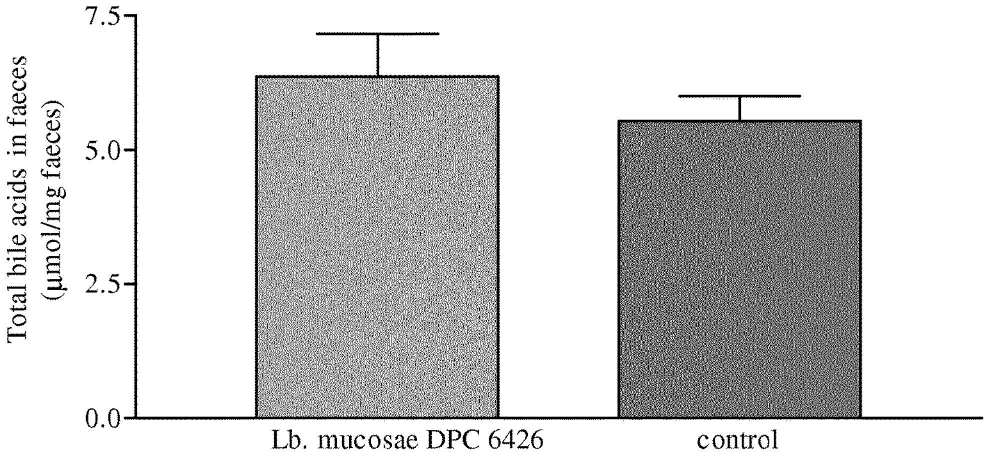
FIG. 27 is a bar chart illustrating total bile acid concentration in faeces of apoE-deficient mice after 12 weeks consuming 60% (kcal) fat diet with 2% (w/w) cholesterol and administration of the *Lb. mucosae* DPC 6426 and control group. Error bars represent standard errors of the means (SEM). p=0.442. No differences were found for total faecal bile acid concentrations between the *Lb. mucosae* DPC 6426 fed group compared with the placebo control group.
Figure 28:
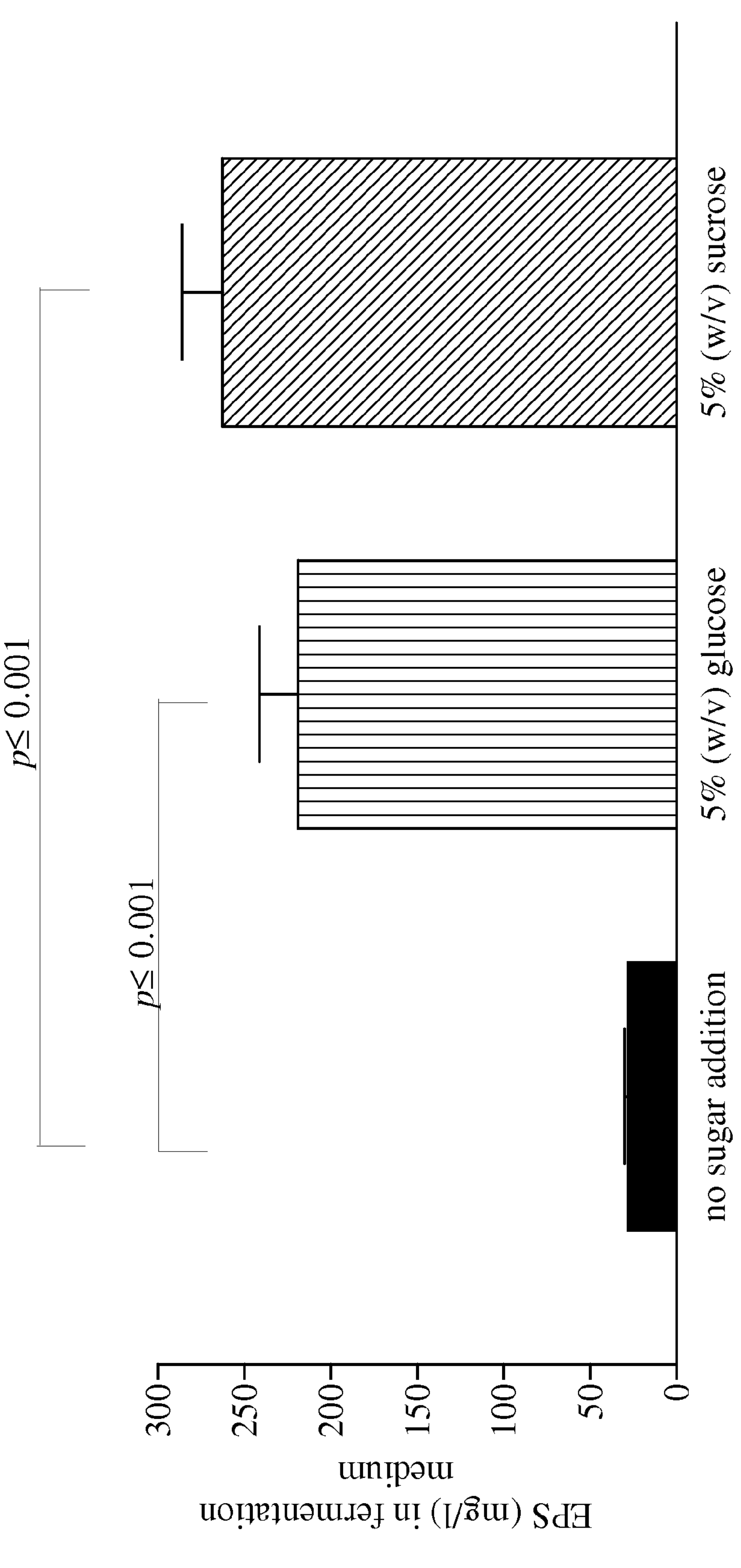
FIG. 28 is a bar chart illustrating EPS concentrations (mg/l) in 10% (w/v) RSM fermentation medium with and without the addition of either 5% (w/v) glucose or 5% (w/v) sucrose at the end of fermentation (48 h). Error bars represent standard errors of the means from triplicate experiments. While no statistical differences were found for cell growth between different fermentation media for pH and lactic acid production, EPS production of *Lb. mucosae* DPC 6426 statistically differed (p≤0.001) with different fermentation media. The EPS concentrations varied between 28.3 mg/l (±1.83) for 10% (w/v) RSM medium and 262.6 mg/l (±23.48) for 10% (w/v) RSM supplemented with 5% (w/v) sucrose. EPS production of *Lb. mucosae* DPC 6426 was found for both, 10% (w/v) RSM supplemented with 5% (w/v) glucose and sucrose. However, higher levels of EPS were found for fermentation medium with the addition of 5% (w/v) sucrose compared to 5% (w/v) glucose without reaching significant levels.
Figure 29:
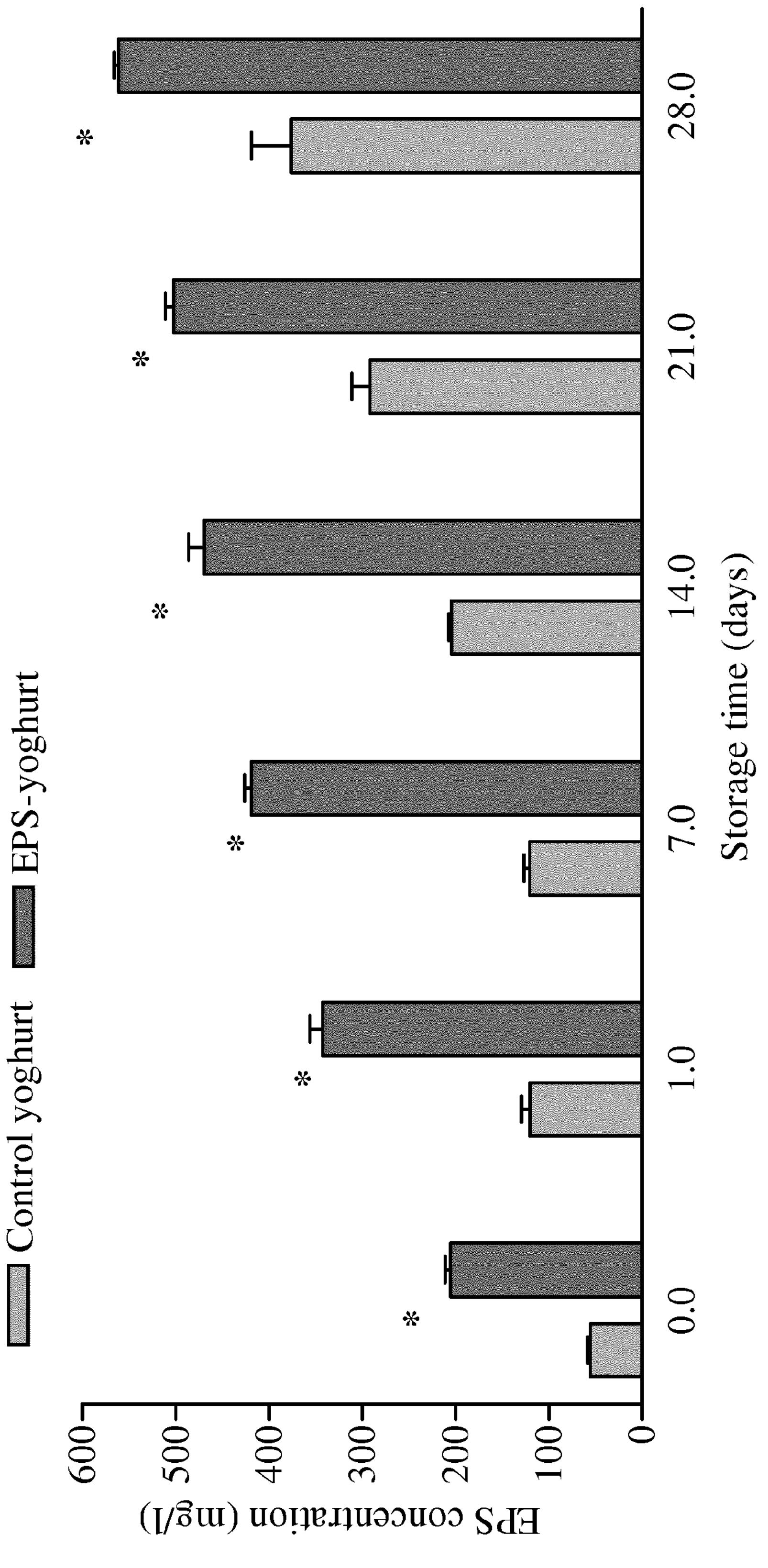
FIG. 29 is a bar chart illustrating EPS concentrations (mg/l) of the control yoghurt and the EPS-containing yoghurt during storage at 4° C. for 28 days. Error bars represent standard errors of the means from triplicate experiment. An asterisk denotes a significant difference between control yoghurt and EPS-containing yoghurt (* p≤0.05).
Figure 30:
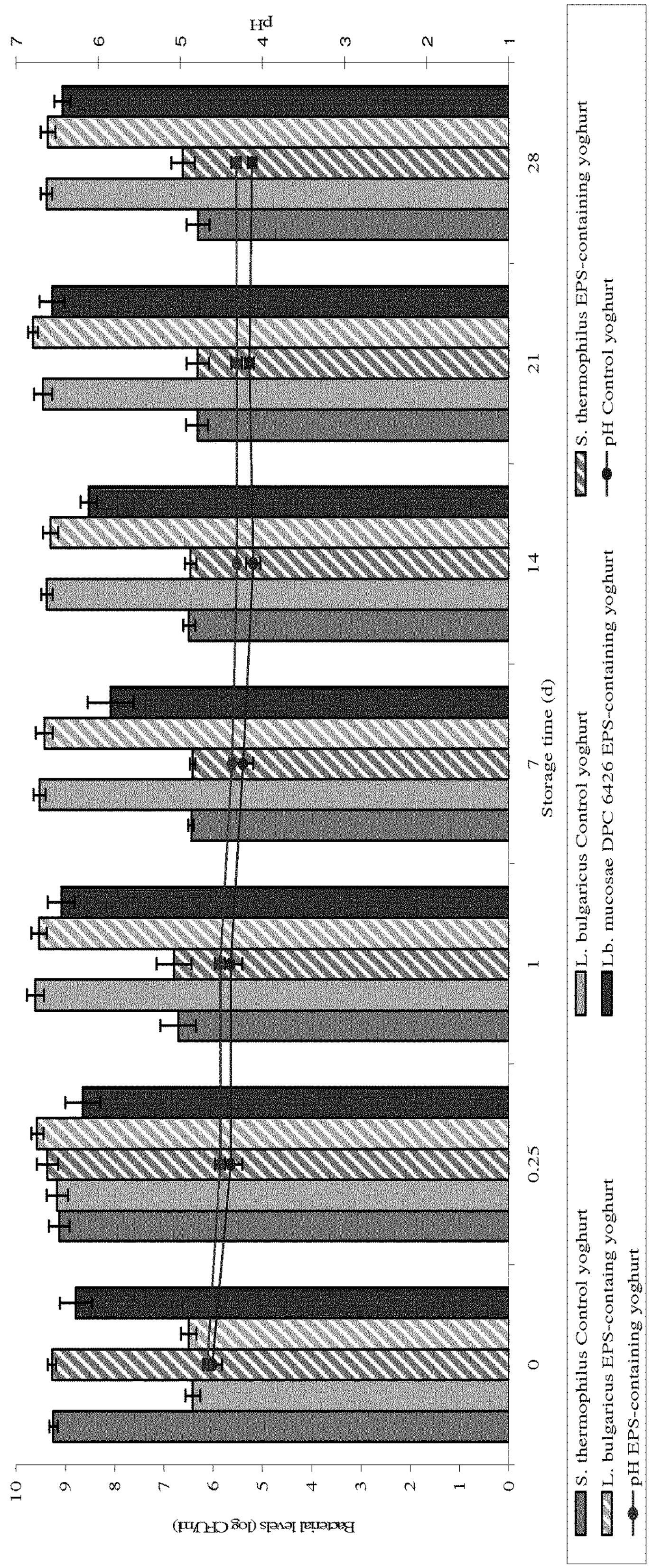
FIG. 30 is a bar chart illustrating the viability of CH-1 culture (bars) and EPS-producing strain *Lb. mucosae* DPC 6426 (bars) and pH development of control and EPS-containing yoghurt (dots) during, after fermentation at 37° C. anaerobically and during storage at 4° C. for 28 days. Error bars represent standard errors of the means from triplicate experiments. The in situ production of EPS had no effect on the fermentation efficacy of *S. thermophilus* and *L. delbrueckii* subsp. *bulgaricus* and did not affect viability during storage at 4° C. for 28 days. The pH development for control and EPS-containing yoghurt did not show a significant difference for day 1 (p=0.177) and day 7 (p=0.100). However, the EPS-containing yoghurt showed significant less (p≤0.01) post acidification compared to control yoghurt during storage at 4° C. at day 14, day 21 and day 28. For day 14 of storage at 4° C., the pH of the control yoghurt was 4.11 (±0.08) and the pH for EPS-containing yoghurt was 4.31 (±0.02). at day 21 of storage at 4° C., the pH of the control yoghurt was 4.16 (±0.05) and the pH for EPS-containing yoghurt was 4.32 (±0.06). At day 28 of storage at 4° C., the pH of the control yoghurt was 4.13 (±0.05) and the pH for EPS-containing yoghurt was 4.32 (±0.05).
Figure 31:
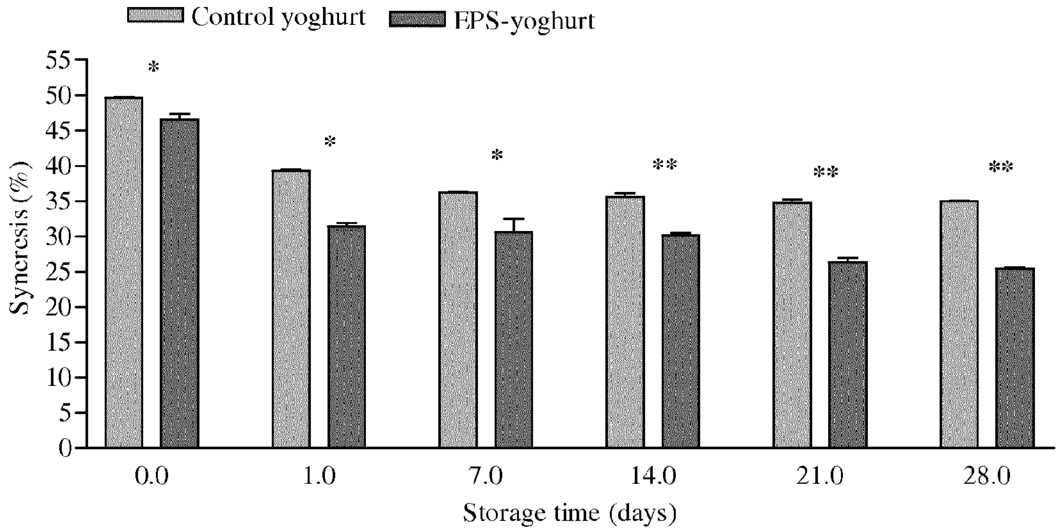
FIG. 31 is a bar chart illustrating the level of syneresis in the control yoghurt and in the EPS-containing yoghurt during storage at 4° C. for 28 days. Syneresis or whey separation is the spontaneous appearance of whey on milk gel surface and is a negative factor in terms of quality of yoghurt, and negatively affects consumer acceptance. Error bars represent standard errors of the means from triplicate experiments. An asterisk denotes a significant difference in syneresis between control yoghurt and the EPS-containing yoghurt (* p≤0.05, ** p≤0.01). The EPS-containing yoghurt had a significantly lower level of syneresis (p≤0.05) compared to the control yoghurt throughout storage at 4° C. for 28 days.
Figure 32:
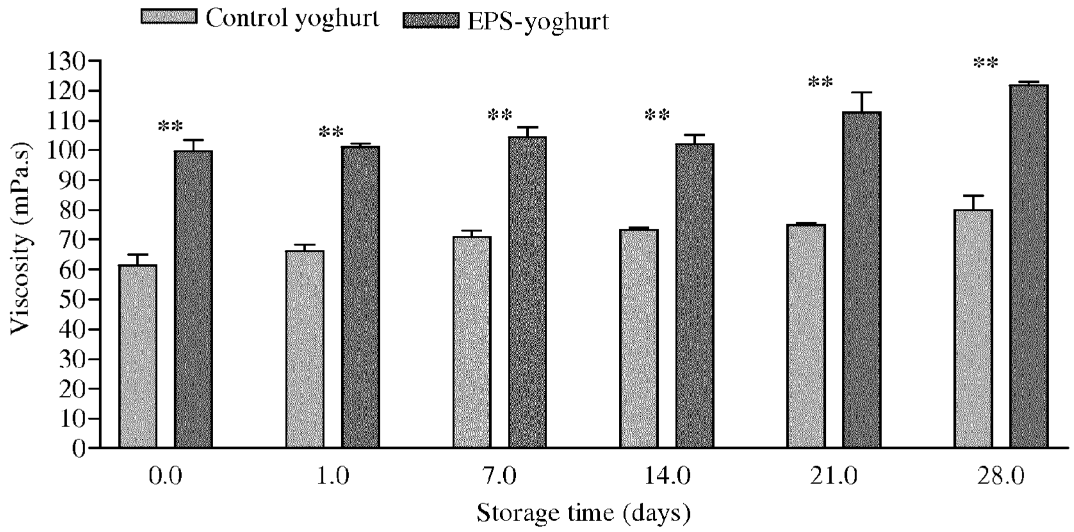
FIG. 32 is a bar chart illustrating the viscosity measurements (mPa·s), at a shear rate of 200 $s^{-1}$, of the control yoghurt and the EPS-containing yoghurt during storage at 4° C. for 28 days. Error bars represent standard errors of the means from 12 readings for each time point. An asterisk denotes a significant difference between control yoghurt and EPS-containing yoghurt (** p≤0.01). The EPS-containing yoghurt showed significantly (p≤0.01) higher levels of viscosity throughout storage at 4° C. for 28 days, compared to the control yoghurt. The viscosity values of the EPS-containing yoghurt gradually increased, starting at 99.72 mPa·s (±2.61) at day 1 of storage to 121.80 mPa·s (±0.85) at day 28 of storage at 4° C. for 28 days.

Oral administration of *Lb. mucosae* DPC 6426 resulted in statistically increased faecal cholesterol excretion when compared to the placebo control group (FIG. 26) which indicates an inhibition of cholesterol uptake in *Lb. mucosae* DPC 6426 fed animals, induced by EPS produced by *Lb. mucosae* DPC 6426.

Although not wanting to be bound to theory, the Applicant postulates that in situ EPS produced by *Lb. mucosae* DPC 6426 in the intestinal tract influences the inflammatory glycoprotein sVCAM-1, which is involved in the pathogenesis of atherosclerosis development and that the in situ produced EPS by *Lb. mucosae* DPC 6426 inhibits the absorption of cholesterol.

Figure 33:
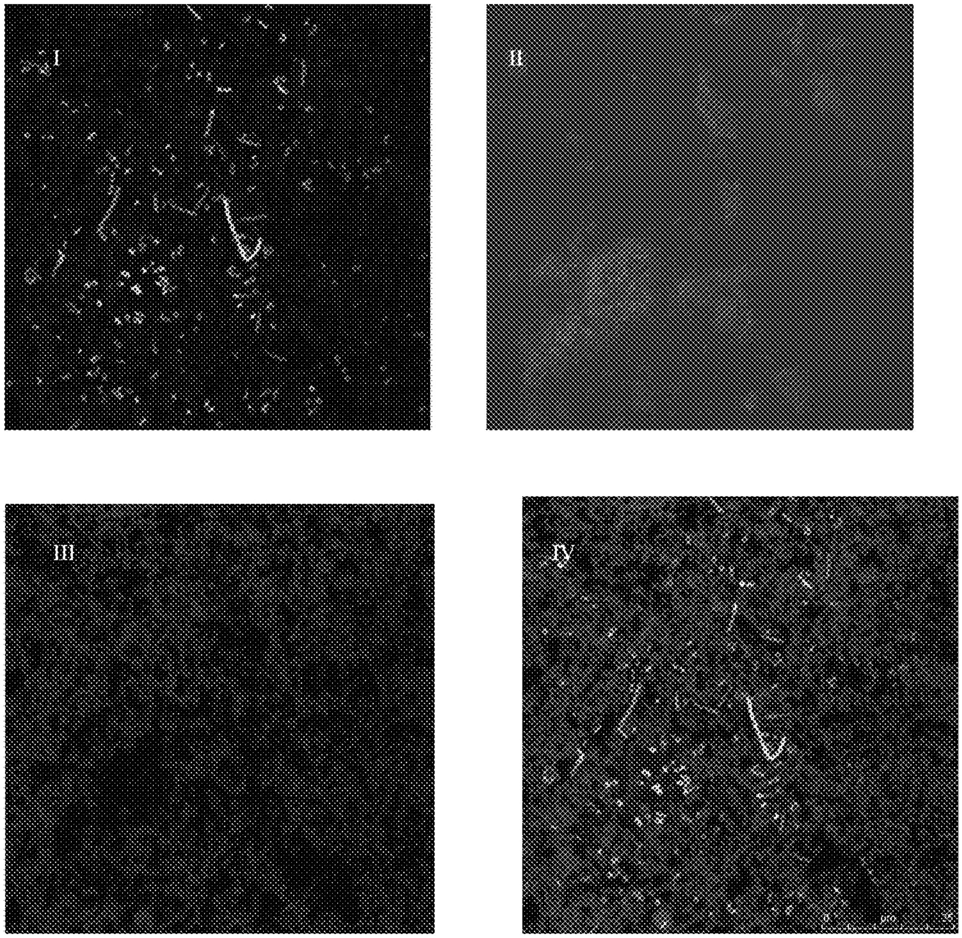
FIG. 33 illustrates confocal laser scanning microscope (CLSM) images of the unstirred EPS-containing yoghurt. The bacteria (I), the EPS (II), and the protein aggregates (III) were labelled with Syto 9, wheat germ agglutinin, Alexa Fluor 555 and fast Green FCF. Therefore, the bacteria appear green, the protein network appears red and the EPS fluoresces blue. An over-layer of images I, II and III is displayed in IV.
Figure 34:
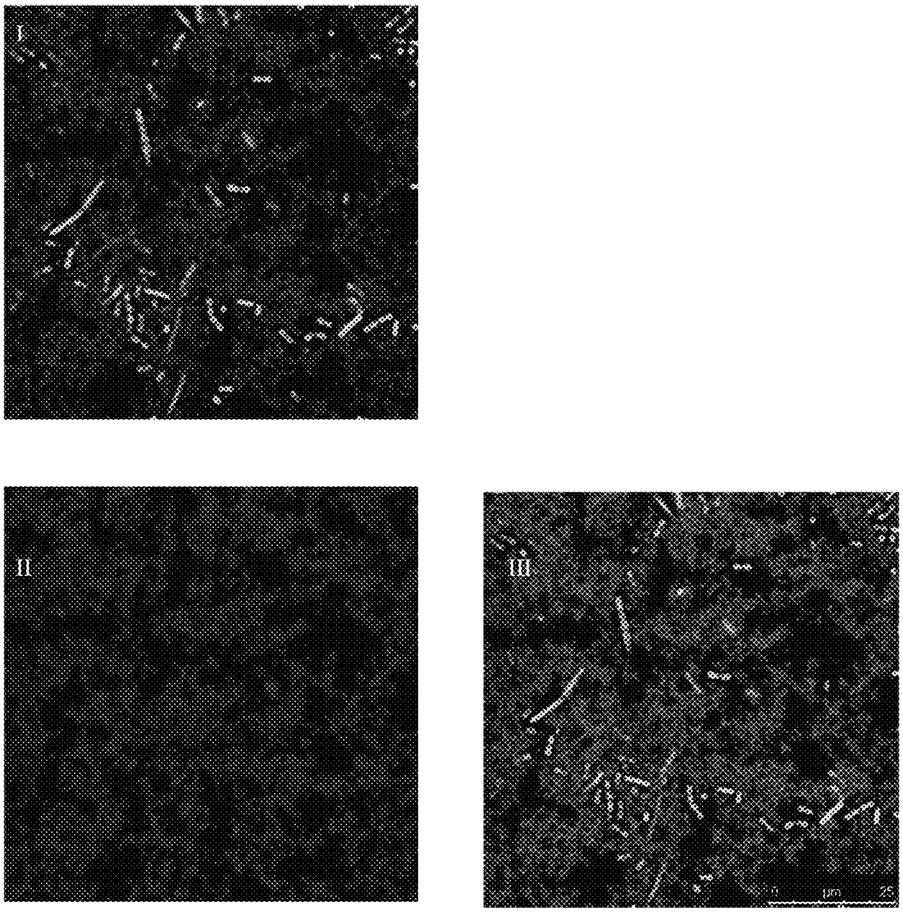
FIG. 34 illustrates confocal laser scanning microscope (CLSM) images of the unstirred control yoghurt. The bacteria (I) and the protein aggregates (II) were labelled with Syto 9, wheat germ agglutinin, Alexa Fluor 555 and fast Green FCF. Therefore, the bacteria appear green, the protein network appears red and EPS did not fluoresce. An over-layer of image I and labelled protein aggregate is displayed in III.
Figure 35:
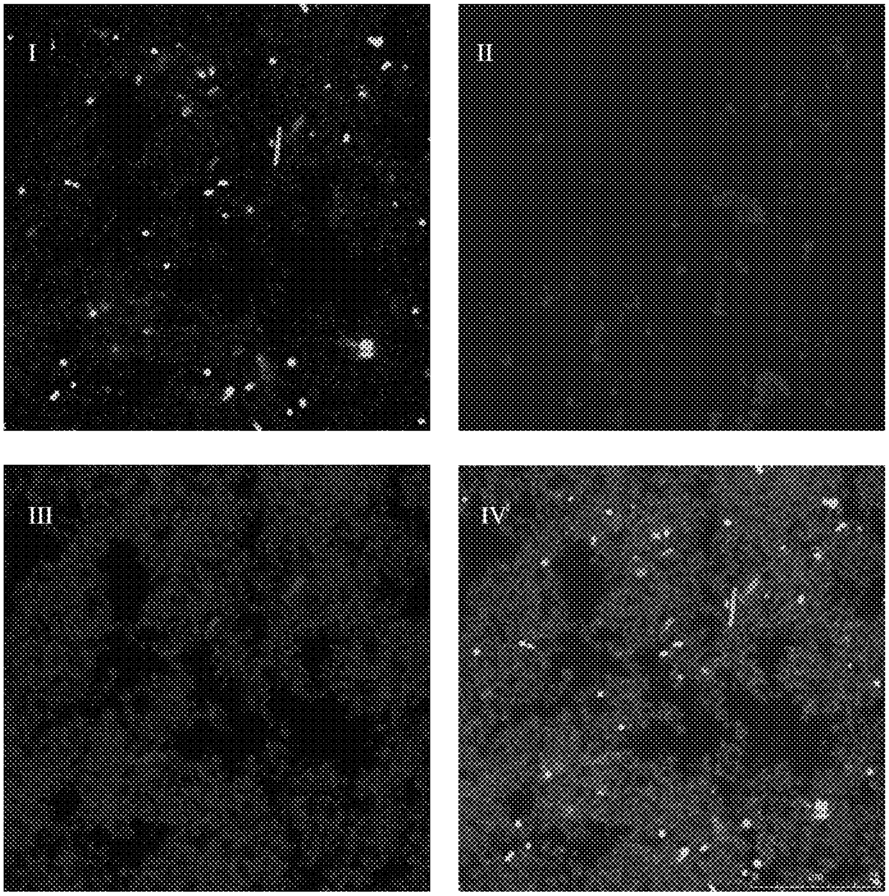
FIG. 35 illustrates confocal laser scanning microscope (CLSM) images of the stirred EPS-containing yoghurt. The bacteria (I), the EPS (II), and the protein aggregates (III) were labelled with Syto 9, wheat germ agglutinin, Alexa Fluor 555 and fast Green FCF. Therefore, the bacteria appear green, the protein network appears red and the EPS fluoresces blue. An over-layer of images I, II and III is displayed in IV.
Figure 36:
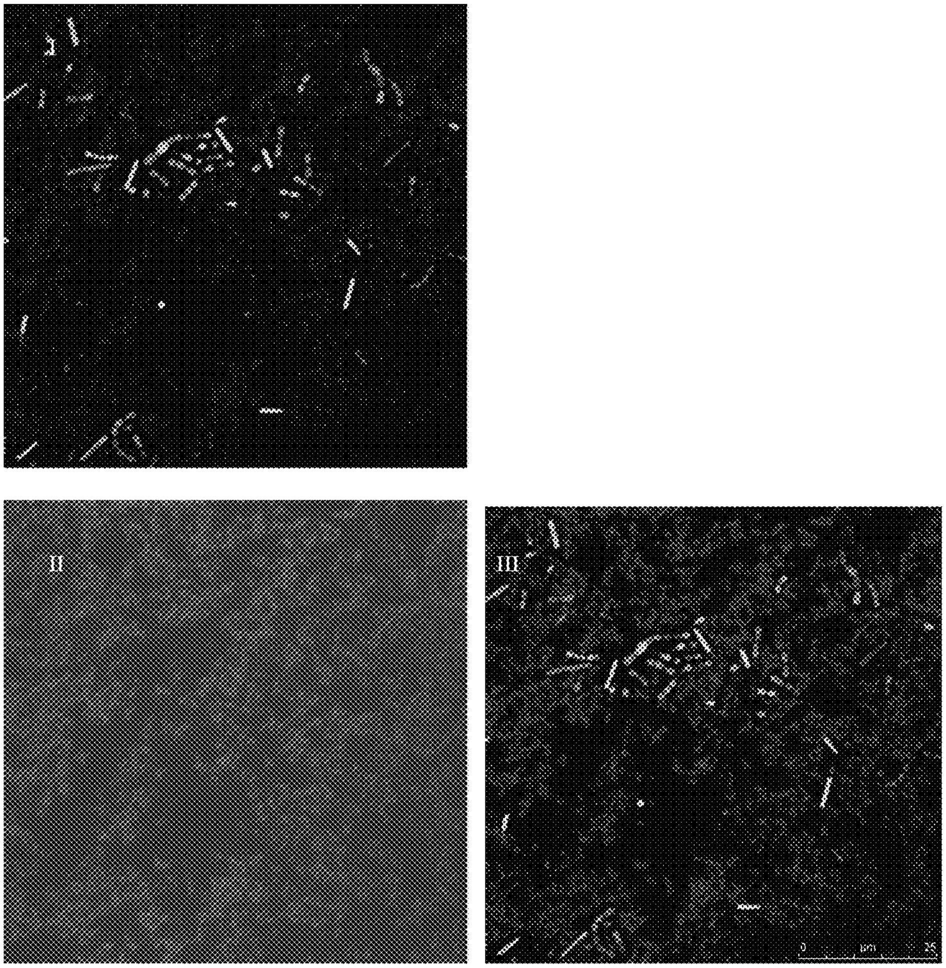
FIG. 36 illustrates confocal laser scanning microscope (CLSM) images of the stirred control yoghurt. The bacteria (I), the EPS (II), and the protein aggregates (II) were labelled with Syto 9, wheat germ agglutinin, Alexa Fluor 555 and fast Green FCF. Therefore, the bacteria appear green, the protein network appears red and the EPS did not fluoresce. An over-layer of image I and labelled protein aggregate is displayed in III.
Figure 37:
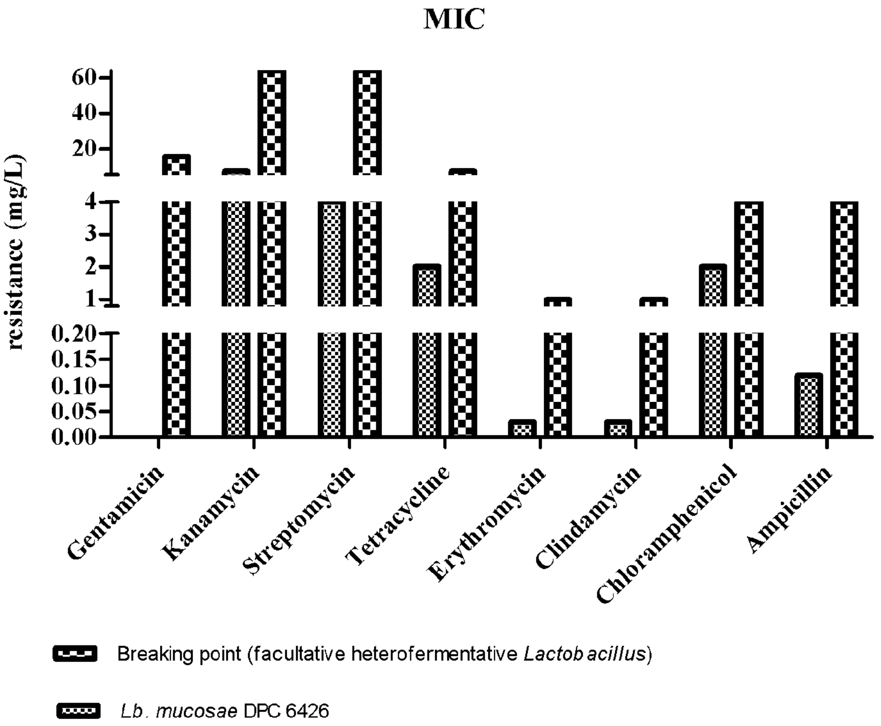
FIG. 37A illustrates the minimal inhibitory concentrations (MIC) of antibiotics based on International Standard (ISO 10932, IDF 223) from susceptible strains defining microbiological breakpoint of *Lb. mucosae* DPC 6426 as outlined by the FEEDAP Panel. From the assessment of the generated data *Lb. mucosae* DPC 6426 quantitative MIC determination is below breakpoints of facultative heterofermentative lactobacilli and therefore the strain is acceptable.
FIG. 37B illustrates the minimal inhibitory concentrations (MIC) of additional antibiotics not shown in FIG. 7A based on International Standard (ISO 10932, IDF 223) from susceptible strains defining microbiological breakpoint of *Lb. mucosae* DPC 6426 as outlined by the FEEDAP Panel.
Figure 37:
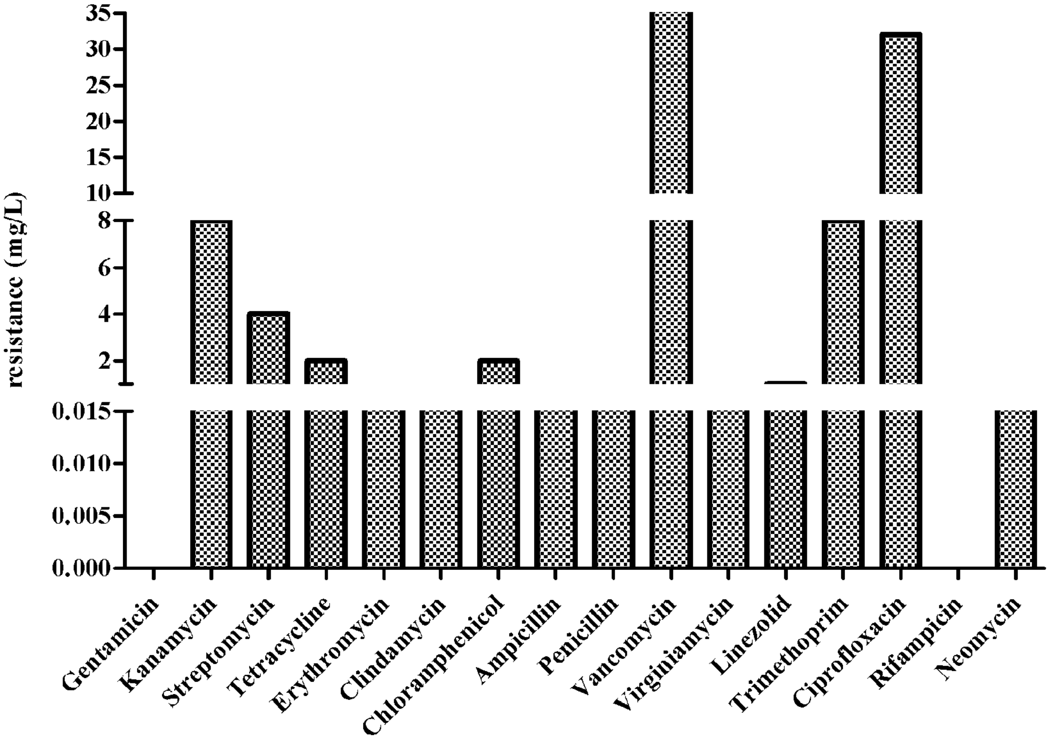
Figure 38:
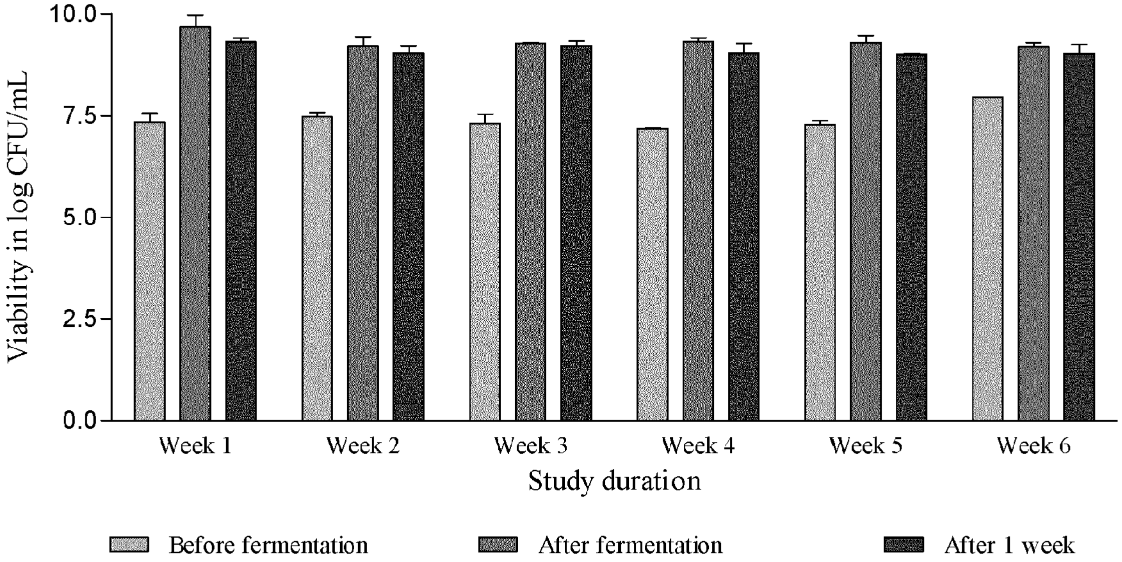
FIG. 38 illustrates that the (A) viability of *Lb. mucosae* DPC 6426 after fermentation and after 1 week of storage at 4° C. maintained at high numbers (9.33±0.11 log(CFU)/ml and 9.11±0.11 log(CFU)/ml). (B) In situ produced EPS during fermentation maintained similar with ~162.18 $mgL^{-1}$ EPS. (C) Sensory results of independent taste panel of vanilla flavoured fermented milk containing *Lb. mucosae* DPC 6426 are represented below.
Figure 38:
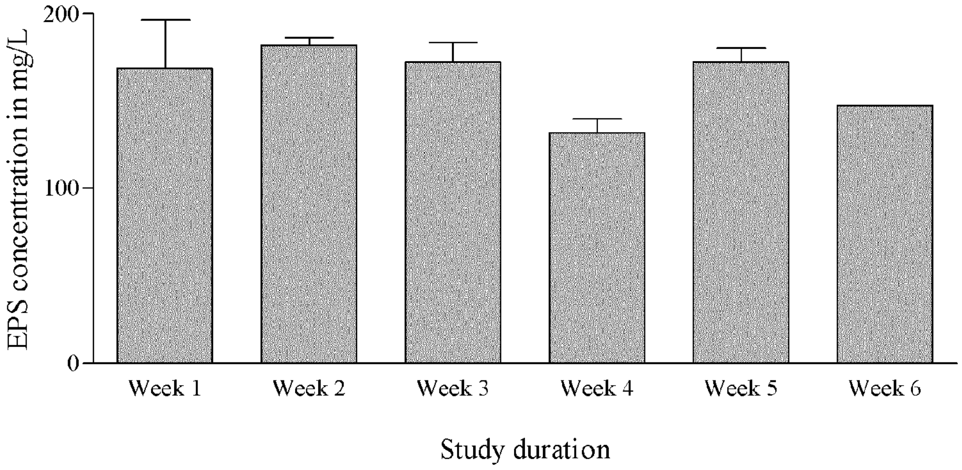
Figure 38:
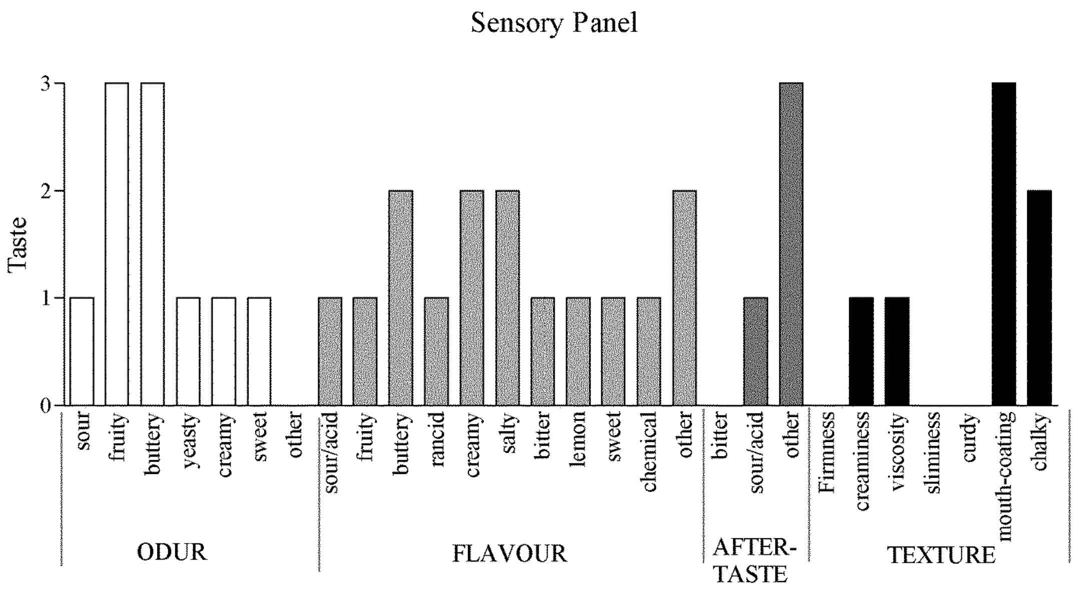

Unstirred control yoghurt samples appeared to have larger pores than stirred control yoghurt samples (FIG. 34 III). The microstructure of the stirred control yoghurt showed a rearrangement of the protein network creating even larger pores compared to the unstirred sample (FIG. 36 III). The microstructure of the EPS-containing yoghurt appeared finer and exhibited a well-defined continuous protein network with smaller pores, compared to the control yoghurt sample (FIG. 33 III). Stirred EPS-containing yoghurt samples displayed a less regular protein network, made up of thick strands consisting of densely aggregated protein particles (FIG. 35 III). The control and EPS-containing yoghurt protein network, cultures and EPS were fluorescently-labelled to allow visualization of the cultures and EPS distribution in the protein network, in the control and EPS-containing yoghurt samples. Fast Green FCF labelled the protein and displayed the protein in red colour (FIGS. 33 to 36 III), Syto 9 labelled live and dead bacteria and the cultures appeared in green (FIGS. 33 to 36 I). The EPS was labelled with Wheat germ agglutinin, Alexa Fluor 555 and displayed the EPS in blue (FIGS. 33 to 36 II). FIG. 33 IV and FIG. 35 IV showed the distribution of EPS within the network of unstirred and stirred EPS-containing yoghurt samples. In the unstirred EPS-containing yoghurt samples, EPS was observed in the pores of the protein network. In contrast, the distribution of the EPS in stirred EPS-containing yoghurt samples appeared on the edges of the pores and was more likely connected within the protein matrix. The yoghurt culture CH-1 and the EPS producing *Lb. mucosae* DPC 6426 were mixed thoroughly within the EPS-containing yoghurt samples (FIG. 33 I) for unstirred EPS-containing yoghurt samples and within the protein network for stirred EPS-containing samples (FIG. 35 I). Cultures in the control yoghurt sample were mainly found at the edge of serum pores or within the casein network (FIGS. 34 and 36 I). In addition, it was observed that *Lb. mucosae* DPC 6426 was attached to EPS in the unstirred and stirred EPS-containing yoghurt samples.

Figure 39:
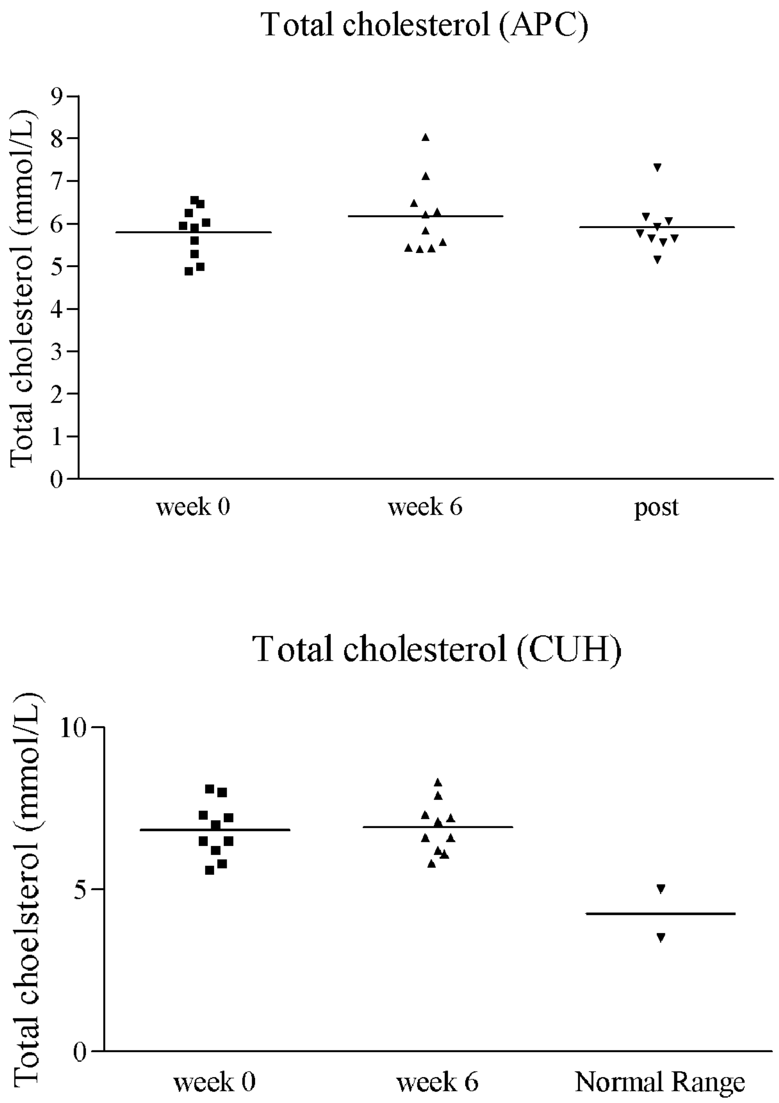
FIG. 39 illustrates a study to determine if *Lb. mucosae* DPC 6426 reduces total cholesterol in mildly hypercholesterolaemic (≥5 mmol/L and <7.5 mmol/L) male adults. Samples were analysed using Cholestech LDX system (APC) and independently at Cork University Hospital ("CUH").

Ingestion of fermented milk containing ~$10^{10}$ CFU per 100 ml viable *Lb. mucosae* DPC 6426 and ~162.2 mg/L (±18.7 mg/L) EPS daily for 6 weeks resulted in no significant differences (APC: p=0.1580; CUH: p=0.3496) in total cholesterol concentrations in fasting blood at the end of this study (FIG. 39). The primary objective of this study was to determine if *Lb. mucosae* DPC 6426 reduces total cholesterol in mildly hypercholesterolaemic (≥5 mmol/L and <7.5 mmol/L) male adults. However, results of this study did not show significant differences (APC: p=0.1580; CUH: p=0.3496) in total cholesterol concentrations between the beginning of the study and after ingestion of $10^{10}$ CFU per 100 ml *Lb. mucosae* DPC 6426 for 6 weeks daily.

Figure 40:
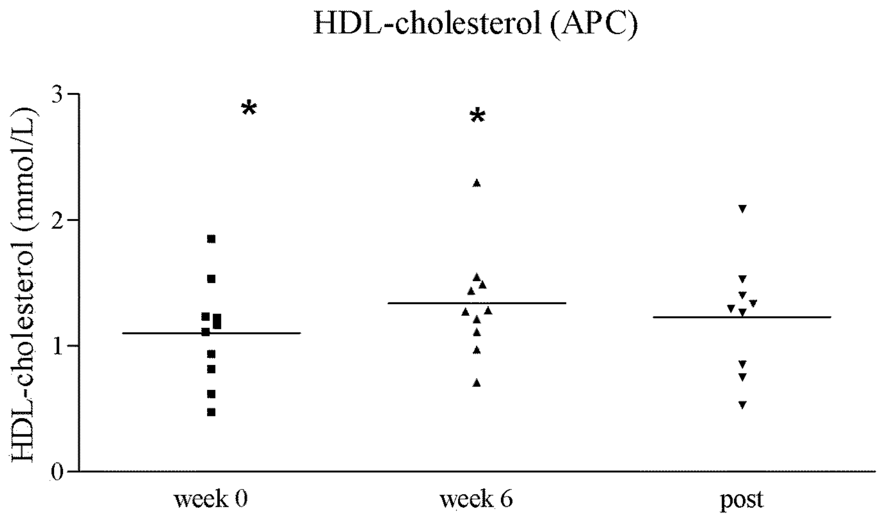
FIG. 40 illustrates a study to determine if *Lb. mucosae* DPC 6426 reduces HDL-cholesterol concentrations in mildly hypercholesterolaemic (≥5 mmol/L and <7.5 mmol/L) male adults. Samples were analysed using Cholestech LDX system (APC) and independently at CUH.
Figure 40:
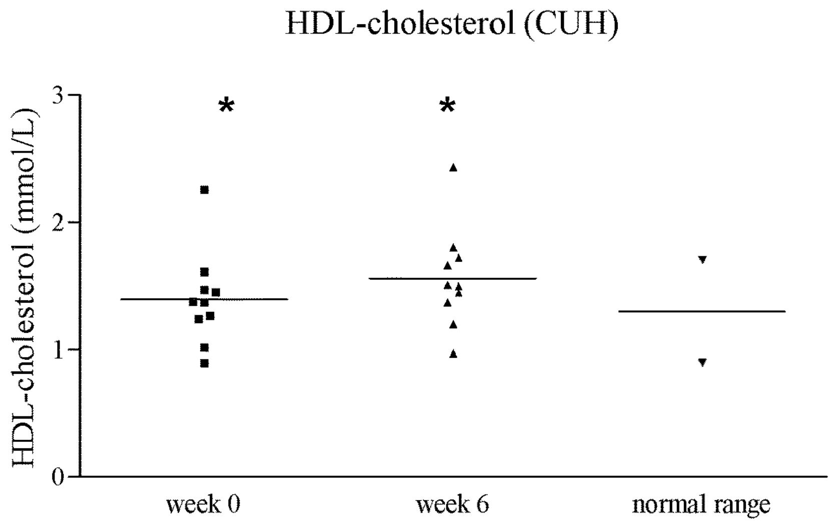
Figure 41:
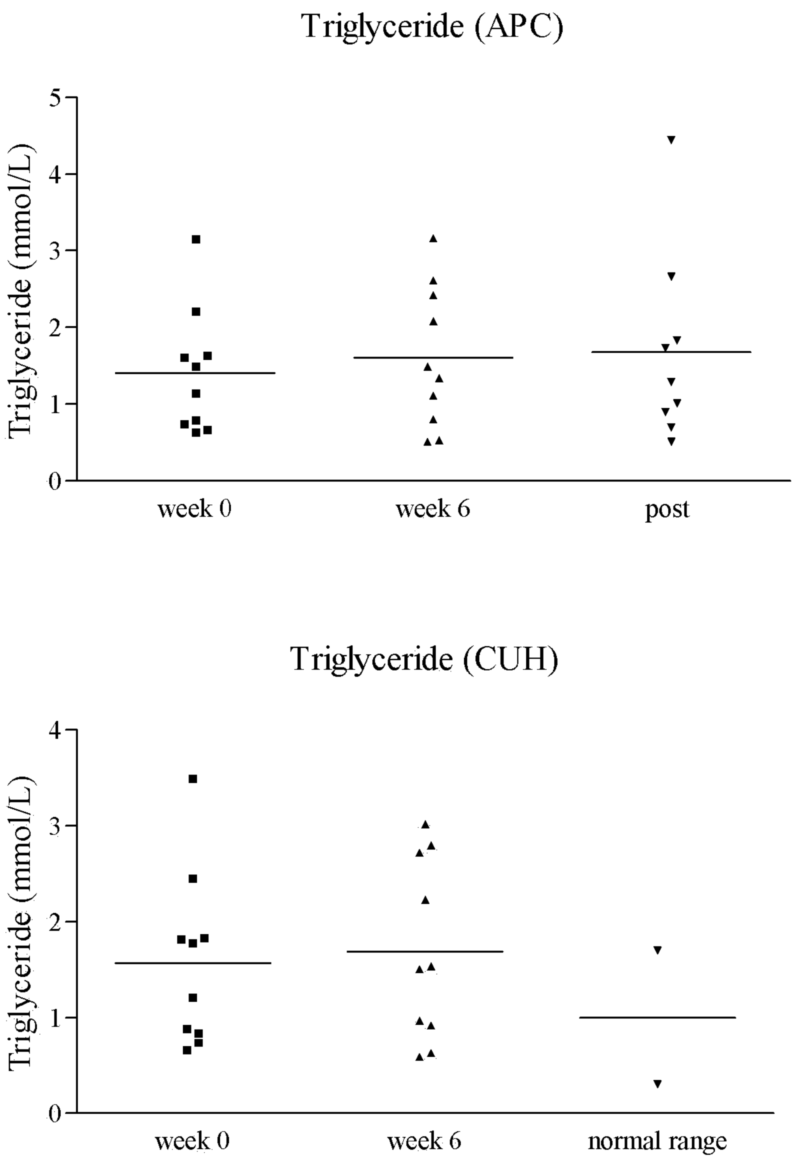
FIG. 41 illustrates a study to determine if *Lb. mucosae* DPC 6426 effects triglyceride concentrations in mildly hypercholesterolaemic (≥5 mmol/L and <7.5 mmol/L) male adults. Samples were analysed using Cholestech LDX system (APC) and independently at CUH.
Figure 42:
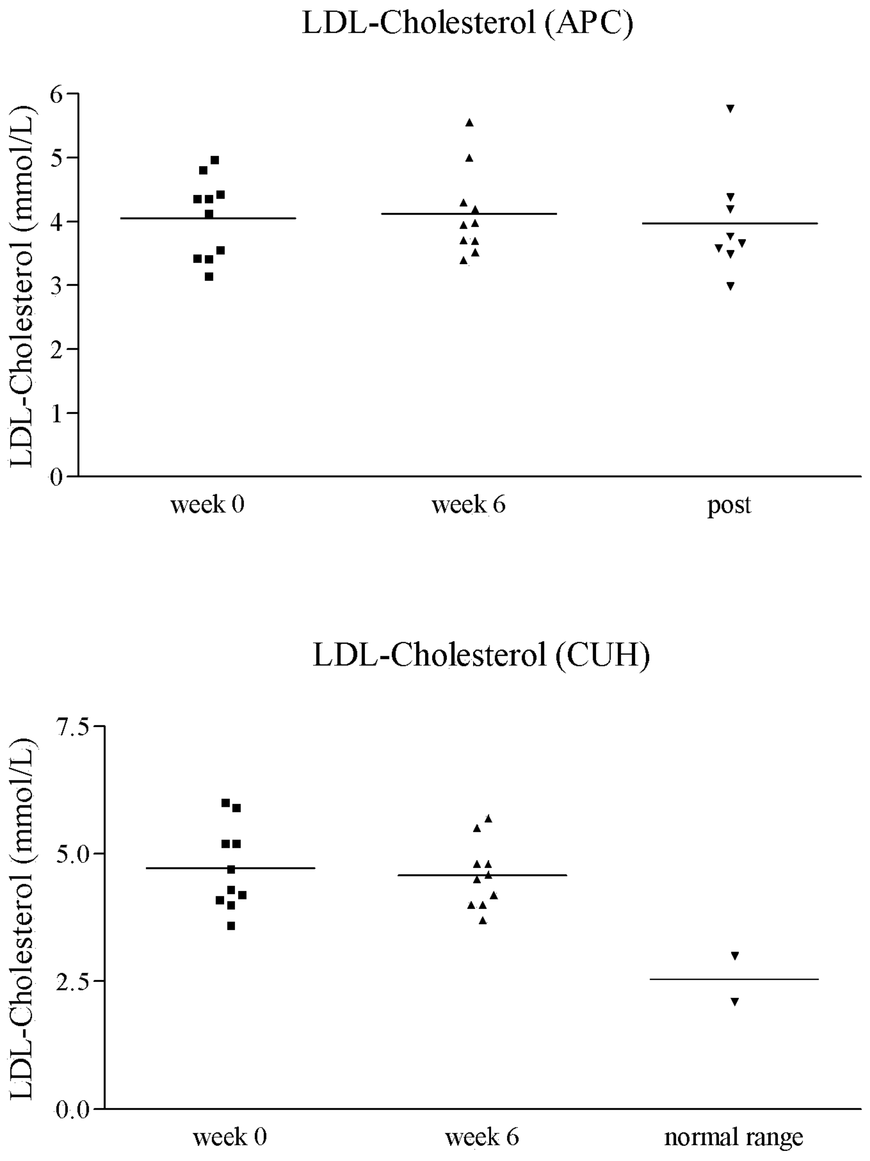
FIG. 42 illustrates a study to determine if *Lb. mucosae* DPC 6426 effects LDL-cholesterol levels in mildly hypercholesterolaemic (≥5 mmol/L and <7.5 mmol/L) male adults. Samples were analysed using Cholestech LDX system (APC) and independently at CUH.
Figure 43:
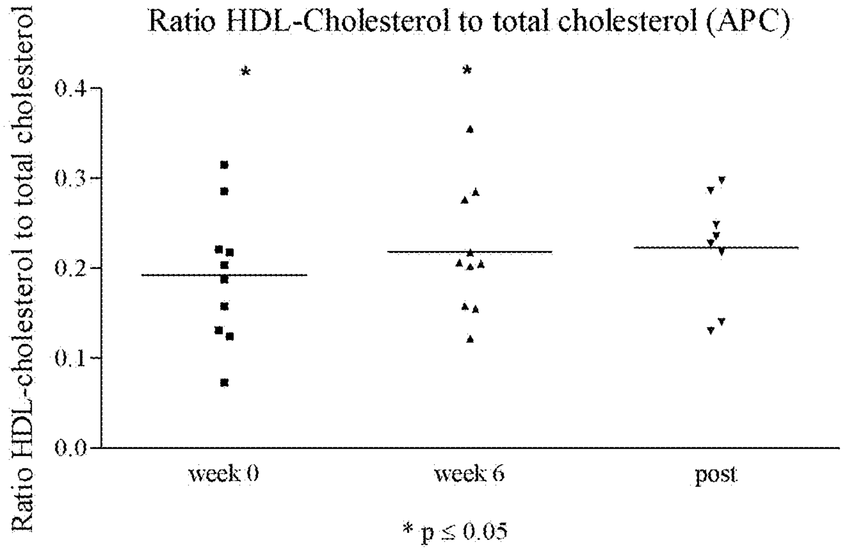
FIG. 43 illustrates the HDL cholesterol to total cholesterol ratio and glucose results from the studies of FIGS. 39 and 40. Samples were analysed using Cholestech LDX system (APC) and independently at CUH.
Figure 43:
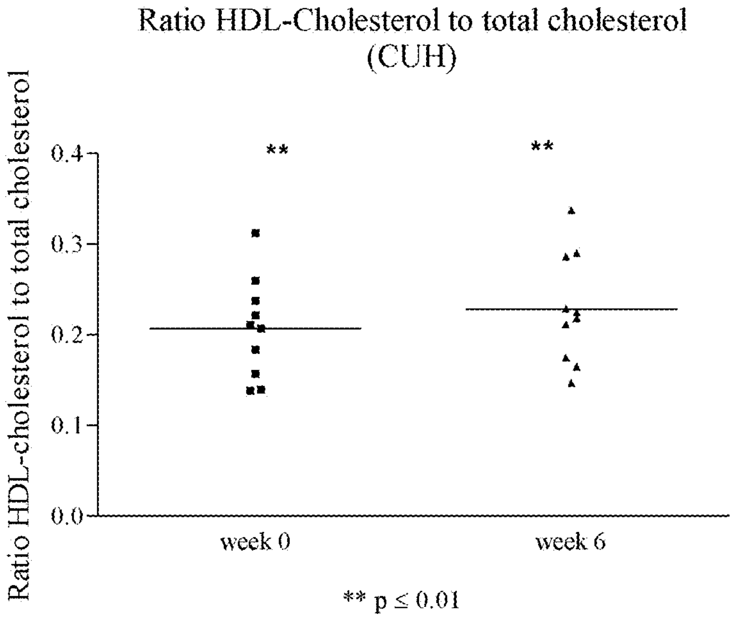
Figure 44:
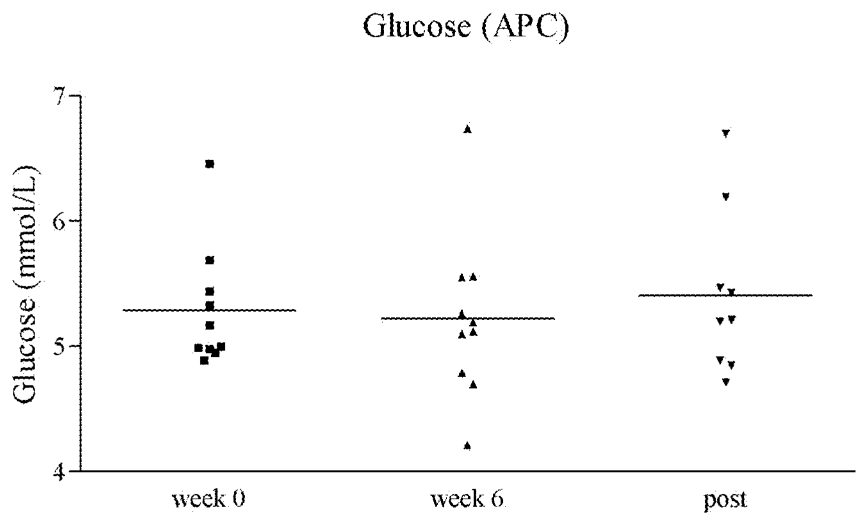
FIG. 44 illustrates a study to determine if *Lb. mucosae* DPC 6426 effects glucose levels in mildly hypercholesterolaemic (≥5 mmol/L and <7.5 mmol/L) male adults. Samples were analysed using Cholestech LDX system (APC) and independently at Cork University Hospital (CUH).
Figure 44:
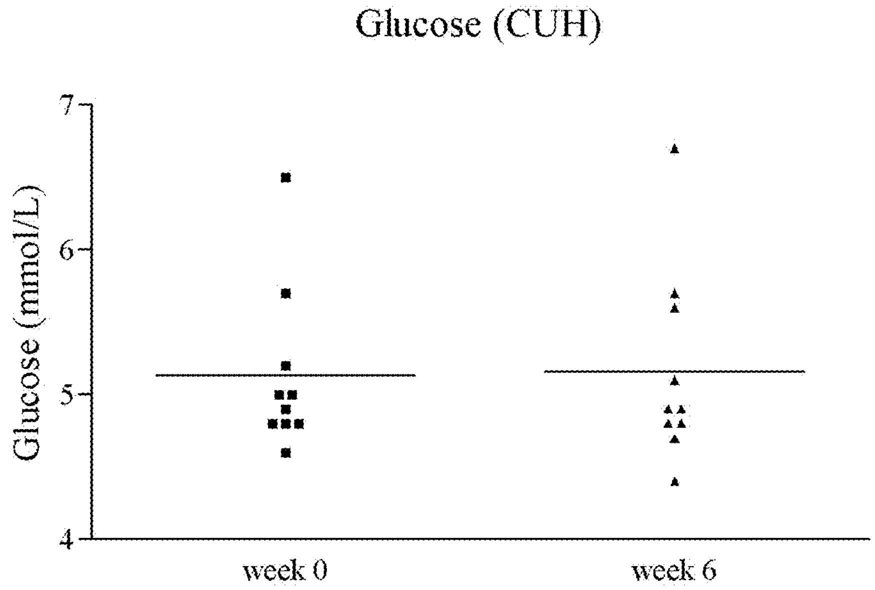

Secondary objectives of this study were to determine if *Lb. mucosae* DPC 6426 reduces LDL-cholesterol concentrations in mildly hypercholesterolaemic (≥5 mmol/L and <7.5 mmol/L) male adults (FIG. 40), to determine if *Lb. mucosae* DPC 6426 effects HDL-cholesterol concentrations in mildly hypercholesterolaemic (≥5 mmol/L and <7.5 mmol/L) male adults (FIG. 41) and to determine if *Lb. mucosae* DPC 6426 effects triglyceride levels in mildly hypercholesterolaemic (≥5 mmol/L and <7.5 mmol/L) male adult (FIG. 42). No significant changes were found for LDL cholesterol concentration (APC: p=0.4982; CUH: p=0.1959) and triglyceride concentrations (APC: p=0.1709;

CUH: p=0.3645) between the beginning of the study and following ingestion of $10^{10}$ CFU per 100 ml Lb. mucosae DPC 6426 for 6 weeks daily.

Nevertheless, ingestion of $10^{10}$ CFU per 100 ml Lb. mucosae DPC 6426 for 6 weeks daily significantly increased HDL cholesterol concentration (APC: p≤0.05; CUH: p≤0.001) in blood and increased the ratio of total cholesterol to HDL cholesterol (APC: p≤0.05; CUH: p≤0.01) in blood compared to the beginning of the study in mildly hypercholesterolaemic (≥5 mmol/L and <7.5 mmol/L) male adults.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

REFERENCES

Amatayakul T, Sherkat F & Shah N P (2006) Syneresis in set yogurt as affected by EPS starter cultures and levels of solids. *International Journal of Dairy Technology* 59: 216-221.

Brewster J D (2003) A simple micro-growth assay for enumerating bacteria. *Journal of microbiological methods* 53: 77-86.

Han S H, Chung M J, Lee S J & Rhee C (2006) Digestion-resistant fraction from soybean [*Glycine max* (L.) Merrill] induces hepatic LDL receptor and CYP7A1 expression in apolipoprotein E-deficient mice. *Journal of Nutritional Biochemistry* 17: 682-688.

Martensson O, Oste R & Holst O (2002) Texture promoting capacity and EPS formation by lactic acid bacteria in three different oat-based non-dairy media. *European Food Research and Technology* 214: 232-236.

Oboroceanu D, Wang L Z, Brodkorb A, Magner E & Auty M A E (2010) Characterization of beta-Lactoglobulin Fibrillar Assembly Using Atomic Force Microscopy, Polyacrylamide Gel Electrophoresis, and in Situ Fourier Transform Infrared Spectroscopy. *Journal of Agricultural and Food Chemistry* 58: 3667-3673.

Ruas-Madiedo P & de los Reyes-Gavilan C G (2005) Invited review: Methods for the screening, isolation, and characterization of exopolysaccharides produced by lactic acid bacteria. *Journal of Dairy Science* 88: 843-856.

Wagner V E, Bushnell D, Passador L, Brooks A I & Iglewski B H (2003) Microarray analysis of *Pseudomonas aeruginosa* quorum-sensing regulons: effects of growth phase and environment. *Journal of bacteriology* 185: 2080-2095.

The invention claimed is:

1. A method of reducing total serum cholesterol levels in a mammal, comprising a step of administering to the mammal an isolated *Lactobacillus mucosae* (DPC6426) strain deposited with the National Collection of Industrial and Marine Bacteria Limited (NCIMB) on 27 Jul. 2012 under NCIMB Deposit Accession No. 42015, or a variant thereof, wherein the isolated *Lactobacillus mucosae* (DPC6426) strain and variant thereof express an exopolysaccharide comprising monosaccharide residues xylose, fucose, mannose, glucose, galactose, N-acetylglucosamine, and N-acetylmannosamine.

2. A method of treating cardiovascular disease in a mammal, comprising a step of administering to the mammal an isolated *Lactobacillus mucosae* (DPC6426) strain deposited with the National Collection of Industrial and Marine Bacteria Limited (NCIMB) on 27 Jul. 2012 under NCIMB Deposit Accession No. 42015, or a variant thereof, wherein the isolated *Lactobacillus mucosae* (DPC6426) strain and variant thereof express an exopolysaccharide comprising monosaccharide residues xylose, fucose, mannose, glucose, galactose, N-acetylglucosamine, and N-acetylmannosamine.

3. A fermented dairy product comprising an isolated *Lactobacillus mucosae* (DPC6426) strain deposited with the National Collection of Industrial and Marine Bacteria Limited (NCIMB) on 27 Jul. 2012 under NCIMB Deposit Accession No. 42015, or a variant thereof, wherein the isolated *Lactobacillus mucosae* (DPC6426) strain and variant thereof express an exopolysaccharide comprising monosaccharide residues xylose, fucose, mannose, glucose, galactose, N-acetylglucosamine, and N-acetylmannosamine.

4. The method of claim 1, wherein a ratio between the number of xylose, fucose, mannose, glucose, galactose, N-acetylglucosamine, and N-acetylmannosamine monosaccharide residues is about 1.3:0.5:10.0:4.8:3.3:1.5:0.2.

5. The method of claim 2, wherein a ratio between the number of xylose, fucose, mannose, glucose, galactose, N-acetylglucosamine, and N-acetylmannosamine monosaccharide residues is about 1.3:0.5:10.0:4.8:3.3:1.5:0.2.

6. The method of claim 3, wherein a ratio between the number of xylose, fucose, mannose, glucose, galactose, N-acetylglucosamine, and N-acetylmannosamine monosaccharide residues is about 1.3:0.5:10.0:4.8:3.3:1.5:0.2.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial sequence
<220> FEATURE:
<223> OTHER INFORMATION: Synthetic oligonulceotide
<220> FEATURE:
<221> NAME/KEY: prim_transcript
<222> LOCATION: (1)..(18)
<223> OTHER INFORMATION: 16s rRNA primer

<400> SEQUENCE: 1

agtttgatcc tggctcag                                                 18

<210> SEQ ID NO 2
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: prim_transcript
<222> LOCATION: (1)..(16)
<223> OTHER INFORMATION: 16s rRNA primer

<400> SEQUENCE: 2

taccttgtta cgactt                                                   16
```